(12) United States Patent
Lim et al.

(10) Patent No.: US 12,265,090 B2
(45) Date of Patent: Apr. 1, 2025

(54) INTER-ALPHA INHIBITOR PROTEINS

(71) Applicant: ProThera Biologics, Inc., Providence, RI (US)

(72) Inventors: Yow-Pin Lim, Providence, RI (US); Denice Spero, Providence, RI (US)

(73) Assignee: ProThera Biologics, Inc., Providence, RI (US)

( * ) Notice: Subject to any disclaimer, the term of this patent is extended or adjusted under 35 U.S.C. 154(b) by 0 days.

(21) Appl. No.: 17/404,841

(22) Filed: Aug. 17, 2021

(65) Prior Publication Data

US 2022/0099684 A1 Mar. 31, 2022

Related U.S. Application Data

(63) Continuation of application No. 16/608,531, filed as application No. PCT/US2018/029436 on Apr. 25, 2018, now abandoned.

(60) Provisional application No. 62/614,333, filed on Jan. 5, 2018, provisional application No. 62/490,003, filed on Apr. 25, 2017.

(51) Int. Cl.
| | | |
|---|---|---|
| *G01N 33/68* | (2006.01) | |
| *A61K 38/57* | (2006.01) | |
| *A61K 45/06* | (2006.01) | |
| *C07K 14/81* | (2006.01) | |
| *G01N 33/543* | (2006.01) | |

(52) U.S. Cl.
CPC ......... *G01N 33/6893* (2013.01); *A61K 38/57* (2013.01); *A61K 45/06* (2013.01); *C07K 14/81* (2013.01); *C07K 14/8114* (2013.01); *G01N 33/543* (2013.01); *G01N 2333/4704* (2013.01); *G01N 2800/7095* (2013.01)

(58) Field of Classification Search
CPC ............ G01N 33/6893; G01N 33/543; G01N 2333/4704; G01N 2800/7095; G01N 2800/50; G01N 2800/52; G01N 2800/56; A61K 38/57; A61K 45/06; A61K 38/00; C07K 14/81; C07K 14/8114; C07K 16/38; A61P 31/00; A61P 29/00
See application file for complete search history.

(56) References Cited

U.S. PATENT DOCUMENTS

| | | |
|---|---|---|
| 4,839,298 A | 6/1989 | Kay et al. |
| 5,166,133 A | 11/1992 | Houston et al. |
| 5,777,081 A | 7/1998 | Michalski et al. |

(Continued)

FOREIGN PATENT DOCUMENTS

| | | |
|---|---|---|
| CN | 1972961 A | 5/2007 |
| CN | 101160133 A | 4/2008 |

(Continued)

OTHER PUBLICATIONS

C. Mizon, M. Balduyck, D. Albani, C. Michalski, T. Bumouf, J. Mizon, Development of an enzyme-linked immunosorbent assay for human plasma inter-a-trypsin inhibitor ( ITI) using specific antibodies against each of the H 1 and H 2 heavy chains, 1996, Journal of Immunological Methods 190 ( 1996) 61-70 (Year: 1996).*

(Continued)

*Primary Examiner* — Ann Montgomery
*Assistant Examiner* — Chau N. B. Tran
(74) *Attorney, Agent, or Firm* — Clark & Elbing LLP

(57) ABSTRACT

Described herein are methods for quantifying IAIP levels in a sample.

20 Claims, 30 Drawing Sheets

(56) References Cited

U.S. PATENT DOCUMENTS

| | | | |
|---|---|---|---|
| 5,948,894 A | 9/1999 | Berry et al. | |
| 6,069,236 A | 5/2000 | Burnouf-Radosevich et al. | |
| 6,313,091 B1 | 11/2001 | Wisniewski et al. | |
| 6,489,128 B1 | 12/2002 | Lim et al. | |
| 6,660,482 B1* | 12/2003 | Lim | G01N 33/573 |
| | | | 435/7.1 |
| 6,673,908 B1 | 1/2004 | Stanton, Jr. | |
| 7,470,666 B2 | 12/2008 | Fu et al. | |
| 7,932,365 B2 | 4/2011 | Lim et al. | |
| 7,939,282 B2 | 5/2011 | Fast et al. | |
| 9,139,641 B2* | 9/2015 | Lim | A61P 31/00 |
| 9,505,814 B2 | 11/2016 | Bairstow et al. | |
| 9,572,872 B2 | 2/2017 | Lim et al. | |
| 9,758,570 B2* | 9/2017 | Lim | A61P 35/00 |
| 10,076,559 B2 | 9/2018 | Lim et al. | |
| 10,258,675 B2 | 4/2019 | Lim et al. | |
| RE47,972 E | 5/2020 | Lim et al. | |
| 2003/0027848 A1 | 2/2003 | Billotte et al. | |
| 2003/0149062 A1 | 8/2003 | Jung et al. | |
| 2003/0190732 A1 | 10/2003 | Josic | |
| 2004/0009212 A1 | 1/2004 | Tsai | |
| 2006/0079670 A1 | 4/2006 | Komatsoulis et al. | |
| 2006/0110774 A1 | 5/2006 | Fast et al. | |
| 2007/0160594 A1 | 7/2007 | Filvaroff et al. | |
| 2007/0172479 A1 | 7/2007 | Warne et al. | |
| 2007/0297982 A1 | 12/2007 | Lim et al. | |
| 2010/0285507 A1 | 11/2010 | Cho et al. | |
| 2011/0038917 A1 | 2/2011 | Kappers et al. | |
| 2011/0190194 A1 | 8/2011 | Lim et al. | |
| 2011/0190208 A1 | 8/2011 | Akerstrom et al. | |
| 2011/0236381 A1 | 9/2011 | Garantziotis et al. | |
| 2011/0293594 A1 | 12/2011 | Teschner et al. | |
| 2012/0028269 A1 | 2/2012 | Lim et al. | |
| 2012/0053113 A1 | 3/2012 | Bairstow et al. | |
| 2013/0274171 A1 | 10/2013 | Fiala et al. | |
| 2014/0206844 A1 | 7/2014 | Lim | |
| 2015/0166624 A1 | 6/2015 | Tseng et al. | |
| 2015/0361127 A1 | 12/2015 | Lim | |
| 2021/0393750 A1 | 12/2021 | Lim et al. | |
| 2023/0190894 A1 | 6/2023 | Lim et al. | |

FOREIGN PATENT DOCUMENTS

| | | |
|---|---|---|
| CN | 103889221 A | 6/2014 |
| CN | 104507309 A | 4/2015 |
| CN | 103142650 B | 5/2016 |
| EP | 0367090 A1 | 5/1990 |
| EP | 2664337 A1 | 11/2013 |
| JP | H09-503775 A | 4/1997 |
| JP | 2003-40775 A | 2/2003 |
| JP | 2003-292459 A | 10/2003 |
| JP | 2005-531521 A | 10/2005 |
| JP | 2006126216 * | 1/2006 |
| JP | 2006-126216 A | 5/2006 |
| JP | 2006-520390 A | 9/2006 |
| JP | 2007-515397 A | 6/2007 |
| JP | 2015-100316 A | 6/2015 |
| KR | 10-2011-0053404 A | 5/2011 |
| WO | WO-92/18160 A2 | 10/1992 |
| WO | WO-01/63280 A2 | 8/2001 |
| WO | WO-02/30983 A2 | 4/2002 |
| WO | WO-02/32406 A2 | 4/2002 |
| WO | WO-03/082247 A2 | 10/2003 |
| WO | WO-2004/082615 A2 | 9/2004 |
| WO | WO-2005/030252 A1 | 4/2005 |
| WO | WO-2005/046587 A2 | 5/2005 |
| WO | WO-2005/121163 A2 | 12/2005 |
| WO | WO-2007/038686 A2 | 4/2007 |
| WO | WO-2008/067655 A1 | 6/2008 |
| WO | WO-2009/154695 A1 | 12/2009 |
| WO | WO-2010/068308 A1 | 6/2010 |
| WO | WO-2014/039987 A2 | 3/2014 |
| WO | WO-2014/113659 A1 | 7/2014 |
| WO | WO-2015/071402 A1 | 5/2015 |
| WO | WO-2016/138476 A1 | 9/2016 |
| WO | WO-2018/053029 A1 | 3/2018 |
| WO | WO-2018/200722 A1 | 11/2018 |
| WO | WO-2020/086879 A1 | 4/2020 |
| WO | WO-2022/104282 A1 | 5/2022 |

OTHER PUBLICATIONS

C. Mizon, V. Queyrel, M. Balduyck, H. Drobecq, E. Hachulla and J. Mizon, Human pre-a-inhibitor is a positive acute-phase protein that is more susceptible than inter-a-inhibitor to proteolysis by stimulated neutrophils, European Journal of Clinical Investigation (2000) 30, 79-86 (Year: 2000).*

Salier JP, Rouet P, Raguenez G, Daveau M., The inter-alpha-inhibitor family: from structure to regulation. Biochem J. Apr. 1, 1996; 315 (Pt 1):1-9 (Year: 1996).*

Michalski et al (Preparation and properties of a therapeutic inter-alpha-trypsin inhibitor concentrate from human plasma, Vox Sang 1994;67(4):329-36) (Year: 1994).*

Pankhurst et al (Characterization of the heparin-binding properties of human clusterin, Biochemistry Apr. 7, 1998;37(14):4823-30)). (Year: 1998).*

Song et al (Metals in Protein-Protein Interfaces, 2014) (Year: 2014).*

Chaaban et al., "The role of inter-alpha inhibitor proteins in the diagnosis of neonatal sepsis," J Pediatr. 154(4):620-622.e1 (Apr. 2009) (4 pages).

Chaaban et al., "Inter-(alpha) inhibitor protein and its associated glycosaminoglycans protect against histone-induced injury," Blood. 125(14):2286-96 (Apr. 2015).

Zhang et al., "Constitutive expression of inter-alpha-inhibitor (Ialpha1) family proteins and tumor necrosis factor-stimulated gene-6 (TSG-6) by human amniotic membrane epithelial and stromal cells supporting formation of the heavy chain-hyaluronan (HC-HA) complex," J Biol Chem. 287(15):12433-44 (Apr. 2012).

Teiwes, Hanno, Thesis: "A Paper-Based Lateral Flow Device for the Detection of I(Alpha)IP Via Elisa," Master of Science, University of Rhode Island, 2014 (134 pages).

Ahmed et al., "Inhibition of allergic late airway responses by inhaled heparin-derived oligosaccharides," J Appl Physiol. 88(5):1721-9 (2000).

Ahmed et al., "Prevention of exercise-induced bronchoconstriction by inhaled low-molecular-weight heparin," Am J Respir Crit Care Med. 160(2):576-81 (1999).

Atmani et al., "Role of inter-alpha-inhibitor and its related proteins in urolithiasis. Purification of an inter-alpha-inhibitor related protein from the bovine kidney," Urol Res. 27(1):57-61 (1999).

Bogdan et al., "Tumor necrosis factor-alpha contributes to apoptosis in hippocampal neurons during experimental group B streptococcal meningitis," J Infect Dis. 176(3):693-7 (1997).

Bove, "Anaphylactic reaction to purified anti-hemophilic factor concentrate," Transfusion 28(6):603 (1988).

Bradding et al., "TNF alpha is localized to nasal mucosal mast cells and is released in acute allergic rhinitis," Clin Exp Allergy. 25(5):406-15 (1995) (Abstract only provided) (1 page).

Brass et al., "Chronic LPS inhalation causes emphysema-like changes in mouse lung that are associated with apoptosis," Am J Respir Cell Mol Biol. 39(5):584-90 (2008).

Burnouf, "Chromatography in plasma fractionation: benefits and future trends," J Chromatogr B Biomed Appl. 664(1):3-15 (1995).

Campo et al., "Molecular-weight-dependent effects of nonanticoagulant heparins on allergic airway responses," J Appl Physiol. 86(2):549-57 (1999).

Carrette et al., "Purification and characterization of pig inter-alpha-inhibitor and its constitutive heavy chains," Biochim Biophys Acta. 1338(1):21-30 (1997).

Cazzola et al., "Emerging anti-inflammatory strategies for COPD," Eur Respir J. 40(3):724-41 (2012).

Communication Pursuant to Article 94(3) and Rule 71(1) EPC in European Patent Application No. 04810367.5, dated Jun. 4, 2012 (2 pages).

(56) References Cited

OTHER PUBLICATIONS

Communication Pursuant to Article 94(3) EPC in European Patent Application No. 04810367.5, dated Jul. 1, 2013 (5 pages).
Communication Pursuant to Article 94(3) EPC in European Patent Application No. 04810367.5, dated May 23, 2014 (5 pages).
Communication Pursuant to Article 94(3) EPC in European Patent Application No. 09767008.7 dated Oct. 22, 2013 (7 pages).
Communication Pursuant to Article 94(3) EPC in European Patent Application No. 09767008.7, dated Apr. 28, 2016 (7 pages).
Communication Pursuant to Article 94(3) EPC for European Patent Application No. 09767008.7, dated Sep. 23, 2014 (6 pages).
Communication Pursuant to Rules 70(2) and 70a(2) EPC for European Patent Application No. 09767008.7, dated Aug. 12, 2011 (1 page).
Daveau et al., "Human inter-alpha-inhibitor family in inflammation: simultaneous synthesis of positive and negative acute-phase proteins," Biochem J. 292(Pt 2):485-92 (1993).
De la Motte et al., "Mononuclear leukocytes bind to specific hyaluronan structures on colon mucosal smooth muscle cells treated with polyinosinic acid:polycytidylic acid: inter-alpha-trypsin inhibitor is crucial to structure and function," Am J Pathol. 163(1):121-33 (2003).
Decision of Refusal for Japanese Patent Application No. 2011-511643, mailed Dec. 9, 2014 (4 pages).
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther. 328(3):758-65 (2009).
Enghild et al., "Analysis of inter-alpha-trypsin inhibitor and a novel trypsin inhibitor, pre-alpha-trypsin inhibitor, from human plasma. Polypeptide chain stoichiometry and assembly by glycan," J Biol Chem. 264(27):15975-81 (1989).
English Translation of Notification of Reason for Refusal in Japanese Patent Application No. 2011-511643, mailed on Nov. 12, 2013 (7 pages).
English Translation of Search Report for Chinese Patent Application No. 201210460374.2, dated Aug. 22, 2014 (3 pages).
English Translation of the Notification of Reason for Refusal for Japanese Patent Application No. 2015-080358, mailed Mar. 30, 2016 (5 pages).
EPO Communication pursuant to Rule 112(1) EPC for European Patent Application No. 09767008.7, dated Aug. 11, 2015 (3 pages).
Examination Report for Australian Patent Application No. 2009260822, issued Aug. 23, 2016 (3 pages).
Examination Report for Australian Patent Application No. 2009260822, issued Dec. 19, 2014 (4 pages).
Extended European Search Report for European Application No. EP 09767008.7, dated Jul. 26, 2011 (7 pages).
Feldmann et al., "Lasker Clinical Medical Research Award. TNF defined as a therapeutic target for rheumatoid arthritis and other autoimmune diseases," Nat Med. 9(10):1245-50, 1433 (2003).
First Office Action for Chinese Patent Application No. 200980129119.6, dated Apr. 7, 2013 (31 pages).
Fourth Office Action for Chinese Patent Application No. 200980129119.6, issued Jul. 30, 2015 (19 pages).
Fourth Office Action for Chinese Patent Application No. 201210460374.2, dated Aug. 25, 2015 (5 pages).
Garantziotis et al., "Inter-alpha-trypsin inhibitor attenuates complement activation and complement-induced lung injury," J Immunol. 179(6):4187-92 (2007) (7 pages).
Hamm et al., "Frequent expression loss of Inter-alpha-trypsin inhibitor heavy chain (ITIH) genes in multiple human solid tumors: a systematic expression analysis," BMC Cancer. 8:25 (2008) (15 pages).
Hoffer et al., "Improved virus safety and purity of a chromatographically produced Factor IX concentrate by nanofiltration," J Chromatogr B Biomed Appl. 669(2):187-96 (1995).

International Preliminary Report on Patentability and Written Opinion of the International Searching Authority for International Application No. PCT/US2009/003291, dated Nov. 30, 2010 (6 pages).
International Preliminary Report on Patentability and Written Opinion of the International Searching Authority for International Application No. PCT/US2013/058791, mailed Jun. 11, 2015 (7 pages).
International Preliminary Report on Patentability and Written Opinion of the International Searching Authority for International Application No. PCT/US2014/012033, mailed Jul. 30, 2015 (10 pages).
International Search Report and Written Opinion for International Application No. PCT/US2014/012033, mailed May 27, 2014 (14 pages).
International Search Report and Written Opinion for International Patent Application No. PCT/US2013/058791, mailed Jan. 10, 2014 (11 pages).
International Search Report for International Application No. PCT/US2004/036848, mailed Nov. 4, 2005 (5 pages).
International Search Report for International Application No. PCT/US2009/003291, mailed Aug. 24, 2009 (2 pages).
Ito et al., "A pilot randomized trial of a human anti-interleukin-6 receptor monoclonal antibody in active Crohn's disease," Gastroenterology. 126(4):989-96 (2004).
Iwasaki et al., "TNF-alpha contributes to the development of allergic rhinitis in mice," J Allergy Clin Immunol. 112(1):134-40 (2003).
Josic et al., "Proteomic characterization of inter-alpha inhibitor proteins from human plasma," Proteomics. 6(9):2874-85 (2006).
Katoh et al., "Galectin-9 inhibits CD44-hyaluronan interaction and suppresses a murine model of allergic asthma," Am J Respir Crit Care Med. 176(1):27-35 (2007).
Katz, "Advances in the medical therapy of inflammatory bowel disease," Curr Opin Gastroenterol. 18(4):435-40 (2002).
Koraka et al., "Plasma levels of inter-alpha inhibitor proteins in children with acute Dengue virus infection," PLoS One. 5(4):e9967 (2010) (4 pages).
Kricka, "Human anti-animal antibody interferences in immunological assays," Clin Chem. 45(7):942-956 (1999).
Lim et al., "Affinity purification and enzymatic cleavage of inter-alpha inhibitor proteins using antibody and elastase immobilized on CIM monolithic disks," J Chromatogr A. 1065(1):39-43 (2005).
Lim et al., "Correlation between mortality and the levels of inter-alpha inhibitors in the plasma of patients with severe sepsis," J Infect Dis. 188(6):919-26 (2003).
Lim, "Inter-alpha inhibitors: From laboratory to market," <http://www.brownenterpriseforum.org/matriarch/documents/Lim.pdf>, retrieved Jul. 13, 2011 (6 pages).
Ljung et al., "Infliximab in inflammatory bowel disease: clinical outcome in a population based cohort from Stockholm County," Gut. 53(6):849-53 (2004).
Martinez-Salas et al., "Inhibition of allergic airway responses by inhaled low-molecular-weight heparins: molecular-weight dependence," J Appl Physiol. 84(1):222-8 (1998).
McCann et al., "Evaluation of expanded bed adsorption chromatography for extraction of prothrombin complex from Cohn Supernatant I," Biologicals. 36(4):227-233 (2008).
MEGA- and GIGA preps of cosmid-, BAC-, PAC, YAC-, and P1-DNA with JETSTAR 2.0, Sep. 2005 (6 pages).
Michalski et al., "Preparation and properties of a therapeutic inter-alpha-trypsin inhibitor concentrate from human plasma," Vox Sang. 67(4):329-36 (1994).
Mihara et al., "IL-6/IL-6 receptor system and its role in physiological and pathological conditions," Clin Sci (Lond). 122(4):143-59 (2012).
Mizon et al., "Human pre-alpha-inhibitor: isolation from a by-product of industrial scale plasma fractionation and structural analysis of its H3 heavy chain," J Chromatogr B Biomed Sci Appl. 692(2):281-91 (1997).
Mo et al., "Anti-tumor necrosis factor-alpha treatment reduces allergic responses in an allergic rhinitis mouse model," Allergy. 66(2):279-86 (2011).
Molinari et al., "Inhibition of antigen-induced airway hyperresponsiveness by ultralow molecular-weight heparin," Am J Respir Crit Care Med. 157(3 Pt 1):887-93 (1998).

(56) References Cited

OTHER PUBLICATIONS

Notice of Preliminary Rejection for Korean Patent Application No. 10-2010-7029406, dated Oct. 30, 2015 (14 pages).
Odum, "Inter-alpha-Trypsin Inhibitor and Pre-alpha-Trypsin Inhibitor in Health and Disease: Determination by Immunoelectrophoresis and Immunoblotting," Biol. Chem. Hoppe-Seyler 371(12):1153-58 (1990).
Office Action for Canadian Patent Application No. 2544816, dated Dec. 30, 2013 (4 pages).
Office Action for Canadian Patent Application No. 2544816, dated Mar. 1, 2012 (7 pages).
Office Action for Canadian Patent Application No. 2544816, dated Oct. 20, 2014 (6 pages).
Office Action for Canadian Patent Application No. 2726281, dated Aug. 10, 2016 (4 pages).
Office Action for Canadian Patent Application No. 2726281, dated Jun. 30, 2015 (9 pages).
Office Action for Chinese Patent Application No. 201210460374.2, dated Jan. 24, 2014 (5 pages).
Opal et al., "Inter-alpha-inhibitor proteins are endogenous furin inhibitors and provide protection against experimental anthrax intoxication," Infect Immun. 73(8):5101-5 (2005).
Opal et al., "Longitudinal studies of inter-alpha inhibitor proteins in severely septic patients: a potential clinical marker and mediator of severe sepsis," Crit Care Med. 35(2):387-92 (2007).
Partial Supplementary European Search Report for European Application No. 14740523.7, dated Jun. 8, 2016 (7 pages).
Raoust et al., "Pseudomonas aeruginosa LPS or flagellin are sufficient to activate TLR-dependent signaling in murine alveolar macrophages and airway epithelial cells," PLoS One. 4(10):e7259 (2009) (9 pages).
Rutgeerts et al., "Optimizing anti-TNF treatment in inflammatory bowel disease," Gastroenterology. 126(6):1593-610 (2004).
Salier et al., "Inter-alpha-trypsin-inhibitor (ITI): use of immunoadsorbents for preparation of anti-ITI antiserum, ITI-free human serum and purified ITI," J Immunol Methods. 47(2):239-48 (1981).
Salier et al., "Purification of the human serum inter-alpha-trypsin inhibitor by zinc chelate and hydrophobic interaction chromatographies," Anal Biochem. 109(2):273-83 (1980).
Sanon et al., "Peripheral arterial ischemic events in cancer patients," Vasc Med. 16(2):119-30 (2011).
Saukkonen et al., "The role of cytokines in the generation of inflammation and tissue damage in experimental gram-positive meningitis," J Exp Med. 171(2):439-48 (1990).
Second Office Action for Chinese Patent Application No. 200980129119.6, issued Feb. 20, 2014 (19 pages).
Second Office Action for Chinese Patent Application No. 201210460374.2, dated Aug. 22, 2014 (11 pages).
Sin et al., "Chronic obstructive pulmonary disease as a risk factor for cardiovascular morbidity and mortality," Proc Am Thorac Soc. 2(1):8-11 (2005).
Singh et al., "Inter-alpha inhibitor protein administration improves survival from neonatal sepsis in mice," Pediatr Res. 68(3):242-7 (2010).
Su et al., "Role of CFTR expressed by neutrophils in modulating acute lung inflammation and injury in mice," Inflamm Res. 60(7):619-32 (2011).
Supplementary European Search Report for European Patent Application No. 04810367, dated Jan. 18, 2010 (7 pages).
Sykes et al., "Treatment of severe autoimmune disease by stem-cell transplantation," Nature. 435(7042):620-7 (2005).
Takeuchi et al., "Baseline tumour necrosis factor alpha levels predict the necessity for dose escalation of infliximab therapy in patients with rheumatoid arthritis," Ann Rheum Dis. 70(7):1208-15 (2011) (8 pages).
Tanaka et al., "Targeting interleukin-6: all the way to treat autoimmune and inflammatory diseases," Int J Biol Sci. 8(9):1227-36 (2012).
Tarner et al., "Treatment of autoimmune disease by adoptive cellular gene therapy," Ann NY Acad Sci. 998:512-9 (2003).
Third Office Action for Chinese Patent Application No. 200980129119.6, issued Nov. 15, 2014 (21 pages).
Third Office Action for Chinese Patent Application No. 201210460374.2, dated Apr. 2, 2015 (5 pages).
Trefz et al., "Establishment of an enzyme-linked immuno-sorbent assay for urinary trypsin inhibitor by using a monoclonal antibody," J Immunoassay. 12(3):347-69 (1991) (15 pages).
Triantaphyllopoulos et al., "A model of chronic inflammation and pulmonary emphysema after multiple ozone exposures in mice," Am J Physiol Lung Cell Mol Physiol. 300(5):L691-700 (2011).
Van Heel et al., "Inflammatory bowel disease is associated with a TNF polymorphism that affects an interaction between the OCT1 and NF(-kappa)B transcription factors," Hum Mol Genet. 11(11):1281-9 (2002).
Verhein et al., "IL-1 receptors mediate persistent, but not acute, airway hyperreactivity to ozone in guinea pigs," Am J Respir Cell Mol Biol. 39(6):730-8 (2008).
Wu et al., "Delayed administration of human inter-alpha inhibitor proteins reduces mortality in sepsis," Crit Care Med. 32(8):1747-52 (2004).
Yang et al., "Administration of human inter-alpha-inhibitors maintains hemodynamic stability and improves survival during sepsis," Crit Care Med. 30(3):617-22 (2002).
Zhuo et al., "Defect in SHAP-hyaluronan complex causes severe female infertility. A study by inactivation of the bikunin gene in mice," J Biol Chem. 276(11):7693-6 (2001) (5 pages).
Zosky et al., "Animal models of asthma," Clin Exp Allergy. 37(7):973-88 (2007) (17 pages).
Kuus-Reichel et al., "Will immunogenicity limit the use, efficacy, and future development of therapeutic monoclonal antibodies?" Clin Diagn Lab Immunol. 1(4):365-72 (1994).
Mascelli et al., "Molecular, biologic, and pharmacokinetic properties of monoclonal antibodies: impact of these parameters on early clinical development," J Clin Pharmacol. 47(5):553-65 (2007).
Carter, "Potent antibody therapeutics by design," Nature Rev Immunol. 6(5):343-57 (2006).
Fries et al., "Inter-alpha-inhibitor, hyaluronan and inflammation," Acta Biochim Pol. 50(3):735-42 (2003).
ProThera Biologics, "Inter-alpha Inhibitor Proteins (IAIP): Protein Replacement Therapy to Treat Systemic Inflammation," Oct. 2010, retrieved from <http://www.ri-bizplan.com/Portals/0/Uploads/Documents/Resources/ProThera.pdf> (12 pages).
Jourdain et al., "Effects of Inter-alpha-inhibitor in Experimental Endotoxic Shock and Disseminated Intravascular Coagulation," Am J Respir Crit Care Med. 156(6):1825-33 (1997).
Baek et al., "Inter-alpha Inhibitor Proteins in Infants and Decreased Levels in Neonatal Sepsis," J Pediatr. 143(1):11-5 (2003).
Wu et al., "Delayed administration of human inter-alpha-inhibitor (IaI) reduces mortality in sepsis," Critical Care. 197(3S):S41 (2003) (Abstract Only).
International Search Report and Written Opinion for International Application No. PCT/US17/51403, mailed Jan. 23, 2018 (24 pages).
International Preliminary Report on Patentability for International Application No. PCT/US17/51403, mailed Mar. 28, 2019 (16 pages).
Ge et al., "Effect observation of ulinastatin combined with high does ambroxol in the treatment of patients with severe pneumonia," J Clin Pul Med 18(1):63-64 (2013) (4 pages).
Leng et al., "Ulinastatin for Acute Lung Injury and Acute Respiratory Distress Syndrome: A Systematic Review and Meta-Analysis," World J Crit Care Med 3(1):34-41 (2014) (9 Pages).
Emmett et al., "Protein Abnormalities in Adult Respiratory Distress Syndrome, Tuberculosis, and Cystic Fibrosis Sera," Proc Soc Exp Biol Med 184(1):74-82 (1987).
Adair et al., "Inter-alpha-trypsin Inhibitor Promotes Bronchial Epithelial Repair After Injury Through Vitronectin Binding," J Biol Chem 284(25):16922-16930 (2009).
Garantziotis et al., "Serum Inter-Alpha-Trypsin Inhibitor and Matrix Hyaluronan Promote Angiogenesis in Fibrotic Lung Injury," Am J Respir Crit Care Med 178(9):939-47(2008).
Shah et al., "Blood Level of Inter-Alpha Inhibitor Proteins Distinguishes Necrotizing Enterocolitis From Spontaneous Intestinal Per-

(56) References Cited

OTHER PUBLICATIONS foration," available in PMC Jan. 1, 2018, published as final edited form as: J Pediatr 180:135-140 (Jan. 2017) (16 pages).
Invitation to Pay Additional Fees for International Application No. PCT/US2019/057911, dated Dec. 26, 2019 (3 pages).
International Search Report and Written Opinion for International Application No. PCT/US2019/057911, dated Feb. 21, 2020 (29 pages).
International Search Report and Written Opinion for International Application No. PCT/US18/29436, mailed Aug. 31, 2018 (19 pages).
Wark, "DX-890 (Dyax)," IDrugs. 5(6):586-9 (Jun. 2002).
Rui et al., "Urinary trypsin inhibitor attenuates seawater-induced acute lung injury by influencing the activities of nuclear factor-kappaB and its related inflammatory mediators," Respiration. 83(4):335-43 (Dec. 2011).
Mizon et al., "Development of an enzyme-linked immunosorbent assay for human plasma inter-alpha-trypsin inhibitor (ITI) using specific antibodies against each of the H1 and H2 heavy chains." J Immuno Methods. 190:61-70 (Mar. 1996).
Rucevic et al., "Altered levels and molecular forms of granzyme K in plasma from septic patients." SHOCK 27(5):488-493 (May 2007).
International Search Report and Written Opinion for PCT/US2021/059569, dated Mar. 30, 2022 (15 pages).
Extended European Search Report for European Application No. EP 19876409.4, dated Aug. 3, 2022 (22 pages).
International Preliminary Report on Patentability and Written Opinion of the International Searching Authority for International Application No. PCT/US2021/059569, issued May 16, 2023 (7 pages).
English Translation of Second Office Action for Chinese Patent Application No. 201880027257.2, issued Jul. 26, 2023 (7pages).
English Translation of Office Action for Israeli Patent Application No. 270069, dated Jun. 7, 2023 (6 pages).
Communication Pursuant to Article 94(3) EPC in European Patent Application No. 19876409.4, dated Jun. 27, 2023 (15 pages).
English Translation of Office Action for Japanese Patent Application No. 2021-523071, dated Sep. 4, 2023 (3 pages).
Herrmann K. and Carroll K., "An Exclusively Human Milk Diet Reduces Necrotizing Enterocolitis," Breastfeeding Medicine. 9(4):184-190 (2014) (7 Pages).
Opstelten et al., "Dairy Products, Dietary Calcium, and Risk of Inflammatory Bowel Disease: Results From a European Prospective Cohort Investigation," Inflamm Bowel Dis. 22(6):1403-1411 (Jun. 2016) (9 pages).
Kanwar et al., "Comparative activities of milk components in reversing chronic colitis," J. Dairy Sci. 99(4):2488-2501 (Apr. 2016) (14 pages).
Communication Pursuant to Article 94(3) EPC in European Patent Application No. 19876409.4, dated Feb. 1, 2024 (5 pages).
Radmacher et al., "Milk as a Vehicle for Oral Medications: Hidden Osmoles," J. Perinatology 32:227-229 (2012) (4 pages).
Threlkeld et al., "Effects of inter-alpha inhibitor proteins on neonatal brain injury: Age, task and treatment dependent neurobehavioral outcomes," Experimental Neurology 261:424-433 (Jul. 2014) (10 pages).
Spasova et al., "Ischemia Reduces Inter-Alpha Inhibitor Proteins in the Brain of the Ovine Fetus," available in PMC Jun. 1, 2018. Published in final form as Dev Neurobiol. 77(6):726-737 (Jun. 2017) (19 pages).
Muheem et al., "A review on the strategies for oral delivery of proteins and peptides and their clinical perspectives," Saudi Pharmaceutical Journal 24:413-428 (Jun. 2014) (16 pages).
Htwe et al., "Inter-[alpha] inhibitor proteins maintain neutrophils in a resting state by regulating shape and reducing ROS production," Blood Adv. 2(15):1923-34 (Aug. 2018).
Hatayama et al., "High-mobility group box-1 and inter-alpha inhibitor proteins: In vitro binding and co-localization in cerebral cortex after hypoxic-ischemic injury," FASEB J. 35(3):e21399 (Mar. 2021) (16 pages).
Shorr et al., "Methicillin-resistant Staphylococcus aureus prolongs intensive care unit stay in ventilator-associated pneumonia, despite initially appropriate antibiotic therapy," Crit Care Med. 34(3):700-6 (Mar. 2006) (7 pages).
Ender and Dolan, "Pneumonia associated with near-drowning," Clin Infect Dis. 25(4):896-907 (Oct. 1997) (12 pages).
McCullough et al., "Exogenous inter-a inhibitor proteins prevent cell death and improve ischemic stroke outcomes in mice," J Clin Invest. 131(17):e144898 (Sep. 2021) (18 pages).

\* cited by examiner

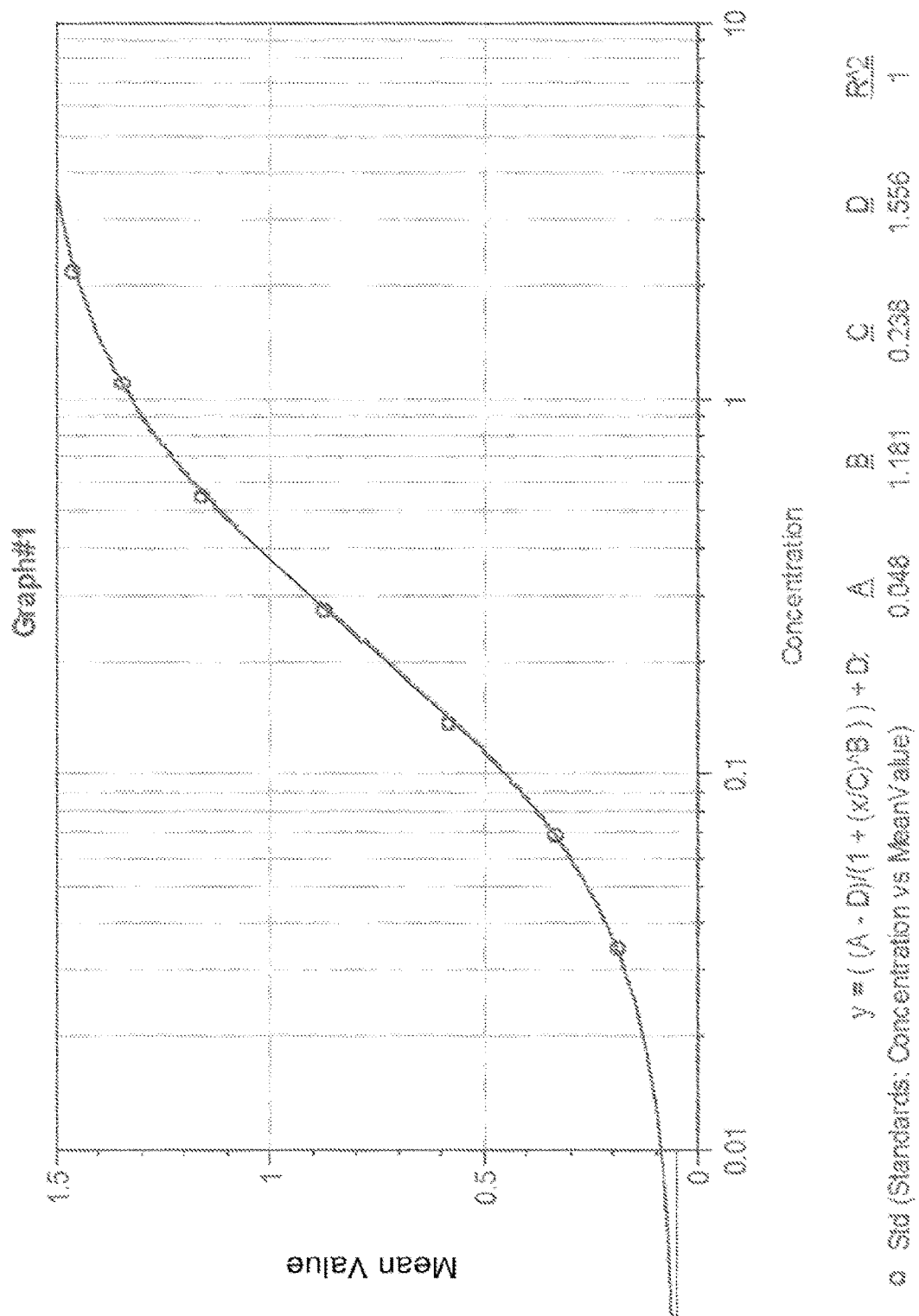
FIG. 3C Endotoxin-IAIP Standard Curve

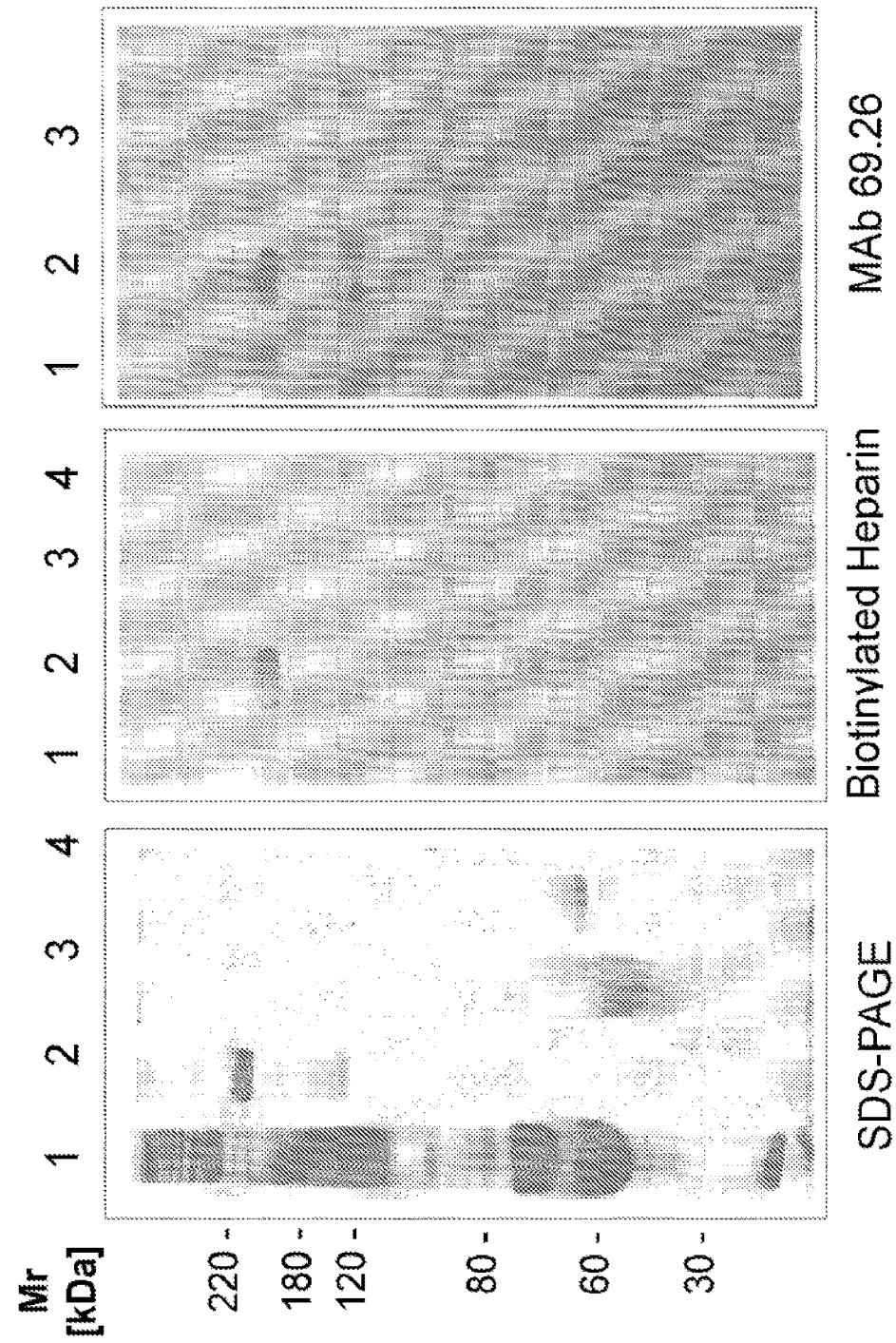

INTER-ALPHA INHIBITOR PROTEINS

BACKGROUND

IAIP (Inter alpha Inhibitor Proteins) are a family of naturally occurring, immunomodulatory plasma proteins that circulate in high concentrations in the blood of all mammals. IAIP are primarily produced in the liver, released into the blood and a subunit (bikunin) is excreted in the urine. IAIP have an important role in modulating inflammation. They have extensive protective effects toward the serious inflammation caused by infection, trauma, and injury and importantly, the protective effects of IAIP are independent from the causative microbial agents or triggers. Members of this family are composed of heavy and light polypeptide subunits that are covalently linked by glycosaminoglycan. IAIP can be found in vivo as Inter-alpha-Inhibitor (I$\alpha$I), a 250 kDa molecule composed of two heavy chains (H1 & H2) and a single light chain (L), and Pre-alpha-Inhibitor (P$\alpha$I), a 125 kDa molecule composed of one heavy (H3) and one light chain (L).

When the body generates inflammatory signals, such as those elicited during injury or infection, IAIP traffic into the tissues and directly reach sites of inflammation. The heavy chains of IAIP enhance the anti-inflammatory response by binding to proteins which are part of the inflammatory cascade. Also, when the heavy chains are cleaved, the light chain with its associated GAG (named Bikunin due to its two Kunitz domains) is released and the serine protease inhibitory activity of the light chain is activated. Bikunin inhibits the activity of serine proteases such as trypsin, elastase, plasmin, cathepsin G, and furin. IAIP exert their anti-inflammatory effects through multiple mechanisms. They have been shown to bind proteins that amplify inflammation, such as complement and extracellular histones (Damage Signals), thus attenuating inflammatory processes. Through the heavy chains, IAIP can bind the extra cellular matrix (ECM) proteins and have been shown to promote lung epithelial repair after injury in both in vitro and in vivo models. IAIP have also been shown in multiple in vivo models to down regulate inflammatory cytokines, such as TNF-$\alpha$ and IL-6. Bikunin-deficient (and therefore IAIP deficient) mice have been shown to have decreased inflammatory markers of cell adhesion, VCAM-1 and ICAM-1.

In healthy individuals, the amount of circulating IAIP in blood is relatively high (between 400-800 mg/L). However, IAIP levels rapidly decrease during systemic inflammation/sepsis in newborns and in adult patients (Baek Y W, et al. J Pediatr. 2003; 143:11-15; Lim Y P, et al. J Infect Dis. 2003; 188:919-926 and Opal S M, et al. Crit Care Med. 2007; 35:387-392), and decreased levels of IAIP have been shown to correlate strongly with disease progression. As diseases progress to more advanced and life-threatening stages, IAIP levels drop precipitously, suggesting that IAIP has clinical utility as a prognostic and theranostic marker in assisting clinicians in monitoring disease progression and making informed treatment decisions for diseases such as severe inflammatory diseases such as severe pneumonia, sepsis and the associated organ damage, NEC, wound healing, burn, cancer, stroke, Alzheimer's disease, epilepsy and others.

A standardized competitive IAIP immunoassay has been used to measure IAIP in over blood samples from patients with systemic inflammation following bacterial and viral infections. The competitive IAIP immunoassay provides a measure of IAIP that detects only the light chain, therefore both intact IAIP and cleaved bikunin are detected in this assay. The competitive assay does not detect the other crucial parts of IAIP which are very important for its anti-inflammatory and tissues repair properties; namely the heavy chains and the glycosaminoglycan. Thus, the competitive IAIP immunoassay has limitations in assessment of active IAIP in a patient sample. Given the importance of IAIP as a crucial component of the body's protective innate immune defenses and its potential use as a prognostic biomarker, there exists a need for improved methods to quantitatively measure IAIP. An ideal assay would measure both the light chain and heavy chain subunits to capture the complete molecule.

SUMMARY OF THE INVENTION

The present invention provides methods for quantifying IAIP in a sample from a subject through direct detection with agents that bind to and detect IAIP (e.g., agents that bind to intact IAIP, a heavy chain of IAIP, or a glycosaminoglycan (GAG) of IAIP). The methods of quantification can be used to evaluate, diagnose, treat, or monitor subjects, or to evaluate disease severity or treatment efficacy in a subject. The invention also features kits that can be used to quantify IAIP according to the methods described herein.

In a first aspect, featured is a method for quantifying inter-alpha inhibitor protein (IAIP) in a sample from a subject by: a) contacting the sample with a binding agent to produce an IAIP-binding agent complex, wherein the binding agent is bound to a support; b) contacting the IAIP-binding agent complex with a detection agent; and c) detecting an amount of the detection agent bound to the IAIP-binding agent complex to quantify IAIP in the sample.

In some embodiments, the IAIP is intact IAIP.

In some embodiments, the binding agent is an IAIP ligand that binds to IAIP. In some embodiments, the binding agent is an antibody that specifically binds to IAIP.

In some embodiments, the detection agent is or contains an IAIP ligand. In some embodiments, the detection agent further contains an antibody that binds to the IAIP ligand detection agent (e.g., an IAIP ligand). In some embodiments, the detection agent is an antibody that specifically binds to IAIP. For example, in particular embodiments, the binding agent is an antibody that specifically binds to IAIP (e.g., MAb 69.26 or MAb 69.31) and the detection agent is or contains an IAIP ligand that binds to IAIP (e.g., heparin, hyaluronic acid, endotoxin (LPS), or a histone). In other embodiments, the binding agent is an an IAIP ligand that binds to IAIP (e.g., heparin, hyaluronic acid, LPS, or a histone) and the detection agent is an antibody that specifically binds to IAIP (e.g., MAb 69.26 or MAb 69.31).

In some embodiments, the IAIP is in an IAIP-IAIP ligand complex.

In some embodiments, the binding agent is an IAIP ligand that binds to IAIP. In some embodiments, the IAIP ligand of the IAIP-IAIP ligand complex is different from the binding agent. In some embodiments, the binding agent is an antibody that binds to the IAIP ligand of the IAIP-IAIP ligand complex. In some embodiments, the binding agent is an antibody that specifically binds to IAIP of the IAIP-IAIP ligand complex.

In some embodiments, the detection agent contains an IAIP ligand that binds to IAIP. In some embodiments, the detection agent further contains an antibody that binds to the IAIP ligand detection agent. In some embodiments, the IAIP ligand of the IAIP-IAIP ligand complex is different from the IAIP ligand detection agent. In some embodiments, the detection agent is an antibody that binds to the IAIP ligand of the IAIP-IAIP ligand complex. In some embodiments, the detection agent is an antibody that specifically binds to IAIP of the IAIP-IAIP ligand complex.

In some embodiments, the antibody is a monoclonal antibody. In some embodiments, the antibody is MAb 69.26 or MAb 69.31.

In some embodiments, the IAIP ligand is selected from the group consisting of endotoxin (LPS), heparin, a histone, hyaluronic acid, vitronectin, fibronectin, laminin, tenascin C, aggrecan, von Willebrand Factor, pentraxin-3 (PTX3), TNF-stimulated gene-6 (TSG-6), factor IX, a complement component, factor XIIIa, and tissue transglutaminase. In some embodiments, the complement component is C1q, C2, C3, C4, C5, C6, C8, properdin, or factor D.

In some embodiments, the detection agent contains a label. In some embodiments, the label is biotin, an enzyme, an enzyme substrate, a radiolabel, a luminescent compound, colloidal gold, a particle, or a fluorescent dye.

In some embodiments, the support is a plate, a particle, a nanoparticle, a resin, a membrane, a biochip, a container, a test strip, or a bead.

In some embodiments, the method further includes a wash step between steps a) and b).

In some embodiments, the method further includes a wash step between steps b) and c).

In some embodiments, the method further includes a blocking step prior to step a) or step b).

In some embodiments, the contacting in step a) and/or b) is performed at a pH of about 7.0 to about 3.5. In some embodiments, the pH is about 5.0 to about 3.5. In some embodiments, the pH is about 4.0.

In some embodiments, the sample is a fluid. In some embodiments, the fluid is blood, plasma, serum, urine, cerebrospinal fluid, synovial fluid, amniotic fluid, interstitial fluid, follicular fluid, peritoneal fluid, bronchoalveolar lavage fluid, breast milk, sputum, lymph, bile, or tissue homogenate.

In some embodiments, the subject is a human subject. In some embodiments, the subject has been identified as having or at risk of developing an inflammatory disease or condition or an infection. In some embodiments, the subject has not been identified as having or at risk of developing an inflammatory disease or condition or an infection. In some embodiments, the method is performed before, after, or concurrent with diagnosis of the subject as having or at risk of an inflammatory disease or condition or an infection. In some embodiments, the method is performed substantially concurrent with treatment of the subject for an inflammatory disease or condition or an infection. In some embodiments, the method is performed prior to treatment of the subject for an inflammatory disease or condition or an infection. In some embodiments, the method is performed after treatment of the subject for an inflammatory disease or condition or an infection.

In some embodiments, the inflammatory disease or condition is selected from the group consisting of sepsis, septic shock, sterile sepsis, trauma, injury, stroke, acute inflammatory disease, SIRS, acute lung injury, ARDS, pneumonia, necrotizing enterocolitis, acute pancreatitis, renal disease, acute kidney injury, liver injury, acute circulatory failure, preeclampsia, cancer, cancer metastasis, tumor invasion, peripheral artery disease, type 1 or type 2 diabetes, atherosclerotic cardiovascular disease, intermittent claudication, critical limb ischemic disease, myocardial infarction, carotid occlusion, umbilical cord occlusion, low birth-weight, premature birth, surgery-induced inflammation, abscess-induced inflammation, multiple sclerosis, pulmonary insufficiency, peripheral neuropathy, hypoxic ischemia, bacterial infection, wounds, burns, lacerations, contusions, bone fractures, surgical procedures, tissue ischemia, rheumatoid arthritis, meningitis, inflammatory bowel disease, chronic obstructive pulmonary disease, rhinitis, preterm labor, or an infectious disease.

In some embodiments, the infection is caused by a gram negative bacteria, such as *Neisseria* species including *Neisseria gonorrhoeae* and *Neisseria meningitidis*, *Branhamella* species including *Branhamella catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*, *Brucella* species, *Yersinia* species including *Yersinia pestis* and *Yersinia enterocolitica*, *Francisella* species including *Francisella tularensis*, *Pasturella* species including *Pasteurella multocida*, *Vibrio cholerae*, *Flavobacterium* species, *meningosepticum*, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, and *Legionella* species including *Legionella pneumophila*.

In some embodiments, the subject is a neonate, a child, an adolescent, or an adult.

In some embodiments, the method is performed one or more times per year. In some embodiments, the method is performed one or more times per month. In some embodiments, the method is performed one or more times per week. In some embodiments, the method is performed one or more times per day. In some embodiments, the method is performed one or more times per hour.

In some embodiments, the method is performed at least once, at least twice, at least three times, at least five times, or at least ten times.

In some embodiments, the method further includes administering a treatment comprising IAIP or a therapeutic agent to the subject. In some embodiments, the subject has an IAIP concentration of 200 µg/mL or lower. In some embodiments, the sample from the subject has an elevated level of IAIP-IAIP ligand complex relative to a reference sample. In some embodiments, the subject has or is at risk of developing an inflammatory disease or condition or an infection.

In some embodiments, the method includes administering IAIP and a therapeutic agent to the subject.

In some embodiments, the therapeutic agent is selected from the group consisting of an antibiotic agent, an antiviral agent, an antifungal agent, an antiparasitic agent, an anti-inflammatory agent, an anti-cancer agent, an anti-coagulant, an immunomodulatory agent, a bronchodilator agent, a complement inhibitor, a vasopressor, a sedative, or mechanical ventilation.

In some embodiments, the subject has been ill for at least one day. In some embodiments, the subject has been ill for at least one week. In some embodiments, the subject has been ill for at least one month. In some embodiments, the subject has been ill for at least one year.

In some embodiments, the method is for: a) evaluating the health status of the subject; b) monitoring the health status of the subject; c) diagnosing the subject as having or being at risk for an inflammatory disease or condition or an infection; d) evaluating efficacy of a treatment administered to the subject; or e) evaluating disease severity in the subject.

In some embodiments, the method further includes comparing the amount of IAIP and/or an IAIP-IAIP ligand complex detected in the sample to the amount of IAIP and/or an IAIP-IAIP ligand complex found in a sample from a normal subject or to a cutoff value. In some embodiments, an amount of IAIP in the sample that is lower than an amount of IAIP in the sample from the normal subject or relative to the cutoff value indicates that the subject has or is at risk of developing an inflammatory disease or condition or an infection. In some embodiments, an amount of an IAIP-IAIP ligand complex in the sample that is greater than an amount of IAIP-IAIP ligand complex in the sample from the normal subject or relative to the cutoff value indicates that the subject has or is at risk of developing an inflammatory disease or condition or an infection. In some embodiments, the amount of IAIP in the sample from the normal subject, or the cutoff value, is >250 µg/mL. In some embodiments, the amount of IAIP in the sample from the normal subject is about 260 to about 540 µg/mL.

In some embodiments, a determination that the subject has an IAIP concentration of 250 µg/mL or less indicates that the subject has or is at high risk of developing an inflammatory disease or condition or an infection or is diagnosed as having an increased risk of morbidity and/or mortality.

In some embodiments, the subject has an IAIP concentration of 200 to 300 µg/mL. In other embodiments the method is performed at least once a year, at least twice a year, at least once a month, at least once a week, at least once a day, or at least once an hour.

In some embodiments, the subject previously had an inflammatory disease or condition or an infection.

In some embodiments, the method is performed prior to the treatment and/or one or more times during the course of the treatment. In some embodiments, the method is performed after initiation of the treatment and/or after conclusion of the treatment. In some embodiments, the treatment is determined to be effective if the concentration of IAIP increases in the subject relative to a prior measurement of IAIP in the subject and/or if the concentration of an IAIP-IAIP ligand complex decreases in the subject relative to a prior measurement of an IAIP-IAIP ligand complex in the subject. In some embodiments, the treatment is determined to be ineffective if the concentration of IAIP decreases or remains constant in the subject relative to a prior measurement of IAIP in the subject and/or if the concentration of an IAIP-IAIP ligand complex increases or remains constant in the subject relative to a prior measurement of an IAIP-IAIP ligand complex in the subject. In some embodiments, the method further comprises modifying or changing the treatment.

In a second aspect, featured is a method of treating a subject (e.g., a human, such as a neonate, a child, an adolescent, or an adult) that has or is at risk of developing an inflammatory disease or infection, in which the subject has been determined to be in need of treatment according to the method of the first aspect, by administering to the subject a therapeutically effective amount of IAIP and/or a therapeutic agent selected from the group consisting of an antibiotic agent, an antiviral agent, an antifungal agent, an antiparasitic agent, an anti-inflammatory agent, an anticancer agent, an anti-coagulant, an immunomodulatory agent, a bronchodilator agent, a complement inhibitor, a vasopressor, a sedative, or mechanical ventilation.

In some embodiments, the inflammatory disease or condition is selected from the group consisting of sepsis, septic shock, sterile sepsis, trauma, injury, stroke, acute inflammatory disease, SIRS, acute lung injury, ARDS, pneumonia, necrotizing enterocolitis, acute pancreatitis, renal disease, acute kidney injury, liver injury, acute circulatory failure, surgery-induced inflammation, abscess-induced inflammation, multiple sclerosis, preeclampsia, cancer, cancer metastasis, tumor invasion, peripheral artery disease, type 1 or type 2 diabetes, atherosclerotic cardiovascular disease, intermittent claudication, critical limb ischemic disease, myocardial infarction, carotid occlusion, umbilical cord occlusion, low birth-weight, premature birth, pulmonary insufficiency, peripheral neuropathy, hypoxic ischemia, bacterial infection, wounds, burns, lacerations, contusions, bone fractures, surgical procedures, tissue ischemia, rheumatoid arthritis, meningitis, inflammatory bowel disease, chronic obstructive pulmonary disease, rhinitis, preterm labor, or an infectious disease.

In some embodiments, the infection is caused by a gram negative bacteria, such as *Neisseria* species including *Neisseria gonorrhoeae* and *Neisseria meningitidis, Branhamella* species including *Branhamella catarrhalis, Escherichia* species including *Escherichia coli, Enterobacter* species, *Proteus* species including *Proteus mirabilis, Pseudomonas* species including *Pseudomonas aeruginosa, Pseudomonas mallei*, and *Pseudomonas pseudomallei, Klebsiella* species including *Klebsiella pneumoniae, Salmonella* species, *Shigella* species, *Serratia* species, *Acinetobacter* species; *Haemophilus* species including *Haemophilus influenzae* and *Haemophilus ducreyi, Brucella* species, *Yersinia* species including *Yersinia pestis* and *Yersinia enterocolitica, Francisella* species including *Francisella tularensis, Pasteurella* species including *Pasteurella multocida, Vibrio cholerae, Flavobacterium* species, *meningosepticum, Campylobacter* species including *Campylobacter jejuni, Bacteroides* species (oral, pharyngeal) including *Bacteroides fragilis, Fusobacterium* species including *Fusobacterium nucleatum, Calymmatobacterium granulomatis, Streptobacillus* species including *Streptobacillus moniliformis*, and *Legionella* species including *Legionella pneumophila*.

In a third aspect, featured is a kit for quantifying IAIP or an IAIP-IAIP ligand complex in a sample, in which the kit comprises an IAIP binding agent and an IAIP detection agent and, optionally, one or more of the following: a wash buffer, a blocking agent, a substrate for detection of a label, and instructions for quantifying a level of IAIP or an IAIP-IAIP ligand complex in a sample. One or more of the components of the kit may be provided in a container, such as a tube or vial, and/or in a form ready for use (e.g., application to a support of the kit (e.g., a plate or test strip).

In some embodiments, the binding agent is immobilized on a support.

In some embodiments, the detection agent is labeled.

In some embodiments, the IAIP binding agent is an IAIP-specific antibody or an IAIP ligand.

In some embodiments, the kit further contains an IAIP ligand binding agent. In some embodiments, the IAIP ligand binding agent is an antibody that binds to an IAIP ligand.

In some embodiments, the IAIP detection agent is an IAIP-specific antibody or an IAIP ligand.

In some embodiments, the kit further contains an IAIP ligand detection agent. In some embodiments, the IAIP ligand detection agent is an antibody that binds specifically to an IAIP ligand.

In some embodiments, the IAIP-specific antibody is a monoclonal antibody. In some embodiments, the monoclonal antibody is MAb 69.26 or MAb 69.31.

In some embodiments, the support is a plate, a resin, a container, a membrane, a biochip, a particle, a nanoparticle, a test strip, or a bead.

In some embodiments, the label is an enzyme, an enzyme substrate, biotin, a particle, a fluorescent dye, a luminescent compound, or a radiolabel.

In some embodiments, the IAIP ligand is selected from the group consisting of endotoxin (LPS), heparin, a histone, hyaluronic acid, laminin, tenascin C, aggrecan, vitronectin, fibronectin, von Willebrand Factor, pentraxin-3 (PTX3), TNF-stimulated gene-6 (TSG-6), factor IX, a complement component, factor XIIIa, and tissue transglutaminase.

Definitions

As used herein, the term "about" refers to a value that is no more than 10% above or below the value being described. For example, the term "about 5 nM" indicates a range of from 4.5 nM to 5.5 nM.

As used herein, "administration" refers to providing or giving a subject a therapeutic agent (e.g., IAIP), by any effective route. Exemplary routes of administration are described herein below.

As used herein, the term "antibody" (Ab) refers to an immunoglobulin molecule that specifically binds to, or is immunologically reactive with, a particular antigen, and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab')2, Fd, Fvs, single-chain Fvs (scFv), rIgG, single-chain antibodies, disulfide-linked Fvs (sdFv), fragments comprising either a $V_L$ or $V_H$ domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')2 fragments) that are capable of specifically binding to a target protein. Fab and F(ab')2 fragments lack the Fc fragment of an intact antibody, clear more rapidly from the circulation of the animal, and may have less non-specific tissue binding than an intact antibody.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be a Fab, F(ab')2, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546, 1989), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single-chain Fv (scFv); see, e.g., Bird et al., Science 242: 423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the term "inter-alpha inhibitor proteins" or "IAIPs" refers to large, multi-component glycoproteins in a family of structurally related immunomodulatory proteins. IAIPs have been shown to be important in the inhibition of an array of proteases including neutrophil elastase, plasmin, trypsin, chymotrypsin, Granzyme K, preprotein convertase, furin, cathepsin G, and acrosin. IAIP exert a broad range of anti-inflammatory mechanisms, in addition to serine protease inhibitory activity, such as binding to and inactivating complement, extracellular histones, and coagulation factors, down regulating pro-inflammatory cytokines such as TNF-α and IL-6, down regulating adhesion factors such as VCAM and ICAM, and down regulating NFkB. IAIP are also importantly involved in promoting protection and repair of tissues where the heavy chains are transferred to matrix proteins to promote cellular migration and proliferation. In human plasma, IAIPs are found at relatively high concentrations (400-800 mg/L). Unlike other inhibitor molecules, this family of inhibitors typically includes a combination of polypeptide chains (light and heavy chains) covalently linked by a chondroitin sulfate chain. The heavy chains of IAIPs (H1, H2, and H3) are also called hyaluronic acid (HA) binding proteins. The major forms of IAIPs found in human plasma are inter-alpha-inhibitor (IαI), which contains two heavy chains (H1 and H2) and a single light chain (L), and pre-alpha-inhibitor (PαI), which contains one heavy (H3) and one light chain (L). Another IAIP is the light chain (also termed bikunin (bi-kunitz inhibitor) with two Kunitz domains), bound to the glycosaminoglycan, which is known to broadly inhibit plasma and tissue serine proteases. Another IAIP is the heavy chain-related molecule H4, which circulates in the blood without linkage to bikunin. Yet another IAIP is the heavy chain-related molecule H5. IαI and PαI present in the plasma fraction have an apparent molecular weight of between about 60 kDa to about 280 kDa.

As used herein, the term "IAIP ligand" refers to a molecule or a fragment thereof that binds to IAIP in vivo or in vitro (e.g., endotoxin (LPS), heparin, a histone, hyaluronic acid, matricellular proteins (e.g., vitronectin, fibronectin, tenascin C, laminin, aggrecan), von Willebrand Factor, pentraxin-3 (PTX3), TNF-stimulated gene-6 (TSG-6), coagulation factors (e.g., factor IX and factor XIIIa), a complement component, divalent cations such as $Ca^{2+}$, and tissue transglutaminase). IAIP ligands also include molecules that are predicted to bind to IAIP based on domain structure (e.g., proteins with RGD domains that would bind to the von Willebrand factor A domain of the IAIP heavy chains). The IAIP ligands for use in the methods described herein include ligands that bind to the heavy chain of IAIP, to the IAIP complex, or to the GAG of IAIP (e.g., ligands that do not bind solely to bikunin).

As used herein, the term "IAIP-specific antibody" or "antibody that specifically binds to IAIP" refers to any protein or peptide-containing molecule that includes at least a portion of an immunoglobulin molecule, such as at least one complementarity determining region (CDR) of a heavy or light chain or a ligand binding portion thereof, a heavy chain or light chain variable region, a heavy chain or light chain constant region, a framework region, or any portion thereof, that is capable of binding IAIP and that does not specifically bind to any other protein. An antibody that binds specifically to IAIP will bind to IAIP and provide a signal that is it least twice the background signal or noise, and more typically more than 10 to 100 times background.

As used herein, the term "monoclonal antibody" refers to an antibody that is derived from a single clone, including any eukaryotic, prokaryotic, or phage clone, and not the method by which it is produced.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof. The composition is, for example, indicated for human use (e.g., according to drug or biologic regulatory guidelines, such as those promulgated by the F.D.A. and/or the E.M.A.).

As used herein, the term "pharmaceutically acceptable" refers to those compounds, materials, compositions and/or dosage forms, that are suitable for contact with the tissues of a subject, such as a mammal (e.g., a human) without excessive toxicity, irritation, allergic response, and other problem complications commensurate with a reasonable benefit/risk ratio.

As used herein, the phrase "reducing the likelihood of developing" refers to prophylactic treatment of a patient (e.g., a human) who is susceptible to, or otherwise at risk of, a particular disease, syndrome, or condition (e.g., the conditions described herein, such as an inflammatory disease or an infection)) or is at risk of an increase in the degree or severity of a current disease, syndrome, or condition, for example, a patient having community acquired pneumonia (CAP) who is at risk of progressing to severe community acquired pneumonia (sCAP).

As used herein, the term "reference" refers to a parameter (e.g., protein level, concentration, nucleic acid expression level, and gene copy number) of a sample or standard that is used for comparison purposes to the parameter in a test sample. For example, a reference sample can be obtained from a healthy individual (e.g., an individual who does not have an inflammatory disease or infection). A reference level can be the level (or an average thereof) of expression or concentration of an analyte (e.g., protein (e.g., an IAIP), nucleic acid, carbohydrate, etc.) determined from one or more reference samples. For example, the reference can be an average level of an analyte (e.g., IAIP) (e.g., a mean level or median level) among a plurality of individuals (e.g., healthy individuals, or individuals who do not have an inflammatory disease or infection). In other instances, a reference level can be a predetermined threshold level, e.g., based on level or concentration of an analyte as otherwise determined, e.g., by empirical assays.

As used herein, the term "sample" refers to a specimen (e.g., blood, blood component (e.g., serum or plasma), urine, saliva, amniotic fluid, lung lavage, cerebrospinal fluid, tissue (e.g., tissue biopsy or tissue homogenate), pancreatic fluid, synovial fluid, and cells) isolated from a subject (e.g., a mammal, such as a human).

As used herein, the phrase "specifically binds" refers to a binding reaction which is determinative of the presence of an analyte (e.g., a protein, such as IAIP) in a heterogeneous population of proteins and other biological molecules. The analyte may be an antigen that is recognized, e.g., by an antibody or antigen-binding fragment thereof. Specific binding between an analyte to be measured and a binding agent (e.g., an antibody or antigen-binding fragment or ligand) exhibits a $K_D$ of less than 100 nM. For example, an antibody or antigen-binding fragment thereof that specifically binds to an antigen (e.g., IAIP) binds to the antigen with a $K_D$ of up to 100 nM (e.g., between 1 pM and 100 nM). An antibody or antigen-binding fragment thereof that does not exhibit specific binding to a particular antigen or epitope thereof (e.g., IAIP) exhibits a $K_D$ of greater than 100 nM (e.g., greater than 500 nm, 1 µM, 100 µM, 500 µM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As used herein, the term "sepsis" refers to a systemic response to an infection (referred to herein as "infectious sepsis") or to a non-infectious process associated with acute tissue injury and innate immune activation (referred to interchangeably herein as "sterile inflammation" or "sterile sepsis"), which can lead to tissue damage, organ failure, and death. Infectious sepsis can result from an infection caused by bacteria, viruses, fungi, or other microorganisms such as parasites (e.g., protozoan parasites). Sterile sepsis can occur after hemorrhagic shock, polytrauma, pancreatitis, transplant rejection, autoimmune disease, inorganic compounds, crystals, chemicals, or ischemia/reperfusion and is not associated with the presence of a known infection.

As used herein, the term "subject" refers to a mammal, including, but not limited to, a human or non-human mammal, such as a primate, bovine, equine, porcine, ovine, feline, or canine. The subject may be a patient.

As used herein, the term "treating" refers to reducing or ameliorating a disorder and/or symptoms associated therewith. It will be appreciated that, although not precluded, treating a disorder or condition does not require that the disorder or symptoms associated therewith be completely eliminated.

BRIEF DESCRIPTION OF THE DRAWINGS

FIGS. 3B and 3C are graphs showing standard curves for heparin-IAIP and endotoxin (LPS)-IAIP sandwich-type ELISAs, respectively. This assay provides a direct measure of IAIP concentration, with increasing signal indicating higher amounts of IAIP in the sample.

FIG. 7 is a series of blots showing the binding of heparin and an IAIP-specific antibody (MAb 69.26) to IAIP. As shown in the middle blot, biotinylated heparin bound to purified IAIP (250 kDa IαI and 125 kDa PαI), but did not bind to the IAIP light chain, bikunin, or to the negative control human serum albumin. In contrast, MAb 69.26 bound to both purified IAIP and bikunin. These data suggest that heparin binds to the heavy chain of IAIP, which may lead to a more accurate measure of circulating, intact IAIP in the heparin-IAIP ELISA.

As shown in FIG. 8A, the competitive ELISA yielded an average IAIP concentration of 246 μg/mL in patients with severe pneumonia, 250 μg/mL in patients with severe sepsis, and 330 μg/mL in healthy controls, and found significant differences between IAIP levels in subjects with severe pneumonia and healthy controls, but not between subjects with severe sepsis and healthy controls. As shown in FIG. 8B, the LPS-IAIP ELISA yielded an average IAIP concentration of 141 μg/mL in patients with severe pneumonia, 150 μg/mL in patients with severe sepsis, and 338 μg/mL in healthy controls, and found significant differences between IAIP levels in subjects with severe pneumonia or severe sepsis and healthy controls. As shown in FIG. 8C, the heparin-IAIP ELISA yielded an average IAIP concentration of 145 μg/mL in patients with severe pneumonia, 193 μg/mL in patients with severe sepsis, and 422 μg/mL in healthy controls, and found significant differences between IAIP levels in subjects with severe pneumonia or severe sepsis and healthy controls. The LPS-IAIP ELISA performed comparably to the heparin-IAIP ELISA in terms of having increased sensitivity and providing more statistically significant results compared to the competitive ELISA.

DETAILED DESCRIPTION

Figure 1:
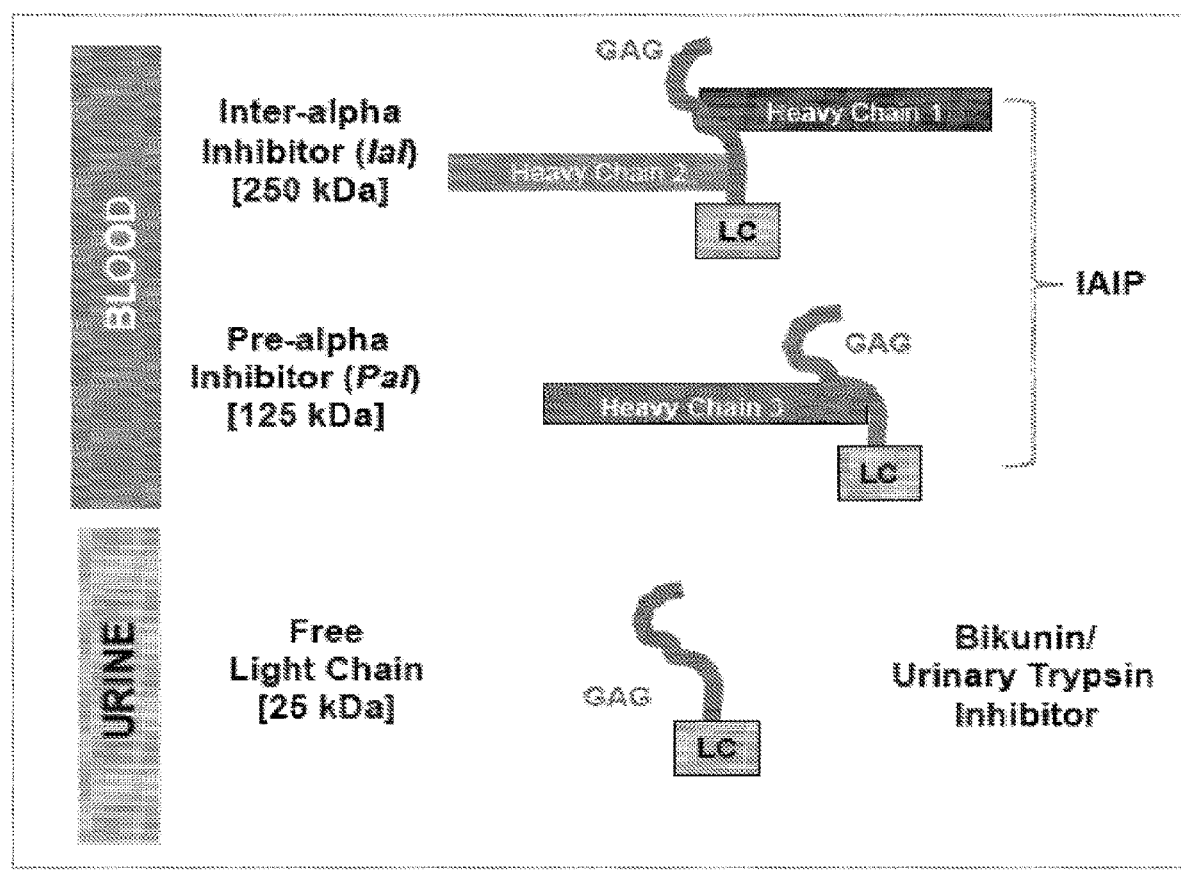
FIG. 1 is a schematic depicting the structure of circulating (e.g., in blood) IAIP (IaI and PaI) and free light chain (LC, bikunin), for example, excreted in urine. Heavy and light chains of IAIP are uniquely linked by glycosaminoglycan (GAG).

Featured are methods of measuring IAIP concentration in a sample (e.g., a sample from a subject, such as a blood sample) using a reagent that can be used to measure the amount of IAIP in the sample (e.g., a reagent that directly binds to IAIP in the sample, such an IAIP ligand, or a reagent that binds to an IAIP ligand that is bound to IAIP). The reagent can be measured by using a detectable label. The methods can be used to identify subjects having or at risk of developing an inflammatory disease or condition or an infection, to determine a health status of or disease severity in a subject, and to monitor treatment of a condition in a subject (e.g., an inflammatory disease or condition or an infection) administered a therapeutic agent (e.g., IAIP or an agent for treating an inflammatory disease or condition or an infection).

Assays for Quantification of IAIP

Provided are methods of quantifying IAIP in a sample(s) collected from a subject. Previous methods of detecting IAIP relied on antibody-based competitive ELISAs, which provide an indirect measure of IAIP concentration in a sample. This method detects both intact IAIP complexes (e.g., IAIP containing one or more heavy chains (H1-H5) and the light chain, bikunin) and bikunin alone. In contrast, the methods described herein use a reagent (e.g., an IAIP ligand) that detects IAIP in the sample directly by binding to an IAIP heavy chain, a heavy and light chain of an intact IAIP complex, or a GAG of an IAIP complex, but do not bind bikunin alone.

Without wishing to be bound by theory, the IAIP ligand-based assays described herein exhibit greater sensitivity and robustness than a competitive ELISA due to the detection of the IAIP heavy chain or intact IAIP complexes. The present methods provide an improved readout of the amount of functional IAIP in a sample relative to antibody-based assays that detect cleaved or degraded IAIP light chain.

The methods described herein include the use of an IAIP ligand to detect IAIP, e.g., IAIP captured on a substrate (e.g., a solid support, e.g., a plate, a resin, a particle, a container, a membrane, or a bead), using, e.g., an IAIP-specific agent, such as an antibody, the use of an IAIP ligand to capture IAIP for subsequent detection with an IAIP-specific antibody, and the use of an IAIP ligand to capture IAIP for subsequent detection with a second, different IAIP ligand.

A first method that can be used to detect intact IAIP in a sample involves an IAIP binding agent (e.g., an IAIP-specific antibody or an IAIP ligand) that is attached to a support and used to capture IAIP in the sample. An IAIP detection agent (e.g., an IAIP ligand or an IAIP-specific antibody) is then added that binds to the IAIP that has formed a complex with the IAIP binding agent. IAIP concentration can then be quantified, e.g., by detecting the presence of a label, which is either attached directly to the IAIP detection agent or is attached to a reagent that binds to the IAIP detection agent.

A second method that can be used to detect an amount of IAIP in a sample involves detecting IAIP-IAIP ligand complexes that have formed in vivo and that are present in the sample. This method also begins with the use of a binding agent that is attached to a support. The binding agent can bind to either IAIP or the IAIP ligand. A detection agent is then added, which binds to the other component of the IAIP-IAIP ligand complex (e.g., if the binding agent is directed to IAIP, the detection agent is directed to the IAIP ligand, and, conversely, if the binding agent is directed to the IAIP ligand, the detection agent is directed to IAIP). The concentration of the IAIP can then be measured, e.g., by detecting the presence of a label, which is either attached directly or indirectly to the detection agent.

The reagents used in the methods and the method steps are discussed in detail below.

IAIP Ligands

IAIP ligands for use in the methods described herein include ligands that bind to one or more IAIP heavy chains, to an IAIP heavy chain(s) and the light chain, bikunin (e.g., intact IAIP), or to a GAG of IAIP (e.g., a GAG in intact IAIP). Intact IAIP is a complex that contains at least one IAIP heavy chain (H1, H2, H3, H4, and/or H5) and the IAIP light chain (bikunin). Any ligand that binds to a heavy chain of IAIP or intact IAIP can be used in the methods described herein, including, e.g., endotoxin (lipopolysaccharide, LPS), heparin, histone, hyaluronic acid, vitronectin, fibronectin, tenascin C, laminin, aggrecan, von Willebrand Factor, pentraxin-3 (PTX3), TNF-stimulated gene-6 (TSG-6), coagulation proteins (e.g., factor IX and factor XIIIa), complement proteins (e.g., C1q, C2, C3, C4, C5, C6, C8, properdin, and factor D), divalent cations (e.g., $Ca^{2+}$), and tissue transglutaminase. IAIP ligands can be labeled according to standard techniques known in the art (e.g., using one or more of the detectable labels described below).

IAIP Antibodies

Antibodies that specifically bind to IAIP can be used as binding agents or detection agents in the methods described herein. Antibodies that specifically bind to IAIP are antibodies or antigen binding fragments thereof that do not specifically bind to any proteins other than IAIP (e.g., interaction of an IAIP-specific antibody with non-IAIP proteins yields a signal similar to background). The antibody that binds specifically to IAIP can bind to a heavy chain of IAIP, the light chain of IAIP, or both, or to a GAG of IAIP. Preferably, the antibody binds to a heavy chain of IAIP or to an intact IAIP containing heavy and light chains. The antibody may be raised against human IAIP, or against IAIP from another mammal (e.g., non-human primate, cow, pig, sheep, goat, cat, dog, rat, mouse, rabbit, guinea pig, or any other non-human mammal that expresses IAIP). The antibody that binds specifically to IAIP may bind only human IAIP, or may be capable of binding IAIP from humans and other mammals. The antibody can be produced by immunization of an animal typically used to generate antibodies with IAIP (e.g., rabbit, guinea pig, rat, mouse, sheep, donkey, goat, hamster, and chicken). The IAIP-specific antibody can be polyclonal (e.g., PAb R16, PAb R20, PAb R21), monoclonal (e.g., MAb 69.26 or MAb 69.31), chimeric, or recombinant.

Labels

Labels for detecting the concentration of IAIP in the methods described herein can be attached or conjugated to IAIP ligands, IAIP-specific antibodies, or to other reagents described herein. Labels suitable for detection of IAIP ligands, IAIP ligand-specific antibodies, and/or IAIP-specific antibodies include biotin, enzymes (e.g., horseradish peroxidase (HRP), alkaline phosphatase (AP), β-galactosidase, acetylcholinesterase, and catalase), enzyme substrates, radiolabels (e.g., radioisotopes), luminescent compounds, particles (e.g., colloidal gold (e.g., gold nanoparticles), a magnetic particle, or a latex particle) and fluorescent dyes. The label can then be assessed directly (e.g., through imaging of fluorescent dyes, detection of radioactivity, or detection of particles), through the use of enzyme-conjugated avidin or streptavidin (e.g., avidin or streptavidin conjugated to AP or HRP for detection of biotin), and/or through use of a substrate, and can be visualized by known methods and devices, including, e.g., a spectrophotometer, fluorometer, luminometer, or liquid scintillation counter. Substrates may be colorimetric (e.g., PNPP for detecting AP; or ABTS, OPD, or TMB for detecting HRP), chemiluminescent, or fluorescent. Substrates also include liquid scintillators for detection of radioactivity. Standard detection methods known in the art can be used to detect the labels described herein.

Samples

The methods described herein can be performed using a sample from a subject (e.g., a human subject). Suitable samples include fluid samples. For example, IAIP can be measured in a sample of blood or plasma from a subject (e.g., a subject with an inflammatory disease or condition, such as sepsis, or a subject at risk for developing an inflammatory disease or condition, such as sepsis). The methods described herein can also be performed using a sample of other bodily fluids, such as urine, cerebrospinal fluid, synovial fluid, amniotic fluid, interstitial fluid, follicular fluid, peritoneal fluid, bronchoalveolar lavage fluid, breast milk, sputum, lymph, and bile. Tissue samples (e.g., biopsies) from a subject can be homogenized in an appropriate buffer to create a "fluid" for quantification of IAIP using these methods.

The volume of sample used in the assay will vary depending on the type of assay being performed (e.g., an ELISA, a lateral flow immunoassay, or another assay) and the support (e.g., a plate, a membrane, a test strip, or another support). The volume of sample used can be from about 1 μL to about 500 μL (e.g., from about 1 μL to about 150 μL, e.g., from 1 μL to about 30 μL for an assay such as a lateral flow immunoassay, or from about 50 μL to about 200 μL for an assay such as an ELISA). The sample can be diluted before use in the assay with a buffer that will not interfere with binding to the binding or detection agent (e.g., water, PBS, or a buffer used in the methods of the assay), and may be diluted 1:2, 1:3, 1:4, 1:5, 1:10, 1:15, 1:20, 1:100 or more.

Method for Detecting Intact IAIP

A first IAIP quantification assay involves contacting a sample containing IAIP to an IAIP binding agent (e.g., an antibody that specifically binds to IAIP or an IAIP ligand) to form an IAIP-binding agent complex. The IAIP binding agent may be attached to a support (e.g., a solid support). Suitable supports include plates (e.g., multi-well plates), particles (e.g., magnetic particles, nanoparticles, magnetic nanoparticles), biochips, resins, membranes (e.g., nitrocellulose membranes, PVDF membranes), containers (e.g., tubes), test strips (e.g., cellulose, glass fiber, nitrocellulose), and beads (e.g., protein A or protein G beads, magnetic beads, glass beads, plastic beads). The support is preferably capable of being washed one or more times (e.g., using a buffer, such as TBS, TBS-T, PBS, or PBS-T) to remove material that does not bind to the IAIP binding agent.

The IAIP-binding agent complex is then contacted with an IAIP detection agent (e.g., an IAIP ligand or an antibody that specifically binds to IAIP). The IAIP detection agent may be conjugated to a label (e.g., one or more of the labels described above), which can then be detected using known detection methods. Alternatively, the IAIP detection agent can be directly detected without the use of a label. After the addition of the IAIP detection agent, an additional wash step (e.g., one or more) can be performed to remove unbound detection agent.

IAIP can then be measured based on signal from the conjugated label or the attached detection agent (e.g., enzyme activity or fluorescence) using standard techniques known in the art. If an enzyme is used as the label, substrate can be added to produce the signal (for example, a color change) and can be read by a device suitable for detecting the signal, such as a spectrophotometer. The signal (for example, absorbance or fluorescence) can be plotted against a standard with known concentration of IAIP to establish a standard curve or can be compared against a known reference concentration. The unknown concentration in the samples can be calculated and determined based on the established standard curve or reference concentration value.

Before the addition of the sample to the IAIP binding agent, a blocking step can be performed to prevent or reduce non-specific binding. Blocking agents for use in the methods described herein include, e.g., milk, BSA, casein, gelatin (e.g., fish gelatin), and serum (e.g., goat serum, donkey serum, horse serum, fetal bovine serum), among others.

The method steps can be performed at a pH of 7.0 to 3.5 (e.g., pH 5.0 to pH 3.5, e.g., pH 4.0). For example, either or both of the binding step and the detection step can be performed at a pH of 7.0 to 3.5 (e.g., pH 5.0 to pH 3.5, e.g., pH 4.0). The IAIP binding agent can be prepared in a buffer with a pH of 7.0 to 3.5 (e.g., pH 5.0 to pH 3.5, e.g., pH 4.0) and/or the IAIP detection agent (e.g., the IAIP ligand) can be prepared in a buffer with a pH of 7.0 to 3.5 (e.g., pH 5.0 to pH 3.5, e.g., pH 4.0). A low pH buffer (e.g., pH of 5.0 or lower, e.g., pH 4.0) can be used to improve detection of IAIP.

Also, to stabilize IAIP during the assay, divalent cations (e.g., $Ca^{2+}$, $Mg^{2+}$, $Mn^{2+}$, $Fe^{2+}$, etc.) may be added to the sample before or during contact with the IAIP binding agent, and/or added to the buffer containing the detection agent before or during contact with the binding agent-IAIP complex. Divalent cations can be provided in a concentration of 1 μM to 1 M (e.g., 100 μM to 100 mM, 1 mM to 10 mM).

a) IAIP-Specific Antibody Binding Agent and IAIP Ligand Detection Agent

In one example of the method described herein, the IAIP binding agent is an antibody that binds specifically to IAIP (e.g., MAb 69.26 or MAb 69.31) and the detection agent is a labeled IAIP ligand (e.g., heparin, hyaluronic acid, or LPS). Alternatively, the ligand can be unlabeled and detected using a labeled antibody that is specific for the IAIP ligand, or the unlabeled ligand can be detected using an unlabeled antibody that is specific for the IAIP ligand, which is then detected using a labeled secondary antibody (e.g., a labeled secondary antibody that binds to the antibody that is specific for the IAIP ligand but does not bind to the IAIP antibody, e.g., the IAIP antibody and the IAIP ligand antibody are generated in different host species). If the ligand is unlabeled and detected through the use of a labeled ligand-specific antibody, or a ligand-specific antibody and a labeled secondary antibody, additional wash steps may be performed before and/or after incubation with each antibody.

b) IAIP Ligand Binding Agent and IAIP-Specific Antibody Detection Agent

In another example of the method described herein, the IAIP binding agent is an IAIP ligand (e.g., heparin, hyaluronic acid, or LPS), and the detection agent is an antibody that is specific for IAIP (e.g., MAb 69.26 or MAb 69.31). In this example, the antibody that is specific for IAIP can be conjugated directly to a label, or the antibody can be detected using a labeled secondary antibody that binds to the IAIP-specific antibody. If a labeled secondary antibody is used, a wash step can be performed after incubation with the secondary antibody to minimize non-specific signal prior to IAIP measurement.

c) IAIP Ligand Binding Agent and IAIP Ligand Detection Agent

In a third example of the method described herein, the binding agent is an IAIP ligand (e.g., hyaluronic acid), and the detection agent is a labeled IAIP ligand that binds to a different region of IAIP (e.g., heparin, hyaluronic acid, or LPS). This method can be performed with any two IAIP ligands that do not bind to the same region of IAIP (e.g., two IAIP ligands that do not compete for binding to IAIP or for which the binding of one of the IAIP ligands does not sterically hinder the binding of the second IAIP ligand to IAIP). The ligand that acts as the IAIP detection agent can be unlabeled and detected using a labeled antibody that is specific for the IAIP ligand that acts as the detection agent, or it can be detected by a labeled secondary antibody that binds to an unlabeled antibody that is specific for the IAIP ligand that acts as the detection agent. If labeled antibodies are used for detection of the IAIP ligand that acts as the detection agent, additional wash steps may be performed before and/or after incubation with each antibody.

d) IAIP-Specific Antibody Binding Agent and IAIP-Specific Antibody Detection Agent In a fourth example of the method described herein, the binding agent is an IAIP-specific antibody and the detection agent is a labeled IAIP-specific antibody. In this example, at least one of the IAIP-specific antibodies is capable of binding to either intact IAIP or IAIP that includes at least one heavy chain (e.g., the antibody does not bind to bikunin unless at least one IAIP heavy chain is present, e.g., the antibody does not bind to cleaved or degraded IAIP lacking bikunin). Also, the two IAIP-specific antibodies used in the assay bind different epitopes of IAIP (e.g., the antibodies do not compete for binding to IAIP). If the two IAIP-specific antibodies are generated using different host species, then the IAIP-specific antibody used as the detection agent may be unlabeled and detected using a labeled secondary antibody. If a labeled secondary antibody is used, additional wash steps may be performed before and/or after incubation with the labeled secondary antibody.

e) Quantification of IAIP Using a Rapid Lateral-Flow Immunoassay (LFIA)

In a fifth example, the methods described herein can be performed using a lateral-flow immunoassay-based test. In this example, a small volume of a sample (e.g., 1-30 μL, e.g., 15 μL) can be applied to a test strip (e.g., a cellulose, glass fiber, or nitrocellulose) in an undiluted form or in a diluted form (e.g., diluted 1:2, 1:5, 1:10, 1:20, 1:100 or more, e.g., with a buffer (e.g., PBS) or water) and a buffer is then added to push the sample through the strip. The strip contains an IAIP binding agent (e.g., an IAIP-specific antibody or an IAIP ligand) to bind to IAIP in the sample. IAIP can be detected using an IAIP detection agent (e.g., a labeled IAIP-specific antibody or a labeled IAIP ligand), which can be added to the strip before, after, or concurrent with the addition of the sample. The test strip can be read using an appropriate reader for quantification of the label attached to the IAIP detection agent (e.g., a portable tabletop lateral flow reader, a handled PDA-based reader, or a smartphone/tablet based reader, among others). The selection of the binding and detection agent combination can be made based on the parameters outlined herein. This assay can be performed quickly (e.g., in 15 minutes or less, such as 15, 10, or 7 minutes or less) and provides a quantitative and rapid measurement of IAIP in a small sample volume.

Detection of Naturally Occurring IAIP-IAIP Ligand Complexes

Also provided are methods for detecting naturally occurring IAIP-IAIP ligand complexes (e.g., IAIP-IAIP ligand complexes that have formed in vivo in a subject (e.g., a human subject) and that are present in a sample from the subject). This method involves contacting a sample (e.g., a fluid sample, such as plasma, serum, blood, bronchoalveolar fluid, cerebrospinal fluid, sputum, urine or other bodily fluids) to a binding agent, e.g., a binding agent that is attached to a support (e.g., a solid support). The binding agent can be an IAIP binding agent (e.g., an antibody that specifically binds to IAIP, for example, MAb 69.26 or MAb 69.31, or an IAIP ligand), or the binding agent can be an antibody that specifically binds to the IAIP ligand of interest (e.g., the IAIP ligand that is suspected to have formed an IAIP-IAIP ligand complex in vivo). Suitable supports include plates (e.g., multi-well plates), particles (e.g., magnetic particles, nanoparticles, magnetic nanoparticles), biochips, resins, containers (e.g., tubes), membranes (e.g., nitrocellulose membranes, PVDF membranes), test strips (e.g., cellulose, glass fiber, or nitrocellulose) and beads (e.g., protein A or protein G beads, magnetic beads, glass beads, plastic beads). The support is preferably capable of being washed one or more times (e.g., using a buffer, such as TBS, TBS-T, PBS, or PBS-T) to remove material that does not bind to the binding agent.

If the binding agent used in the assay is an IAIP binding agent (e.g., an antibody that specifically binds to IAIP, for example, MAb 69.26 or MAb 69.31, or an IAIP ligand), the IAIP-IAIP ligand complex can be detected using a detection agent that is an antibody directed against the IAIP ligand of interest by contacting the antibody to the IAIP complex-binding agent complex. If the binding agent used in the assay is an antibody that specifically binds to the IAIP ligand of interest, the IAIP-IAIP ligand complex can be detected using a detection agent that specifically binds to IAIP (e.g., an antibody that specifically binds to IAIP, for example, MAb 69.26 or MAb 69.31, or a different IAIP ligand) by contacting the detection agent to the IAIP complex-binding agent complex.

A wash step (e.g., one or more) can be performed after incubation with the detection agent. Also, before the addition of the sample to the IAIP or IAIP ligand binding agent, a blocking step can be performed to prevent or reduce non-specific binding. Blocking agents for use in the methods described herein include, e.g., milk, BSA, casein, gelatin (e.g., fish gelatin), and serum (e.g., goat serum, donkey serum, horse serum, fetal bovine serum), among others.

If the detection agent is an antibody (e.g., an IAIP-specific antibody or an IAIP ligand-specific antibody), the detection agent can be directly conjugated to a label (e.g., a label described above), or the detection agent may be visualized by adding a labeled secondary antibody that does not bind to any other antibody used in the assay (e.g., the binding agent, if an antibody).

If the detection agent is a ligand (e.g., an IAIP ligand, such as a different IAIP ligand than that being detected in the assay), the detection agent can be directly conjugated to a label (e.g., a label described above), or detected using a labeled ligand-specific antibody, which is then detected. Alternatively, the detection agent can be detected using an unlabeled ligand-specific antibody and a labeled secondary antibody that does not bind to any other antibody used in the assay (e.g., the binding agent, if an antibody). If the detection agent is unlabeled and additional reagents (e.g., labeled primary or secondary antibodies) are used, one or more wash steps may be performed after incubation with the additional reagents to minimize non-specific signal. The label can be used to measure the concentration of the IAIP-IAIP ligand complex using the same substrates and imaging methods mentioned above. The signal from the sample can be compared to signal measured in sample(s) with a known concentration of the IAIP-IAIP ligand complex (e.g., to establish a standard curve). The unknown concentration in the samples can be calculated based on an established standard curve or based on a known reference concentration value.

If the identity of the IAIP ligand in the IAIP-IAIP ligand complex is unknown, the method can be performed using an antibody that specifically binds to IAIP (e.g., an antibody that binds to intact IAIP and/or an IAIP heavy chain) as the binding agent. The detection step can then be performed by adding labeled secondary antibodies specific to different IAIP ligands, washing after incubation with the labeled secondary antibodies, and detecting signal from the label to determine the identity of the IAIP ligand in the IAIP-IAIP ligand complex. Labeled antibodies can be added and evaluated individually for IAIP ligand identification, or they can be added simultaneously if different labels are attached or conjugated to each antibody (e.g., different fluorescent dyes). Once the IAIP ligand is identified, the amount of the IAIP-IAIP ligand complex in the sample can be quantified as described herein.

Quantification of IAIP Captured in the Assays

IAIP or an IAIP-IAIP ligand complex can be quantified by performing the detection methods described herein using a sample of interest alongside samples containing known amounts of IAIP or an IAIP-IAIP ligand complex that are used to create a standard curve. The sample from the subject can be measured at the same time as the known amounts of IAIP or an IAIP-IAIP ligand complex so that the concentration of IAIP or an IAIP-IAIP ligand complex in the sample can be determined. The concentration in the sample from the subject can be compared to an average concentration of IAIP or an IAIP-IAIP ligand complex measured using the same assay in a control population, such as healthy controls, to determine whether the concentration of IAIP in the sample falls within a normal range, or diseased controls, to determine whether the concentration of IAIP in the sample falls within a range for the disease state.

IAIP or IAIP-IAIP ligand complex concentration in a sample from a subject can also be compared to IAIP or IAIP-IAIP ligand complex concentration in a healthy control by measuring IAIP or an IAIP-IAIP ligand complex in both the test sample and the control sample at the same time using the methods described herein. Control samples include those that are derived from the same source material (e.g., both the test sample and the control sample are derived from the same bodily fluid or the same tissue type). In addition to being derived from the same source material, the test sample and control sample can also be collected from subjects of the same age and/or same sex to minimize possible variation between subjects. If IAIP concentrations are directly compared between a subject and a healthy control, a decrease in IAIP concentration in the subject of 25% or more compared to the healthy control would indicate that the subject has or is at risk of developing an inflammatory disease or condition or an infection.

Alternatively, IAIP or IAIP-IAIP ligand complex concentration in a sample from a subject can be compared to a predetermined cutoff value for the concentration of IAIP or IAIP-IAIP ligand complex under known conditions (e.g., a healthy state or a disease state). The cutoff value may be an average concentration of IAIP or IAIP-IAIP ligand complex determined from a population of normal subjects or disease subjects.

Using the methods described herein, healthy control subjects have been found to have 400±140 µg/mL IAIP in plasma, although higher concentrations have also been observed in healthy subjects. Subjects with severe inflammatory disease have been found to have a mean concentration of IAIP below about 200 µg/mL. An IAIP concentration of about 250 µg/mL can be used as a cut off to categorize subjects as having or at risk of developing a disease or condition (e.g., an inflammatory disease or condition or an infection). This categorization can then be used to recommend subjects for treatment or for further diagnostic testing. Subjects with a moderate-to-low level of IAIP (e.g., 300 to 200 µg/mL) may benefit from repeated testing over time (e.g., once weekly, twice monthly, once monthly, once bi-monthly, three times annually, or biannually) to determine whether IAIP levels are constant or changing (e.g., increasing or decreasing), as these levels could indicate risk of developing an inflammatory disease or condition or an infection, the presence of an inflammatory disease or condition or an infection, or they could represent the normal baseline level for a subject.

Methods of Determining Disease State or Disease Risk Using the IAIP and IAIP-IAIP Ligand Complex Detection Assays The IAIP and IAIP-IAIP ligand complex detection methods described herein can be used to measure IAIP and/or IAIP-IAIP ligand complexes in a variety of subjects, such as a subject having, or suspected of having, a disease or condition (e.g., an inflammatory disease or condition or an infection (e.g., a bacterial infection)). The level of IAIP and IAIP-IAIP ligand complex in such a subject can be assessed using any of the above assays, e.g., for the purpose of diagnosing the presence of a disease or condition in the subject or the risk that the subject is developing or will develop a disease or condition or monitoring a subject for development or resolution of a disease or condition.

Inflammatory diseases or conditions that can be, e.g., diagnosed or monitored, using the assay methods include, e.g., acute inflammatory disease, sepsis, septic shock, systemic inflammatory response syndrome (SIRS), trauma and/or injury (e.g., wounds, burns, lacerations, contusions, bone fractures, surgical procedures), stroke (e.g., ischemic stroke, hemorrhagic stroke), acute lung injury, acute respiratory distress syndrome (ARDS), pneumonia (e.g., severe pneumonia, severe or non-severe: community acquired pneumonia, hospital acquired pneumonia, nursing home acquired pneumonia), necrotizing enterocolitis, acute pancreatitis, renal diseases (e.g., acute kidney injury, liver injury, acute circulatory failure), preeclampsia, cancer, cancer metastasis, tumor invasion, peripheral artery disease, type 1 or type 2 diabetes, atherosclerotic cardiovascular disease, intermittent claudication, critical limb ischemic disease, myocardial infarction, carotid occlusion, umbilical cord occlusion, low birth-weight, premature birth, surgery-induced inflammation, abscess-associated inflammation, pulmonary insufficiency, peripheral neuropathy, hypoxic ischemia (e.g., neonatal hypoxic ischemic brain injury or hypoxic ischemic encephalopathy), tissue ischemia (e.g., ischemia of skeletal muscle, smooth muscle, cardiac muscle, brain, skin mesenchymal tissue, connective tissue, gastrointestinal tissue, or bone), rheumatoid arthritis, meningitis, multiple sclerosis, inflammatory bowel disease (e.g., Crohn's Disease), chronic obstructive pulmonary disease, rhinitis, preterm labor, or an infectious disease (e.g., influenza or a viral infection, e.g., Dengue fever or West Nile fever).

Infections that can be, e.g., diagnosed or monitored, using the assay methods include, e.g., infections with gram negative bacteria, such as *Neisseria* species including *Neisseria gonorrhoeae* and *Neisseria meningitidis*, *Branhamella* species including *Branhamella catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*, *Brucella* species, *Yersinia* species including *Yersinia pestis* and *Yersinia enterocolitica*, *Francisella* species including *Francisella tularensis*, *Pasteurella* species including *Pasteurella multocida*, *Vibrio cholerae*, *Flavobacterium* species, meningosepticum, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, and *Legionella* species including *Legionella pneumophila*.

The assays described herein can be used to measure IAIP levels in a subject at risk for developing an inflammatory disease or condition or an infection. Risk factors include immunosuppression, immunodeficiency (e.g., a subject that is immunocompromised), advanced age, burns (e.g., thermal burns), trauma, surgery, foreign bodies, cancer, premature birth (e.g., a newborn born prematurely), obesity, and metabolic syndrome.

The methods described herein can be performed as part of a routine physical examination or as a general assessment of health.

Diagnosis of Disease State or Risk of Disease

The assays described herein can be used alongside traditional diagnostic methods to determine whether a subject has or is at risk of developing an inflammatory disease or condition or an infection. The IAIP measurement obtained using the assays can also be used to determine whether a patient is a candidate for treatment with IAIP or an anti-inflammatory or anti-infective therapy or for predicting response to administration of IAIP (e.g., a patient with low levels of IAIP can be treated with IAIP and/or may respond favorably to treatment with IAIP). Measurement of IAIP can be followed by administration of IAIP an anti-inflammatory or anti-infective therapy to a subject, if deemed appropriate (e.g., if IAIP levels are determined to be low, e.g., at least 25% lower than what is considered to be a normal IAIP level in a healthy subject, or if IAIP levels are below 200 µg/mL).

Measurement of IAIP and/or an IAIP-IAIP ligand complex in a sample from a subject can be used to determine whether the subject has or is at risk of developing an inflammatory disease or condition or an infection. The method includes measuring the level of IAIP and/or an IAIP-IAIP ligand complex using one of the methods described above, and comparing the level to a control value (e.g., a reference sample from a healthy patient or an average value obtained from measurements of a population of apparently healthy patients). A reduced level of IAIP in a subject as compared to a healthy control (e.g., a level that is 25%, 30%, 40%, 50% lower or more in a subject compared to a control) or an IAIP concentration of about 250 µg/mL or lower indicates that the subject has or is at risk of developing an inflammatory disease or condition or an infection. An elevated level of an IAIP-IAIP ligand complex in a subject as compared to a healthy control (e.g., a level that is 5%, 10%, 15%, 20%, 25%, 30%, 40%, 50% higher or more in a subject compared to a control) indicates that the subject has or is at risk of developing an inflammatory disease or infection.

The identity of the ligand bound to IAIP in the naturally occurring IAIP-IAIP ligand complex may also provide insight into the type of inflammatory disease or infection that a subject has or is at risk of developing. For example, detecting an elevated level of an IAIP-LPS complex in a sample from a subject may indicate that the subject has or is at risk of developing an infection (e.g., a bacterial infection), and detecting an elevated level of an IAIP-histone complex in a sample from a subject may indicate that the subject has or is at risk of developing an acute systemic inflammatory disease (e.g., sepsis or stroke). Such measurements may be used in diagnosing subjects with particular inflammatory diseases or infections, or in recommending therapies or courses of treatment.

Disease Severity

The methods described herein can also be used to evaluate disease severity. Subjects with an IAIP concentration below about 200 µg/mL, as measured using the assays described herein, can be categorized as having or at high risk of developing severe inflammation or infection or as having a greater morbidity and/or mortality risk. Alternatively, subjects with an elevated level of an IAIP-IAIP ligand complex (e.g., subjects with a level of an IAIP-IAIP ligand complex, such as an IAIP-LPS complex, that is 10%, 20%, 30%, 40%, 50% higher or more compared to a healthy control or known reference concentration value) as measured using the assays described herein, can be categorized as having or at high risk of developing severe inflammation or infection or as having a greater morbidity and/or mortality risk. Once severity is assessed, a corresponding course of treatment can be recommended. Subjects having an IAIP concentration that is indicative of severe inflammation could be selected for more frequent or more aggressive treatment than subjects whose IAIP concentration indicates moderate or low risk of having or developing an inflammatory disease or condition. The assays described herein can be used to measure intact IAIP, and, thus, they can be used to detect life threatening conditions and assess the need for an appropriate therapeutic response.

Monitoring

A subject who has previously had or who is at risk of developing an inflammatory disease or condition or an infection (e.g., a subject with a genetic predisposition, a subject who has been exposed to others with the disease or infection, or a subject having any of the risk factors described above) can be monitored using the methods described herein. Monitoring may also be a suitable approach for subjects with moderate-to-low IAIP levels (e.g., 300 to 200 µg/mL), and/or subjects with slightly elevated levels of an IAIP-IAIP ligand complex (e.g., subjects with a level of an IAIP-IAIP ligand complex, such as an IAIP-LPS complex, that is 1%, 5%, or 10% higher compared to a healthy control or known reference concentration value), particularly if the subjects do not present with clear symptoms of inflammation or infection. IAIP and/or IAIP-IAIP ligand complex measurements can be taken at regular intervals (e.g., once a year, twice a year, once every three months, once monthly, bi-monthly, or once weekly) to determine whether IAIP and/or IAIP-IAIP ligand complex levels are constant or changing. Increasing levels of IAIP and/or decreasing levels of an IAIP-IAIP ligand complex could indicate improvement and lead to a discontinuation of monitoring and/or treatment. Decreasing levels of IAIP and/or increasing levels of an IAIP-IAIP ligand complex could indicate relapse in subjects in recovery or the development or worsening of an inflammatory disease or infection, and could lead to diagnostic testing (e.g., at a greater frequency) and the initiation of, or an increase or change in, treatment.

Treatment Efficacy

The methods described herein can also be used to evaluate treatment efficacy in a subject being treated (e.g., with an antibiotic, anti-inflammatory agent, anti-infective agent, or IAIP) for an inflammatory disease or condition or an infection. IAIP levels can be measured prior to or after the onset of treatment and then measured on an ongoing basis during treatment (e.g., once a day, once a week, bi-weekly, once a month, bi-monthly, once every three months, or twice a year). An increase in IAIP levels (e.g., an increase of 1%, 5%, 10%, 20%, 30% or more relative to a prior measurement) during the course of treatment would indicate improvement and demonstrate the effectiveness of the treatment, while constant or decreasing IAIP levels (e.g., one or more measurements that do not show a change or show a decrease of 1%, 5%, 10%, 20%, 30% or more relative to a prior measurement) would indicate a lack of improvement and suggest that the course of treatment should be modified or changed (e.g., increased in dose or frequency or both, changed to a different therapeutic, or modified to include additional therapeutic agents).

As an alternative, or in addition to measuring IAIP, detection of an IAIP-IAIP ligand complex (e.g., IAIP-LPS) can be used to evaluate the efficacy of treatment with a therapy for treating or reducing the risk of an inflammatory disease or infection. The method includes measuring the level of the IAIP-IAIP ligand complex as a biomarker in a subject undergoing therapy prior to or after the onset of treatment and then measuring on an ongoing basis during treatment (e.g., once a day, once a week, bi-weekly, once a month, bi-monthly, once every three months, or twice a year). The level of the IAIP-IAIP ligand complex can be compared the level to a control value (e.g., a reference sample from a healthy patient or an average value obtained from measurements of a population of control subjects (e.g., healthy patients)) or to a prior measurement taken from the subject. A decrease in the level of the IAIP-IAIP ligand complex toward a "normal level" or a decrease at later time points during treatment (e.g., a decrease of 1%, 5%, 10%, 20%, 30% or more relative to a prior measurement) would indicate that the therapy is efficacious. An increase in the level of the IAIP-IAIP ligand complex (e.g., an increase of 1%, 5%, 10%, 20%, 30% or more relative to a prior measurement or a "normal level") would indicate that treatment is ineffective and requires modification (e.g., a higher dose, more frequent administration, or both, or a different therapeutic or combination therapy).

Methods of Treatment

The invention also features methods of treating, preventing, or reducing the risk of developing an inflammatory disease or condition or an infection (e.g., a severe infection) in a subject (e.g., a human) that has been determined to be in need according to the diagnostic methods described herein (e.g., a subject with low IAIP levels and/or elevated levels of an IAIP-IAIP ligand complex compared to a reference or compared to prior measurements). The subject can be treated with a standard of care therapeutic appropriate for the disease or condition and/or IAIP. The subject may be a neonate, a child, an adolescent, or an adult.

Prior to administration of IAIP or another therapeutic agent to a subject in need thereof, IAIP concentration can be measured in a sample from the subject according to the methods described herein. As an alternative or in addition to measurement of IAIP levels, the method can include detecting an IAIP-IAIP ligand complex prior to administration of IAIP. For example, the method can include detecting an IAIP-LPS complex in a subject having or suspected of having a bacterial infection (e.g., a gram negative bacterial infection), and/or measuring IAIP concentration in a sample from the subject, and administering IAIP to the subject (e.g., administering IAIP to a subject with an increased level of the IAIP-LPS complex compared to a healthy control or a reference value (e.g., a level of the IAIP-LPS complex that is 1%, 5%, 10%, 20%, 30% higher or more than the level in a healthy control), or administering IAIP to a subject at risk of systemic inflammation or shock syndrome (e.g., a subject with IAIP levels at least 25% below those of a healthy control)).

IAIP or compositions containing IAIP can be administered to a subject in need thereof (e.g., as determined by using one or more of the methods described herein). Subjects who can be treated with IAIP include subjects having an infection (e.g., a gram negative bacterial infection) or subjects with an elevated risk of developing an infection (e.g., subjects with one or more risk factors including immunosuppression, immunodeficiency (e.g., a subject that is immunocompromised), advanced age, burns (e.g., thermal burns), trauma, surgery, foreign bodies, cancer, recent birth (e.g., newborns), premature birth (e.g., newborns born prematurely), obesity, and metabolic syndrome). The infection can result from endotoxins triggered by the release of lipopolysaccharide (LPS) molecules from infecting gram negative bacteria. Severe infection by gram negative bacteria can lead to severe systemic inflammation, sepsis, shock syndrome, and death. As shown herein, IAIP binds to LPS, and, therefore, administration of IAIP can be used to treat subjects infected with gram negative bacteria to reduce or prevent LPS-induced cytotoxicity.

Infections suitable for treatment with IAIP include infections with gram negative bacteria, such as *Neisseria* species including *Neisseria gonorrhoeae* and *Neisseria meningitidis*, *Branhamella* species including *Branhamella catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*, *Brucella* species, *Yersinia* species including *Yersinia pestis* and *Yersinia enterocolitica*, *Francisella* species including *Francisella tularensis*, *Pasteurella* species including *Pasteurella multocida*, *Vibrio cholerae*, *Flavobacterium* species, *meningosepticum*, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, and *Legionella* species including *Legionella pneumophila*.

Subjects determined to be in need of treatment (e.g., by using one or more of the methods described herein) or who can be treated with IAIP, after such a need is determined also include subjects having or at risk of developing an inflammatory disease or condition such as acute inflammatory disease, sepsis, septic shock, sterile sepsis, systemic inflammatory response syndrome (SIRS), trauma/injury (e.g., wounds, burns, lacerations, contusions, bone fractures, surgical procedures), stroke (e.g., ischemic stroke, hemorrhagic stroke), acute lung injury, acute respiratory distress syndrome (ARDS), pneumonia (e.g., severe pneumonia, severe or non-severe: community acquired pneumonia, hospital acquired pneumonia, nursing home acquired pneumonia), necrotizing enterocolitis, acute pancreatitis, renal diseases including acute kidney injury, liver injury, acute circulatory failure, preeclampsia, cancer, cancer metastasis, tumor invasion, peripheral artery disease, type 1 or type 2 diabetes, atherosclerotic cardiovascular disease, intermittent claudication, critical limb ischemic disease, myocardial infarction, carotid occlusion, umbilical cord occlusion, low birthweight, premature birth, surgery-induced inflammation, abscess-associated inflammation, pulmonary insufficiency, peripheral neuropathy, hypoxic ischemia (e.g., neonatal hypoxic ischemic brain injury or hypoxic ischemic encephalopathy), tissue ischemia (e.g., ischemia of skeletal muscle, smooth muscle, cardiac muscle, brain, skin mesenchymal tissue, connective tissue, gastrointestinal tissue, or bone), rheumatoid arthritis, meningitis, multiple sclerosis, inflammatory bowel disease (e.g., Crohn's Disease), chronic obstructive pulmonary disease, rhinitis, preterm labor, or an infectious disease (e.g., influenza or a viral infection, e.g., Dengue fever or West Nile fever); subjects with low IAIP levels (e.g., IAIP levels of 250, 225, 200, 175, 150 µg/mL or lower), and subjects with increased levels of disease-associated IAIP-IAIP ligand complexes (e.g., IAIP-LPS or IAIP-histone).

Administration

IAIPs (e.g., IαI and/or PαI), or a composition containing such proteins and a pharmaceutically acceptable excipient, diluent, or carrier, can be administered to a subject (e.g., a human) having or at risk of developing an inflammatory disease or condition or an infection that has been determined to be in need according to the diagnostic methods described herein (e.g., a subject with low IAIP levels and/or elevated levels of an IAIP-IAIP ligand complex compared to a reference or compared to prior measurements) by any suitable route, including, for example, parenterally, by inhalation spray, topically, nasally, buccally, sublingually, intranasally, by oral administration, inhalation, suppository, rectally, vaginally, or by injection. Administration by injection includes, for example, intravenous, intraperitoneal, subcutaneous, intradermal, intracutaneous, intramuscular, intraarticular, intraarterial, intrasynovial, intrasternal, intrathecal, intralesional, intravitreous, and intracranial injection. If the patient is hospitalized, the preferred method of administration is by intravenous injection.

The IAIPs (e.g., IαI and/or PαI) or the composition containing such proteins may be administered to the subject one or more times every 1, 2, 3, 4, 5, 6, 8, 12, or 24 hours; one or more times every 1, 2, 3, 4, 5, or 6 days; or one or more times every 1, 2, 3, or 4 weeks. In other cases, the IAIPs (e.g., IαI and/or PαI) or the composition containing such proteins are administered as a continuous infusion.

IAIPs (e.g., IαI and/or PαI) for use in the compositions of the invention can be obtained from, e.g., human plasma and blood by methods known in the art (see, e.g., U.S. Pat. No. 9,139,641, which is incorporated herein by reference in its entirety).

In particular, the IAIPs can be obtained at a purity of 80% to 100% (e.g., about 80%, about 85%, about 90%, about 95%, about 96%, about 97%, about 98%, about 99%, or about 100%) from a natural source (e.g., blood) and used to prepare a composition of the invention (see, e.g., U.S. Pat. No. 7,932,365, which is incorporated herein by reference in its entirety). The IAIPs for use in the compositions of the invention can also be exposed to low pH conditions (e.g., a wash buffer having a pH of about 4.0 or lower, e.g., about pH 3.6 or lower) during purification (as described in U.S. Pat. No. 9,139,641).

The compositions may include any suitable IAIP, for example, IαI, PαI, a heavy chain, a light chain, or any combination thereof. For example, the composition may include IαI, PαI, and/or bikunin. In some cases, the composition may include IαI and PαI. The heavy chain can be H1, H2, H3, H4, or H5.

The light chain can be bikunin.

The proportion or concentration of IAIPs (e.g., IαI and/or PαI) in the compositions can vary depending upon a number of factors including dosage, chemical characteristics (e.g., hydrophobicity), and the route of administration. The IAIPs (e.g., IαI and/or PαI) may be present in the composition in a physiological proportion. Physiological proportions may be, for example, the proportions found in a person or animal that is healthy and/or the ratio of IαI and PαI that appears naturally in human plasma. Physiological proportions are typically from between about 60% to about 80% IαI and between about 20% to about 40% PαI.

IAIPs (e.g., IαI and/or PαI) or compositions thereof can have a half-life of, for example, greater than about 1, 1.5, 2, 2.5, 3, 3.5, 4, 4.5, 5, 7.5, or 10 hours. IAIPs (e.g., IαI and/or PαI) or compositions thereof can have a half-life of greater than about 5 hours or, preferably, greater than about 10 hours. Longer half-lives are preferred, for example, because fewer doses are required to be administered to a subject over time.

Dosages

A pharmaceutically acceptable composition of the invention for administration to a subject having or at risk of developing an inflammatory disease or condition or an infection that has been determined to be in need according to the diagnostic methods described herein (e.g., a subject with low IAIP levels and/or elevated levels of an IAIP-IAIP ligand complex compared to a reference or compared to prior measurements) includes IAIPs (e.g., IαI and/or PαI) in a dosage known in the art (see, e.g., U.S. Pat. No. 7,932,365, International Patent Application Publication No. WO2009154695, and U.S. Patent Application Publication No. 2009/0190194, each of which is incorporated herein by reference in its entirety). For example, compositions of the invention can be administered in a dosage ranging from about 1 mg/kg to 50 mg/kg, preferably dosages between 10 mg/kg and 30 mg/kg. The dose can be administered one or more times every 1, 2, 3, 4, 5, 6, 8, 12, or 24 hours, every 1, 2, 3, 4, 5, or 6, days, or every 1, 2, 3, or 4 weeks, or as needed. Lower or higher doses than those recited above may be advantageous. Specific dosage and treatment regimens for any particular subject will depend upon a variety of factors, including the activity of the specific composition employed, the age, body weight, general health status, sex, diet, time of administration, rate of excretion, drug combination, the severity and course of the disease (e.g., the patient's condition and/or symptoms), the subject's disposition to the disease, and the judgment of the treating medical professional (e.g., the physician). The IAIPs may be combined with a carrier material to produce a single dosage form.

Upon improvement of the patient's condition, as evaluated based on improvement of symptoms or by measurement of IAIP and/or an IAIP-IAIP ligand complex as described herein, a maintenance dose of an IAIP composition or combination therapy may be administered, if necessary. Subsequently, the dosage or frequency of administration, or both, may be reduced, as a function of the reduction in symptoms, to a level at which the improved condition is retained. When the symptoms have been alleviated to a desired level or IAIP has been increased and/or IAIP-IAIP ligand complexes have been decreased to a desired level, treatment may cease. Subjects may, however, require intermittent treatment on a long-term basis upon any recurrence of disease symptoms or decrease in IAIP levels. Improvement of the condition may also be judged based upon the level of IαIp in a biological sample derived from the patient (e.g., blood (e.g., whole blood, plasma, or serum), bronchial lavage fluid (BALF), sputum, urine, cerebrospinal fluid (CSF), or a tissue homogenate (e.g., a homogenate of a liver biopsy). The level of IαIp and/or an IAIP-IAIP complex in a biological sample can be determined using one or more of the assays described herein.

Formulations

The invention provides methods of administering IAIP to a subject having or at risk of developing an inflammatory disease or condition or an infection that has been determined to be in need according to the diagnostic methods described herein (e.g., a subject found to have low levels of IAIP and/or elevated levels of an IAIP-IAIP ligand complex, e.g., an IAIP-LPS complex, as measured using the methods described herein). The methods include administration of IAIPs (e.g., IαI and/or PαI), a composition that includes IAIPs (e.g., IαI and/or PαI) and a pharmaceutically acceptable excipient, carrier, or diluent, or such compositions combined with a secondary treatment, as is described herein. The compositions can be formulated as a solid or a liquid. The compositions can be formulated for administration by any suitable means including those described herein.

Injectable forms of IAIPs for administration are particularly preferred. IAIPs and compositions containing the same may be formulated for intravenous, intraperitoneal, subcutaneous, intracutaneous, intramuscular, intraarticular, intraarterial, intrasynovial, intrasternal, intrathecal, intradermal, intravitreous, intralesional and intracranial injection or infusion techniques. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent.

The compositions may also be formulated for oral administration in any orally acceptable dosage form including, but not limited to, capsules, tablets, pills, emulsions and aqueous suspensions, dispersions and solutions. For preparing solid compositions, such as tablets, the IAIPs may be mixed with a pharmaceutical excipient to form a solid pre-formulation composition containing a homogeneous mixture. This solid pre-formulation can then be subdivided into unit dosage forms of the type described above containing from, for example, 1 mg/kg to about 50 mg/kg of IAIPs (e.g., IαI and/or PαI). The solid pre-formulation can contain about 10 mg/kg to 30 mg/kg of IAIPs (e.g., IαI and/or PαI). The tablets or pills of the present invention can be coated or otherwise compounded to provide a dosage form affording the advantage of prolonged action.

The liquid forms in which the compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as described herein and/ or known in the art. The compositions can be administered by the oral or nasal respiratory route for local or systemic effect. Compositions can be nebulized by use of inert gases.

Topical administration of the compositions is useful when the desired treatment involves areas or organs readily accessible by topical application. For application topically to the skin, the composition should be formulated with a suitable ointment containing the active components suspended or dissolved in a carrier. Alternatively, the pharmaceutical composition can be formulated with a suitable lotion or cream containing the active composition suspended or dissolved in a carrier with suitable emulsifying agents.

The pharmaceutical compositions may also be administered in the form of suppositories for rectal administration. These compositions can be prepared by mixing a composition of this invention with a suitable non-irritating excipient which is solid at room temperature but liquid at the rectal temperature and therefore will melt in the rectum to release the active components. Topically-transdermal patches are also included in this invention.

The compositions administered to a subject can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as those described in (U.S. Pat. No. 3,773,919; European Patent No. 58,481, European Patent No. 133, 988, Sidman, K. R. et al., Biopolymers 22: 547-556, and Langer, R. et al., J. Biomed. Mater. Res. 15:267-277; Langer, R. Chem. Tech. 12:98-105). Other examples of sustained-release compositions include semi-permeable polymer matrices in the form of shaped articles, e.g., films, or microcapsules. Delivery systems also include non-polymer systems that are: lipids; hydrogel release systems; sylastic systems; peptide based systems; wax coatings; compressed tablets using conventional binders and excipients; partially fused implants; and the like. Methods for preparation of such formulations will be apparent to those skilled in the art (see, e.g., U.S. Pat. Nos. 4,452,775, 4,667,014, 4,748,034 and 5,239,660, 3,832, 253, and 3,854,480).

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agents is described, e.g., in Banga, Therapeutic Peptides and Proteins: Formulation, Processing, and Delivery Systems (Third Edition), CRC Press 2015.

Combination Therapies

The methods of the invention also include administering or co-administering a second treatment (e.g., as a standalone therapy or in addition to IAIPs (e.g., IαI and/or PαI) or a composition thereof) for the treatment of an inflammatory disease or condition (e.g., sepsis, septic shock, sterile sepsis, SIRS, trauma/injury (e.g., wounds, burns, lacerations, contusions, bone fractures, surgical procedures), stroke (e.g., ischemic stroke, hemorrhagic stroke), acute lung injury, ARDS, pneumonia (e.g., severe pneumonia, severe or non-severe: community acquired pneumonia, hospital acquired pneumonia, nursing home acquired pneumonia), necrotizing enterocolitis, acute pancreatitis, renal diseases including acute kidney injury, liver injury, acute circulatory failure, preeclampsia, cancer, cancer metastasis, tumor invasion, peripheral artery disease, type 1 or type 2 diabetes, atherosclerotic cardiovascular disease, intermittent claudication, critical limb ischemic disease, myocardial infarction, carotid occlusion, umbilical cord occlusion, low birth-weight, premature birth, surgery-induced inflammation, abscess-associated inflammation, pulmonary insufficiency, peripheral neuropathy, hypoxic ischemia, tissue ischemia, rheumatoid arthritis, meningitis, multiple sclerosis, inflammatory bowel disease (e.g., Crohn's Disease), chronic obstructive pulmonary disease, rhinitis, preterm labor, or an infectious disease) or an infection (e.g., a bacterial infection). For example, the second treatment may include administering an antibiotic agent if the subject has or is at risk of developing an bacterial infection, an antiviral agent if the subject has or is at risk of developing an viral infection (e.g., Dengue fever or West Nile fever), an antifungal agent if the subject has or is at risk of developing a fungal infection, an antiparasitic agent if the subject has or is at risk of developing a parasitic infection, an anti-inflammatory agent if the subject has or is at risk of developing an inflammatory disease or condition described herein, an anti-cancer agent if the subject has or is at risk of developing cancer or cancer metastasis, an anti-coagulant if the subject has or is at risk of stroke or myocardial infarction, an immunomodulatory agent if the subject has cancer or an autoimmune disease or condition (e.g., inflammatory bowel disease or rheumatoid arthritis), and a bronchodilator agent, a complement inhibitor, a vasopressor, a sedative, or mechanical ventilation if the subject has or is at risk of developing acute lung injury, ARDS, or pneumonia.

When the method includes administering a combination of IAIPs (e.g., IαI and/or PαI), or a composition including IAIPs (e.g., IαI and/or PαI) and a pharmaceutically acceptable excipient, diluent, or carrier, and one or more second treatment agents, each agent is present at a dosage level of between about 1 to 100%, and more preferably between about 5 to 95%, of the dosage normally administered in a monotherapy regimen. The agent(s) of the second treatment may be administered separately, as part of a multiple dose regimen, from the IAIPs (e.g., IαI and/or PαI) or the composition thereof. The IAIPs and agent(s) of the second treatment can be administered simultaneously or sequentially in any order. Alternatively, the agent(s) of the second treatment may be part of a single dosage form, e.g., mixed together with the IAIPs (e.g., IαI and/or PαI) in a single composition.

Agents that can be administered in combination with IAIPs (e.g., IαI and/or PαI) include dideoxynucleosides, e.g. zidovudine (AZT), 2',3'-dideoxyinosine (ddl) and 2',3'-dideoxycytidine (ddC), lamivudine (3TC), stavudine (d4T), and TRIZIVIR (abacavir+zidovudine+lamivudine); non-nucleosides, e.g., efavirenz (DMP-266, DuPont Pharmaceuticals/Bristol Myers Squibb), nevirapine (Boehringer Ingleheim), and delaviridine (Pharmacia-Upjohn); TAT antagonists such as Ro 3-3335 and Ro 24-7429; protease inhibitors, e.g., furin inhibitors, indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir); interferon, e.g., alpha-interferon, interleukin II, and phosphonoformate (Foscarnet); or entry inhibitors, e.g., T20 (enfuvirtide, Roche/Trimeris) or UK-427,857 (Pfizer), levamisol or thymosin, cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide; and anti-coagulants, e.g., Anti-thrombin III and activated Protein C.

Additional exemplary agents that can be administered in combination with IAIPs (e.g., IαI and/or PαI) or compositions thereof are discussed below.

Antibiotic Agents

If the subject has or is at risk of developing a bacterial infection (e.g., necrotizing enterocolitis or a gram negative bacterial infection) the second treatment may include an antibiotic agent that is used to treat a bacterial infection. Non-limiting examples of antibiotic agents include amoxicillin, penicillin, doxycycline, clarithromycin, benzylpenicillin, azithromycin, daptomycin, linezolid, levofloxacin, moxifloxacin, gatifloxcin, gentamicin, macrolides, cephalosporins, azithromycin, ciprofloxacin, cefuroxime, amoxillin-potassium clavulanate, erythromycin, sulfamethoxazole-trimethoprim, doxycycline monohydrate, cefepime, ampicillin, cefpodoxime, ceftriaxone, cefazolin, erythromycin ethylsuccinate, meropenem, piperacillin-tazobactam, amikacin, erythromycin stearate, cefepime in dextrose, doxycycline hyclate, ampicillin-sulbactam, ceftazidime, gemifloxacin, gentamicin sulfate, erythromycin lactobionate, imipenem-cilastatin, cefoxitin, cefditoren pivoxil, ertapenem, doxycycline-benzoyl peroxide, ampicillin-sulbactam, meropenem, cefuroxime, cefotetan, piperacillin-tazobactam, broad-spectrum fluoroquinolones (which may be used, for example, to treat pneumonia caused by atypical pathogens such as *Mycoplasma pneumoniae* or *Chlamydophila pneumoniae*), and others known in the art.

Antiviral Agents

If the subject has or is at risk of developing a viral infection (e.g., Dengue fever or West Nile fever), the second treatment may include an antiviral agent that is used to treat a viral infection. Non-limiting examples of antiviral agents include zanamivir, oseltamivir, permivir, ribavirin, acyclovir, ganciclovir, foscarnet, cidofovir, and others known in the art.

Antifungal Agents

If the subject has or is at risk of developing a fungal infection, the second treatment may include an antifungal agent that is used to treat a fungal infection. Non-limiting examples of antifungal agents include amphotericin, caspofungin, voriconazole, itraconazole, posaconazole, fluconazole, flucytosine, and others known in the art.

Antiparasitic Agents

If the subject has or is at risk of developing a parasitic infection, the second treatment may include an antiparasitic agent that is used to treat a parasitic infection (e.g., a parasitic protozoan infection. Non-limiting examples of antiparasitic agents include nitazoxanide, melarsoprol, eflornithine, metronidazole, tinidazole, miltefosine, mebendazole, pyrantel pamoate, thiabendazole, diethylcarbamazine, ivermectin, albendazole, praziquantel, rifampin, and others known in the art.

Anti-Inflammatory Agents

If the subject has or is at risk of developing an inflammatory disease or condition described herein, the second treatment may include an anti-inflammatory agent that is used to treat or reduce inflammation. Non-limiting examples of anti-inflammatory agents include corticosteroids, statins, steroids, nonsteroidal anti-inflammatory drugs, glucocorticoids, and others known the art.

Bronchodilators

If the subject has or is at risk of developing acute lung injury, ARDS, or pneumonia, the second treatment may include a bronchodilator that is used to relax the bronchial muscles allowing airways to be larger and air to pass through the lungs. Non-limiting examples of bronchodilators include beta 2 agonists, xanthines, ipratropium, oxitropium, muscarinic receptor antagonists, ipratropium, oxitropium, theophylline, theobromine, caffeine, salbutamol, isoproterenol, albuterol, levalburerol, pirbuterol, metaproterenol, terbutaline, salmeterol, formoterol, and others known in the art.

Vasopressors

If the subject has or is at risk of developing acute lung injury, ARDS, pneumonia, or trauma/injury (e.g., wounds, burns, or surgical procedures), the second treatment may include a vasopressor that causes vasoconstriction and/or an increase in blood pressure. Non-limiting examples of vasopressors include epinephrine, isoproterenol, phenylephrine, norepinephrine, dobutamine, ephedrine, droxidopa, and others known in the art.

Sedatives

The second treatment may include a sedative. Non-limiting examples of sedatives include propofol, diprivan, morphine, fentanyl, midazolam, lorazepam, precede, infumorph, dexmedetomidine, alfentanil, and others known in the art.

Complement Inhibitors

If the subject has or is at risk of developing acute lung injury, ARDS, or pneumonia, the second treatment may include an inhibitor of complement activation. The composition may inhibit activation of one or more complement components such as C1, C2, C3 (e.g., C3a and C3b), C4 (e.g., C4b), C5 (e.g., C5a and C5b), C6, C7, C8, C9, membrane attack complex, Factor B, Factor D, MASP-1, and MASP-2, or fragments thereof. The complement inhibitors may include protease inhibitors such as C1-INH and Rhucin/rhC11NH, soluble complement regulators such as sCR1/TP10, CAB-2/MLN-2222, therapeutic antibodies such as eculizumab/SOLIRIS®, Pexelizumna, ofatumumab, complement component inhibitors such as compstatin, receptor antagonists such as PMX-53 and rhMBL.

Kits

The invention also features kits for use in measuring IAIP in a sample (e.g., a fluid sample) from a patient (e.g., a human patient, such as a neonate, a child, an adolescent, or an adult). The kit may include one or more of the following: a support (e.g., a plate (e.g., a multi-well plate)), particles (e.g., magnetic particles, e.g., nanoparticles, magnetic nanoparticles), biochips, resins, containers (e.g., tubes), membranes (e.g., nitrocellulose membranes, PVDF membranes), test strips (e.g., cellulose, glass fiber, or nitrocellulose) or beads (e.g., protein A or protein G beads, magnetic beads, glass beads, plastic beads)) containing an immobilized IAIP binding agent (e.g., an IAIP-specific antibody or an IAIP ligand), a labeled IAIP detection agent (e.g., an IAIP ligand or IAIP-specific antibody), a wash buffer, a blocking agent, a substrate for detection of the label, a dilution agent, and instructions for performing the detection assay. The binding agent and detection agent may be provided in containers, or the binding agent may be provided pre-attached to the support (e.g., the binding agent is already attached to the plate or test strip).

The invention also features kits for use in measuring an IAIP-IAIP ligand complex in a sample (e.g., a fluid sample) from a patient. The kit may include one or more of the following: a support (e.g., a plate (e.g., a multi-well plate)), particles (e.g., magnetic particles, e.g., nanoparticles, magnetic nanoparticles), biochips, resins, containers (e.g., tubes), membranes (e.g., nitrocellulose membranes, PVDF membranes), test strips (e.g., cellulose, glass fiber, or nitrocellulose) or beads (e.g., protein A or protein G beads, magnetic beads, glass beads, plastic beads)) containing an immobilized binding agent (e.g., an IAIP-specific antibody, a different IAIP ligand, or an antibody that binds specifically to the IAIP ligand), a labeled detection agent (e.g., a different IAIP ligand, an IAIP-specific antibody, or an antibody that binds specifically to the IAIP ligand), wash buffers, a blocking agent, a substrate for detection of the label, a dilatation agent, and instructions for performing the detection assay. The binding agent and detection agent may be provided in containers, or the binding agent may be provided pre-attached to a support (e.g., the binding agent may be already attached to a plate or test strip).

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1: Heparin-IAIP Assay

Preparation of Biotinylated Heparin

Heparin (Heparin Sodium Injection USP, Sagent Pharmaceuticals, Cat #NDC 25021-400-30) was conjugated with biotin using the Biotin Hydrazide reagent (ApExBIO, Cat #A87007) according to the manufacturer's instructions. Briefly, 1000 IU heparin solution was mixed with 0.25 mg crosslinker reagent EDC (1-(3-Dimethylaminopropyl)-3-3ethylcarbodiimide hydrochloride, Alfa Aesar Cat #A10807) and 0.5 mM Biotin hydrazide that had been previously dissolved in DMSO in 0.1 M MES buffer pH 4.7 with gentle mixing at room temperature for 3 hrs. The unconjugated biotin and buffer exchange was carried out by ultrafiltration on an Amicon Ultra centrifugal filter device with 5 kDa cut off filter membrane (Millipore). Following dilution in d-H2O, the biotinylated Heparin was ready for use in the assay.

"Sandwich Type" Heparin-IAIP ELISA

Figure 3A:
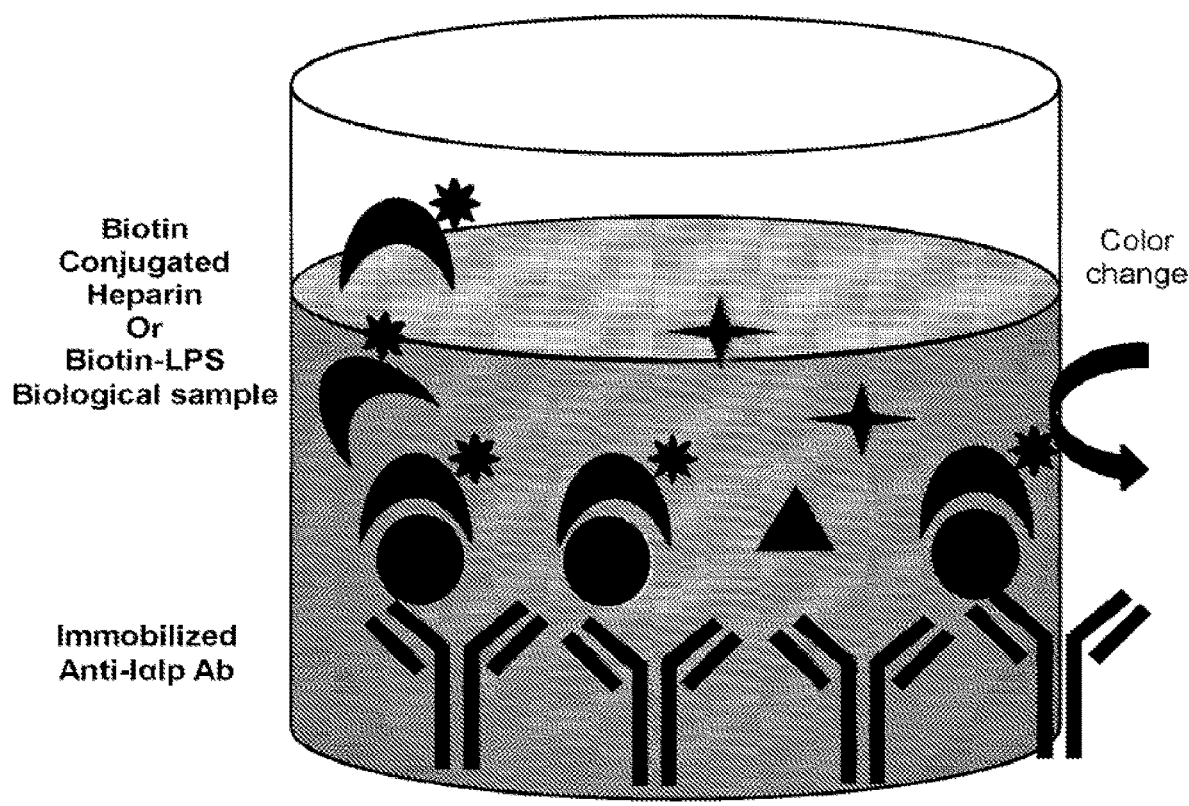
FIG. 3A is a schematic depicting the "sandwich-type" ELISA using labeled IAIP ligands (e.g., biotinylated heparin or LPS) and exemplary standard curves generated using said ELISA. In this version of the assay, an antibody specific for IAIP (e.g., MAb 69.26) is immobilized to a support, such as a multi-well plate, and a biological sample is then added to the support containing the immobilized antibody. If IAIP is present in the sample, it will bind to the antibody and then be detected by the addition of the labeled IAIP ligand.
Figure 3B:
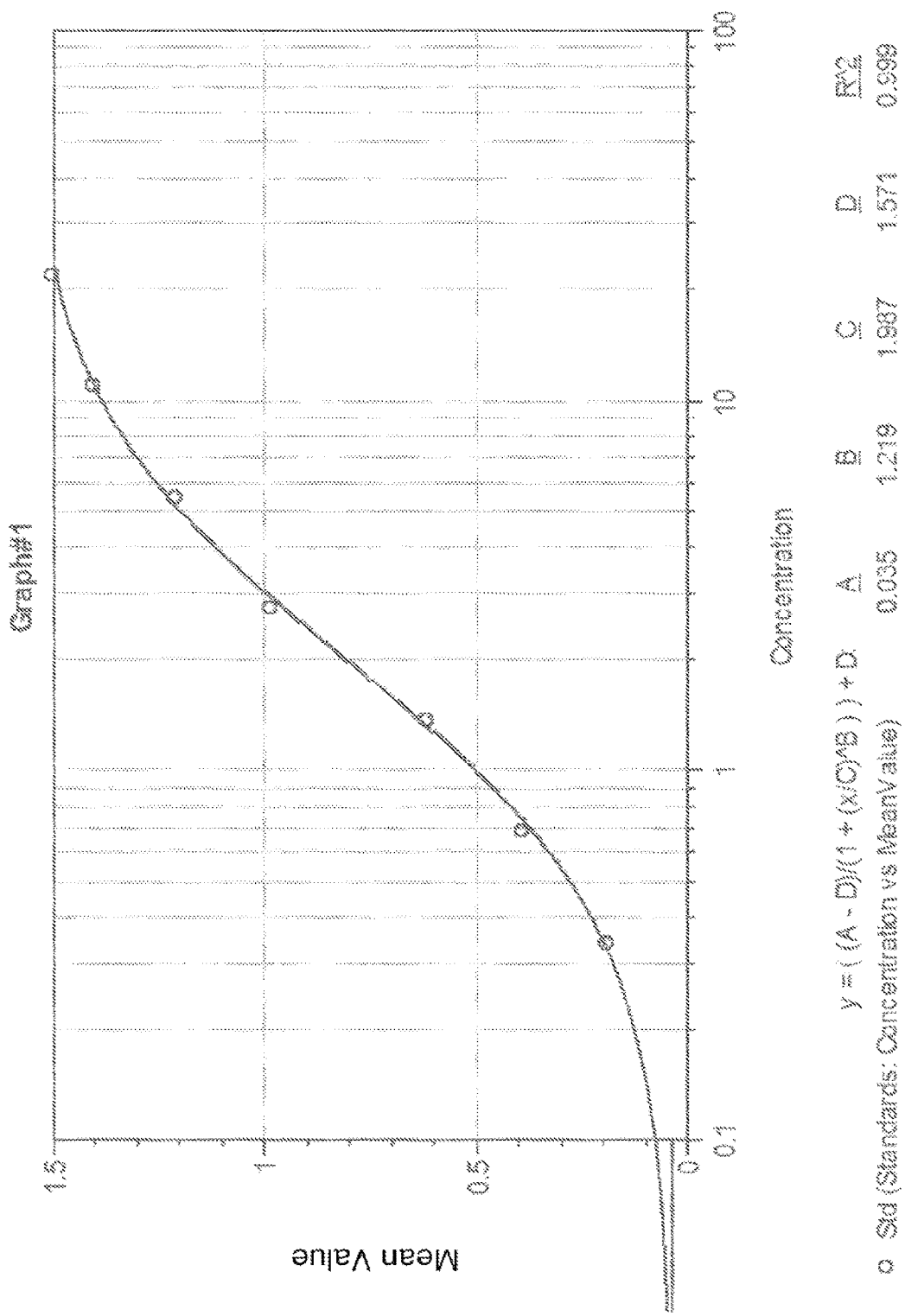

Purified mouse monoclonal antibody against the light chain of human IAIP (MAb 69.26) was immobilized on a 96-well microplate (Immulon 600, Greiner BioOne) at 200 ng/well at 32° C. for 2 hrs. After blocking with 5% non-fat dried milk for 1 hr and washing with TBS-T (TBS+0.05% Tween 20), unknown samples and known IAIP standard were diluted in TBS+0.1% Tween 20 and added to the microplate (final volume 50 uL/well). The samples and the serially diluted IAIP standard solution were incubated for 1 hr at 32° C. After several washes of the microplate with TBS-T, biotinylated heparin was diluted in a buffer containing 20 mM Acetic acid+25 mM NaCl, pH 4.0 (1:2500) and 50 μL was added per well. The biotinylated heparin was incubated for 30 minutes at 32° C. and the microplate was then washed at least three times using TBS-T. Finally, HRP-conjugated Streptavidin (Pierce) diluted at 1:5000 (50 uL/well) was added to the microplate. Following washing, 50 μL of the substrate TMB was added (Neogen Enhanced K-Blue TMB substrate) and the reaction was stopped with the addition of 50 μL 1 M HCl and the color change was read on spectrophotometer (Molecular Devices) at 450 nm wavelength. The standard curve was generated using four-point logistic regression (SoftMax Pro software, Molecular Devices) and a seven-point curve was plotted from maximum IAIP concentration of 2.0 μg/mL to 0.03125 μg/mL with serial two-fold dilution as shown in FIG. 3B. The IAIP concentration of the unknown samples was calculated based on the generated standard curve.

Example 2: LPS-IAIP Assay

Preparation of Biotinylated Endotoxin/LPS (Lipopolysaccharide):

Lipopolysaccharide (LPS/endotoxin) from *Escherichia coli* O55:B5 (Sigma Catalog #L2280) was labeled with biotin using Biotin Hydrazide reagent (ApExBIO, Cat #A87007) according to the manufacturer's instructions and similarly to the protocol used for heparin. 10 mg LPS was reconstituted in 0.1 M MES buffer and 2.5 mM Biotin-Hydrazide and 2.5 mg EDC (1-(3-Dimethylaminopropyl)-3-3ethylcarbodiimide hydrochloride, Alfa Aesar Cat #A10807) were gently mixed for 3 hrs at room temperature. The removal of unconjugated LPS and buffer exchange were carried out by ultrafiltration on Amicon Ultra centrifugal filter device with a 5 kDa cut off filter membrane (Millipore). Following dilution in d-H2O, the biotinylated LPS was ready for use in the assay.

"Sandwich Type" LPS-IAIP ELISA

Similar to the heparin-IAIP protocol described above, purified mouse monoclonal antibody against the light chain of human IAIP (MAb 69.26) was immobilized on 96-well microplate (Immulon 600, Greiner BioOne) at 50 ng/well at 32° C. for 2 hrs. After blocking with 5% non-fat dried milk for 1 hr and washing with TBS-T (TBS+0.05% Tween 20), unknown samples and known IAIP standard were diluted in TBS+0.1% Tween 20 and added to the microplate (final volume 50 uL/well). The samples and the serially diluted IAIP standard solution were incubated for 1 hr at 32° C. After several washes of the microplate with TBS-T, biotinylated LPS was diluted in a buffer containing 20 mM Acetic acid+25 mM NaCl, pH 4.0 (1:32,000) and 50 uL was added per well. The biotinylated LPS was incubated for 30 minutes at 32° C. and the microplate was then washed at least three times using TBS-T. Finally, HRP-conjugated Streptavidin (Pierce) diluted at 1:10,000 (50 μL/well) was added to the microplate. Following washing, 50 μL of the substrate TMB was added (Neogen Enhanced K-Blue TMB substrate) and the reaction was stopped with the addition of 50 μL 1 M HCl and the color change was read on spectrophotometer (Molecular Devices) at 450 nm wavelength. The standard curve was generated using four-point logistic regression (SoftMax Pro software, Molecular Devices) and a seven-point curve was plotted from maximum IAIP concentration of 2.0 μg/mL to 0.03125 μg/mL with serial two-fold dilution as shown in FIG. 3C.

Example 3: Analysis of Blood Samples from Patients Diagnosed with Severe Community Acquired Pneumonia (sCAP)

Figure 2A:
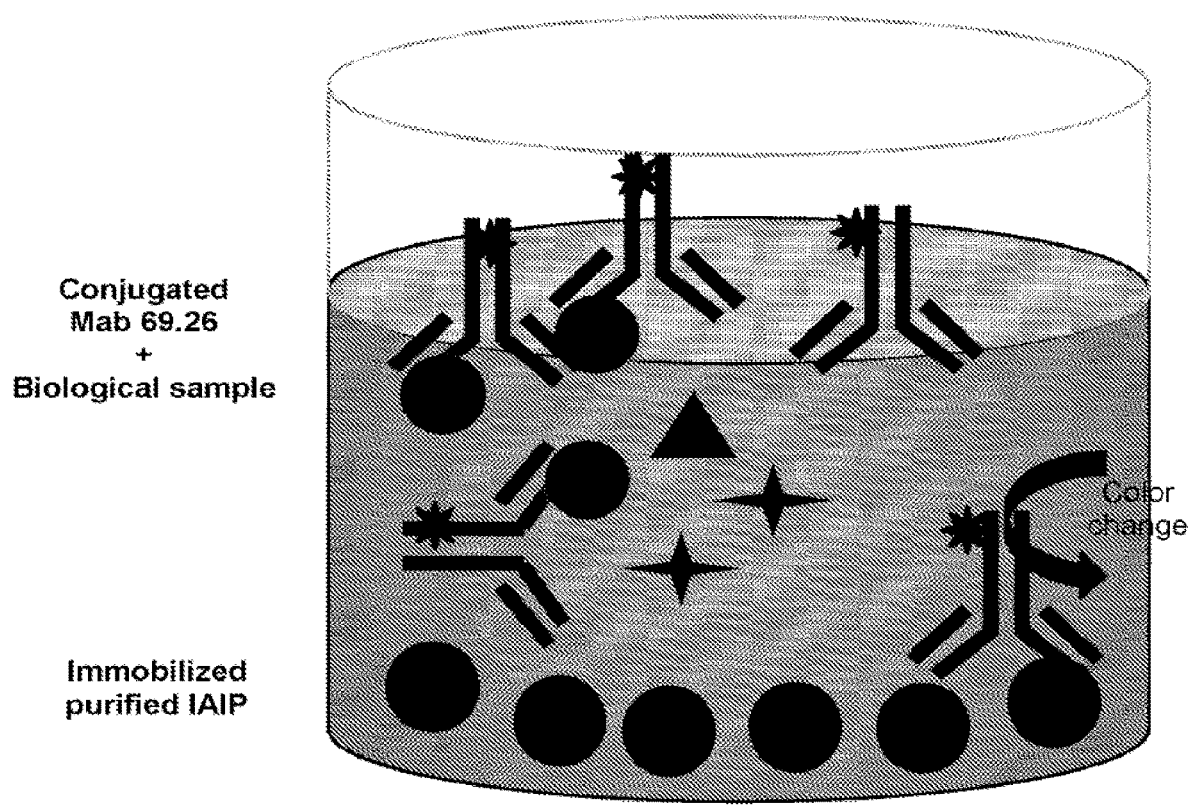
FIG. 2A is a schematic depicting a competitive IAIP ELISA assay. In this assay, purified IAIP is immobilized to a support, such as a multi-well plate, and a biological sample and a labeled antibody directed to IAIP (e.g., MAb 69.26) are then added to the purified IAIP.
Figure 2B:
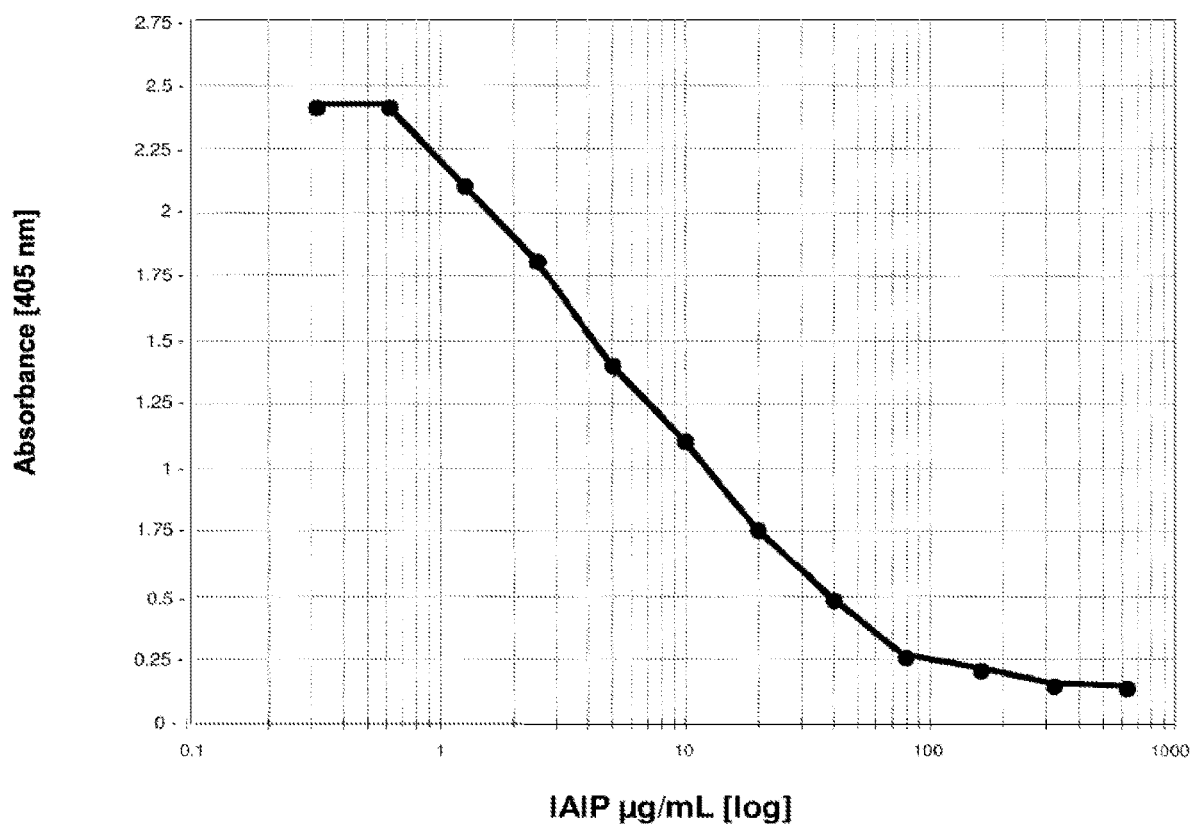
FIG. 2B is a graph showing a standard curve of data produced by a competitive IAIP ELISA assay. This assay provides an indirect measure of IAIP based on competitive antibody binding between IAIP in the sample and immobilized, purified IAIP. Lower signal indicates higher amounts of IAIP in the sample.
Figure 4:
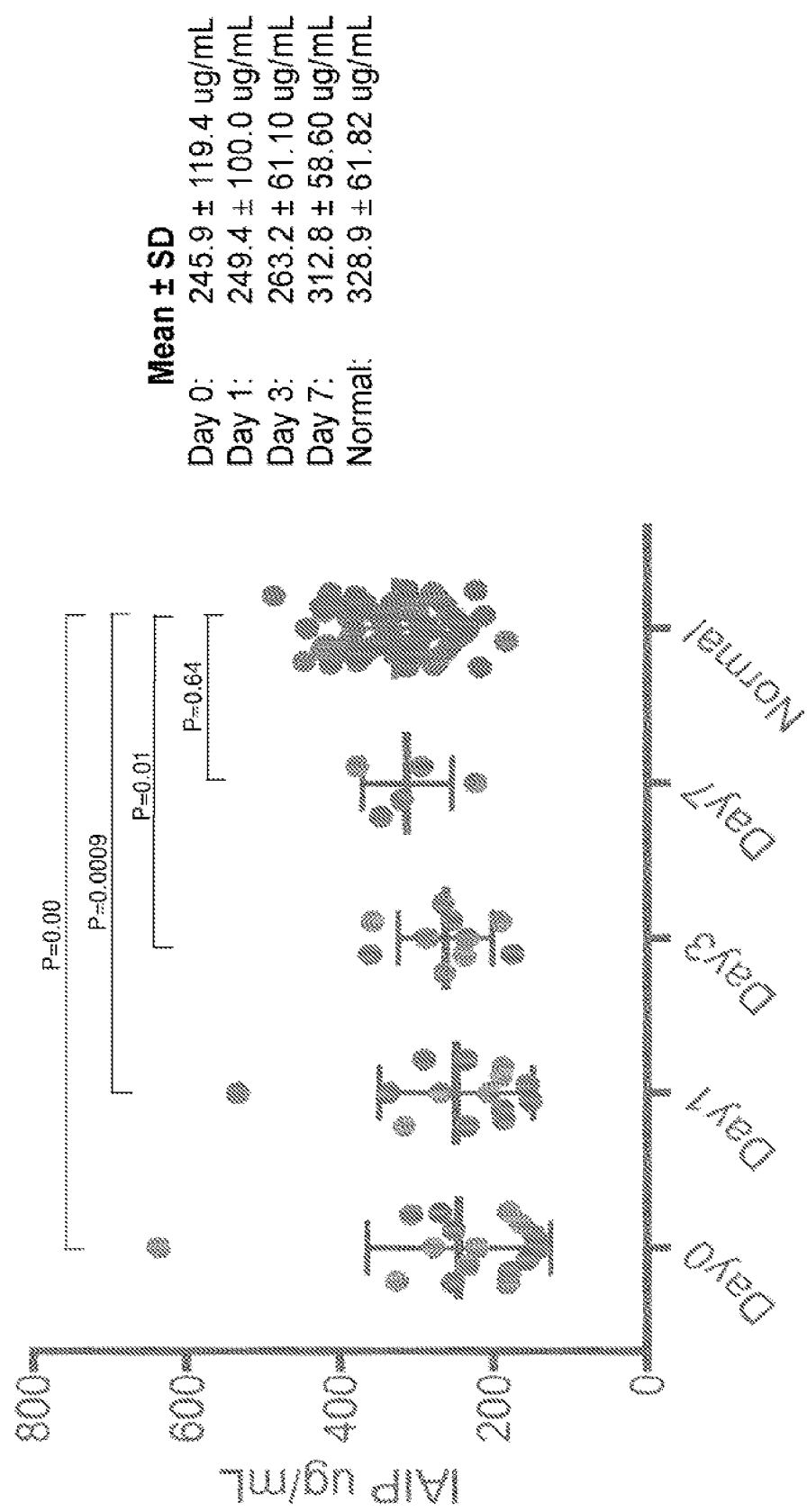
FIG. 4 is a graph showing measurements of IAIP concentration obtained using a competitive ELISA as depicted in FIG. 2A. IAIP was measured in plasma samples from patients with severe community acquired pneumonia (sCAP) on successive days during hospitalization and compared to IAIP levels in normal control subjects. The competitive ELISA yielded an average IAIP concentration of 250 μg/mL in patients with sCAP and 330 μg/mL in healthy controls, and found significant differences between IAIP levels in subjects with sCAP and healthy controls on days 0, 1, and 3.
Figure 5:
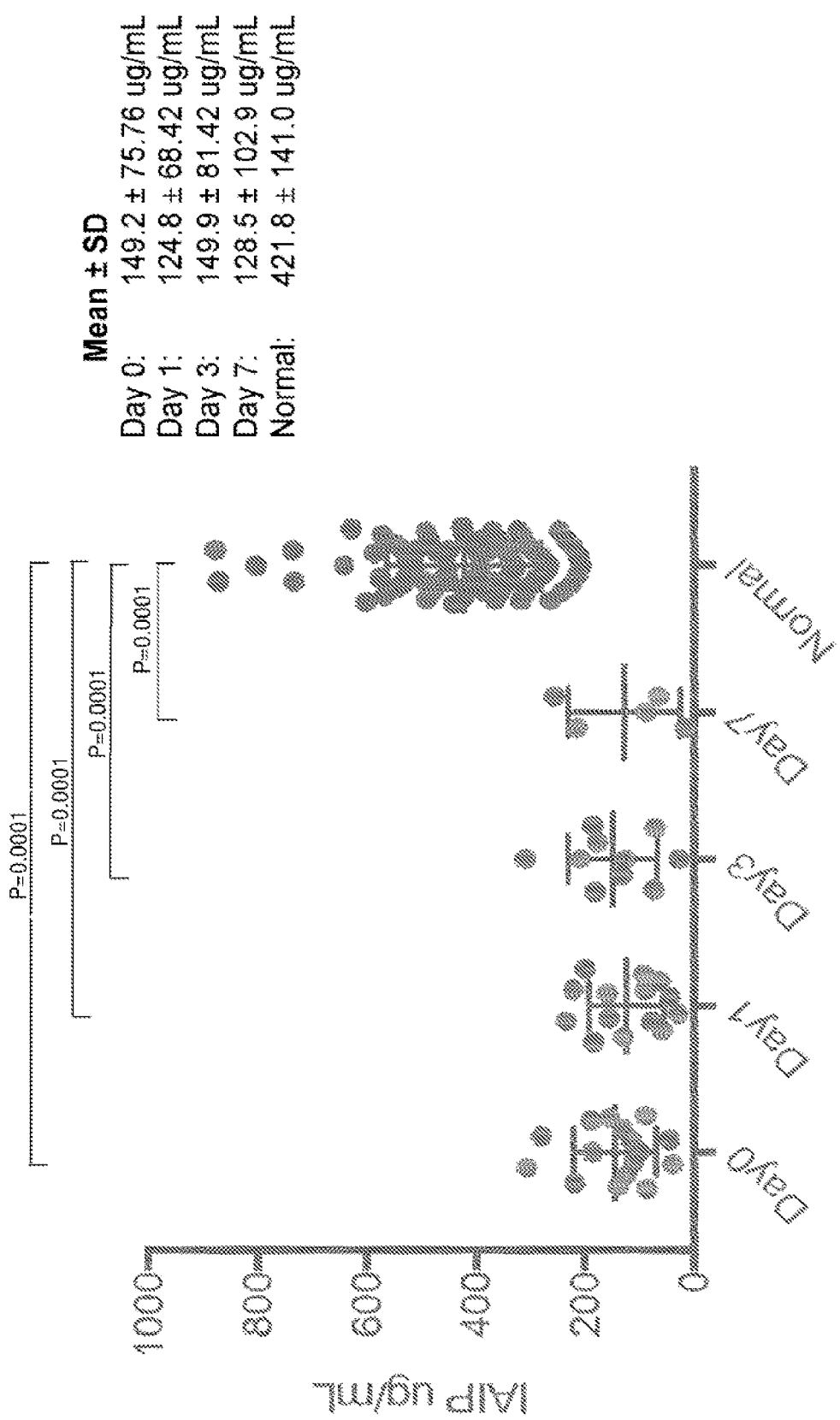
FIG. 5 is a graph showing measurements of IAIP concentration obtained using a "sandwich-type" ligand-IAIP ELISA as depicted in FIG. 3A. The results depicted in FIG. 5 were generated using heparin as the IAIP ligand. The same samples evaluated using the competitive ELISA in FIG. 4 were also measured using this assay. The heparin-IAIP ELISA yielded an average IAIP concentration between 125 and 150 μg/mL in patients with sCAP and 422 μg/mL in healthy controls, and found differences between IAIP levels in subjects with sCAP and healthy controls that were more statistically significant than the differences observed using the competitive ELISA at all time points.
Figure 6:
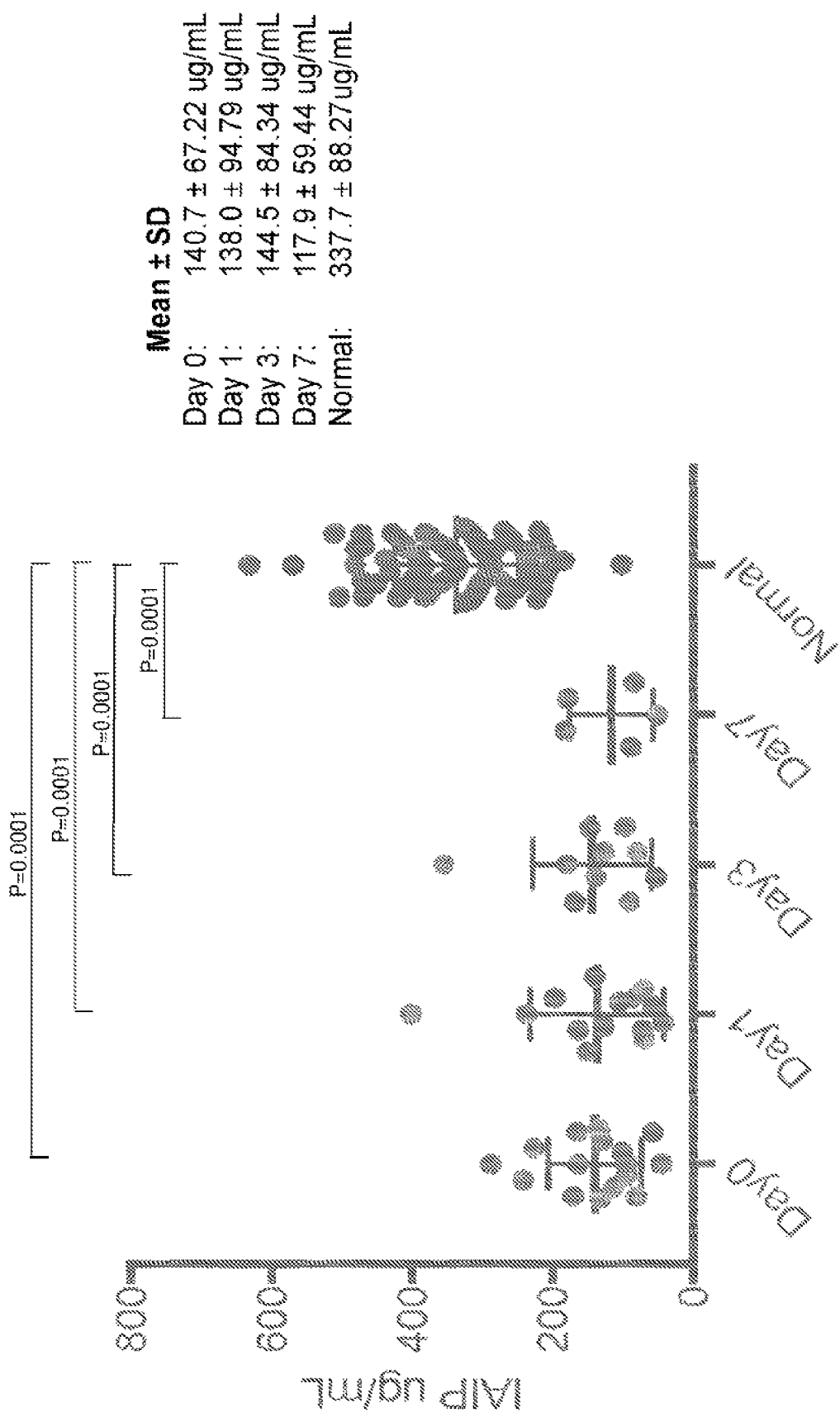
FIG. 6 is a graph showing measurements of IAIP concentration obtained using a "sandwich-type" ligand-IAIP ELISA as depicted in FIG. 3A. The results depicted in FIG. 6 were generated using LPS as the IAIP ligand. The same samples evaluated using the competitive ELISA in FIG. 4 and the heparin-IAIP ELISA in FIG. 5 were also measured using this assay. The LPS-IAIP ELISA yielded an average IAIP concentration between 118 and 145 μg/mL in patients with sCAP and 338 μg/mL in healthy controls, and found differences between IAIP levels in subjects with sCAP and healthy controls that were more statistically significant than the differences observed using the competitive ELISA at all time points. The LPS-IAIP ELISA performed comparably to the heparin-IAIP ELISA in terms of increased sensitivity and a more measurable difference between IAIP levels in subjects with sCAP and healthy controls.

Serial blood samples were collected from patients with a confirmed diagnosis of sCAP who were hospitalized in the Intensive Care Unit at Rhode Island Hospital. 16 patients were enrolled in the study and plasma was collected on days 0 (time of admission to the ICU), 1, 3 and 7. The level of IAIP was determined using the established competitive ELISA (FIG. 2A) and both sandwich-type ELISAs using biotinylated heparin or biotinylated LPS as detecting molecules (FIG. 3A). Blood samples from 95 healthy controls aged between 17 to 71 years old (obtained from healthy blood donors and purchased from Rhode Island Blood Center) were included in this study to compare IAIP levels in health controls to the levels measured in sCAP patients. The results are shown in FIGS. 4, 5, and 6.

The results indicate that IAIP levels were significantly lower in sCAP patients compared to healthy controls at the time of hospitalization and during disease progression (up to 7 days). Therefore, IAIP levels can be used to guide physicians in evaluating prognosis and making therapeutic decisions. Although the competitive ELISA showed decreased IAIP levels in sCAP patients, the "sandwich-type" ELISA assays using biotin-conjugated heparin and/or LPS as specific binding ligands yielded results that were more statistically significant (p value=0.0001 between IAIP level at day 0,1,3 and 7 compared to healthy controls). The "sandwich-type" ELISA assays using biotin-conjugated heparin and/or LPS also yielded a lower concentration of IAIP in sCAP patients, giving rise to a greater difference between IAIP levels measured in patients with sCAP and healthy controls. These data indicate that the "sandwich-type" ELISA assays using labeled IAIP ligands have increased sensitivity and potentially greater accuracy than competitive ELISA assays.

Figure 8A:
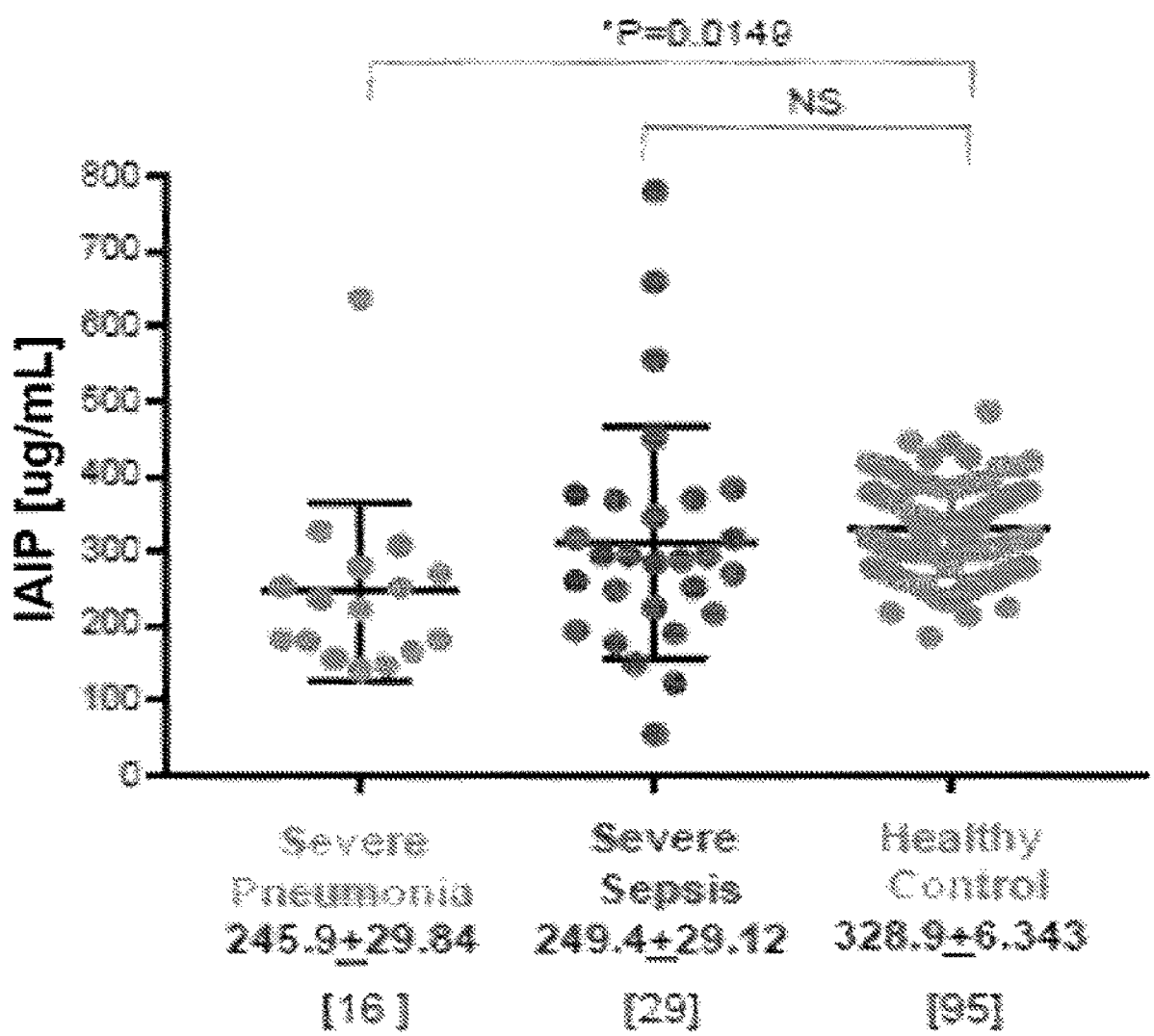
FIGS. 8A-8C are a series of graphs showing measurements of IAIP concentration obtained using a competitive ELISA as depicted in FIG. 2A and "sandwich-type" ligand-IAIP ELISAs as depicted in FIG. 3A. IAIP was measured in plasma samples from patients with severe pneumonia, severe sepsis, and in normal control subjects. Shown below each graph is the mean±SEM of IAIP concentration and the number of patient samples tested (in brackets).
Figure 8B:
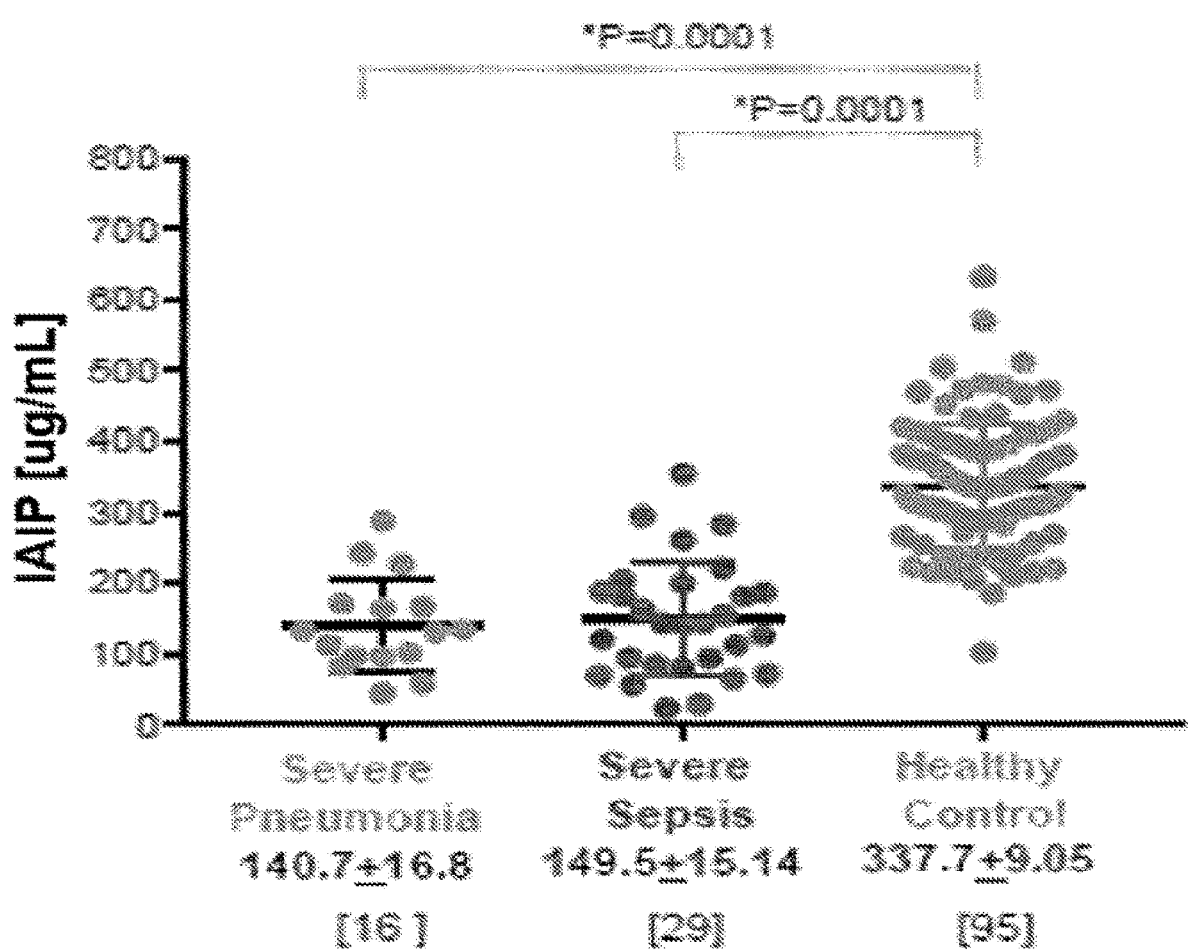
Figure 8C:
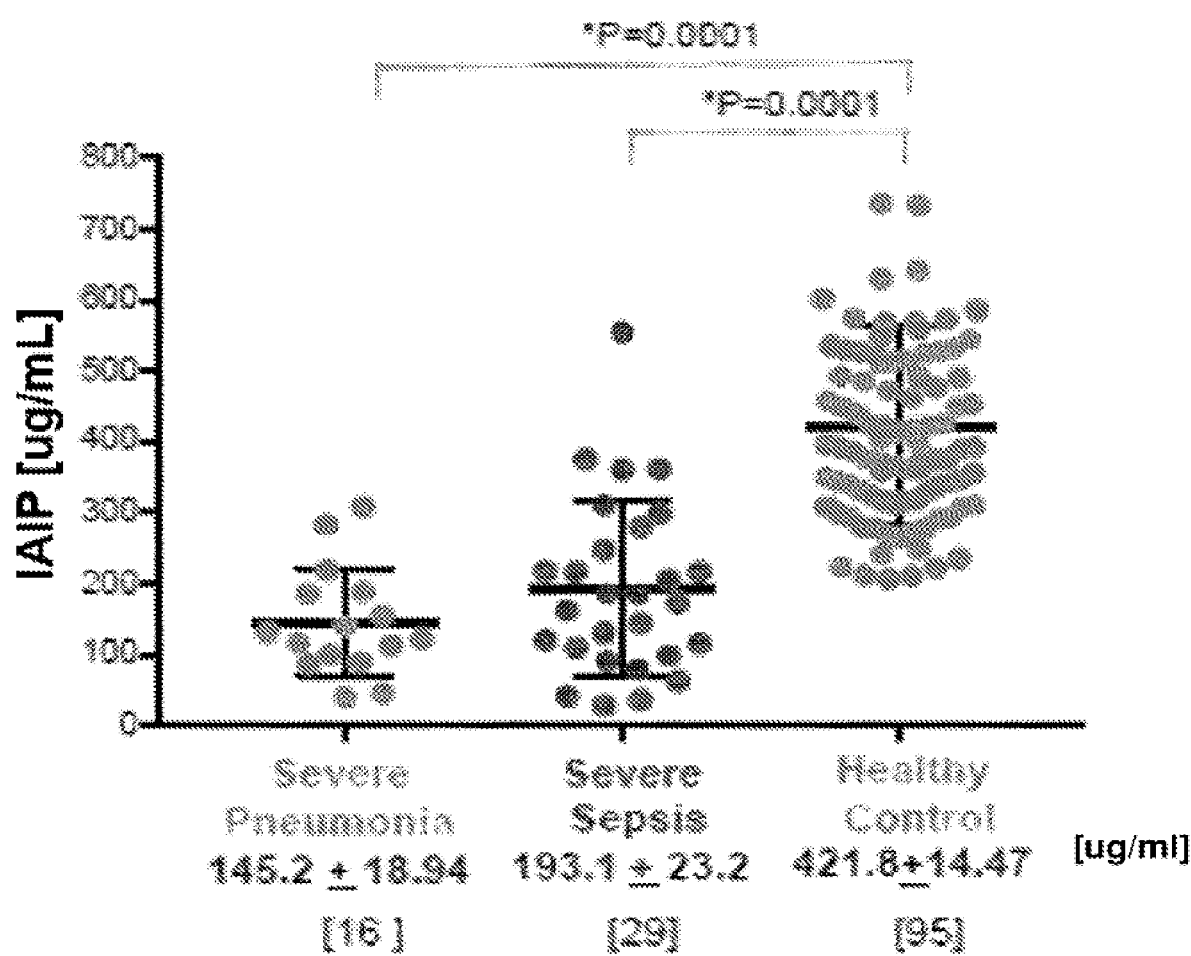

The same assays were also used to evaluate samples from subjects with sepsis that were admitted to the intensive care unit at Rhode Island Hospital. These assays yielded similar results. While the IAIP values of normal healthy controls are similar in the competitive ELISA (mean±SEM=328.9+6.34 µg/mL) and both the LPS or heparin-IAIP assay (337.7±9.05 and 421.8±14.47 µg/mL), the levels of IAIP in pneumonia and septic groups were significantly higher in the competitive ELISA, which resulted in statistically less significant differences or no difference between the diseased groups and healthy controls (FIGS. 8A-8C).

Example 4: Analysis of the Binding of Heparin to IAIP

The evaluation of the specific binding of heparin to IAIP was carried out using western blot analysis. Highly purified IAIP (1 µg), normal human plasma (1 µL), purified bikunin (Ulinastatin for Injection, Techpool, 2 µg) and human serum albumin (HSA, 2 µg) as a negative control were separated on a 7.5% SDS-PAGE gel and transferred onto a nitrocellulose membrane. Following blocking with 5% non-fat dried milk, the nitrocellulose membrane was incubated with biotin-conjugated heparin (1:500 in TBS) overnight at room temperature. After several washes with TBS+0.05% Tween, HRP-conjugated streptavidin (1:15,000) was added and incubated for 1 hr at room temperature. Following washing, the substrate Metal-enhanced DAB (Pierce) was added to visualize the reactive bands.

The biotin-conjugated heparin bound specifically to purified IAIP (250 kDa IαI and 125 kDa PαI) as shown in Lane 2 (FIG. 7), similar to MAb 69.26 (monoclonal antibody against human IAIP). In contrast to MAb 69.26 that bound to the light chain (bikunin) (lane 3), biotin-conjugated heparin did not bind to the light chain of IAIP, suggesting that heparin binds to IAIP via the heavy chain. The heavy chains of IAIP appear to be bound specifically to heparin.

Multiple reactive protein bands were detected by biotin-conjugated heparin in human plasma (FIG. 7, Lane 1) and binding to HSA was not detectable.

Moreover, free bikunin was not detected in the heparin-IAIP or LPS-IAIP ELISA, suggesting that only IAIP complexes with the intact heavy chain are measured using the heparin or LPS-IAIP ELISA. These data indicate that the sandwich-type ELISA using heparin and/or LPS (or other IAIP ligands) provides an assessment of the circulating IAIP complex in a subject (e.g., a subject with a pathological condition) that has increased accuracy and robustness relative to other known IAIP assays, such as the competitive IAIP assay (FIG. 2A).

Example 5: Binding of Biotinylated LPS to Immobilized Plasma-Derived IAIP

Figure 9:
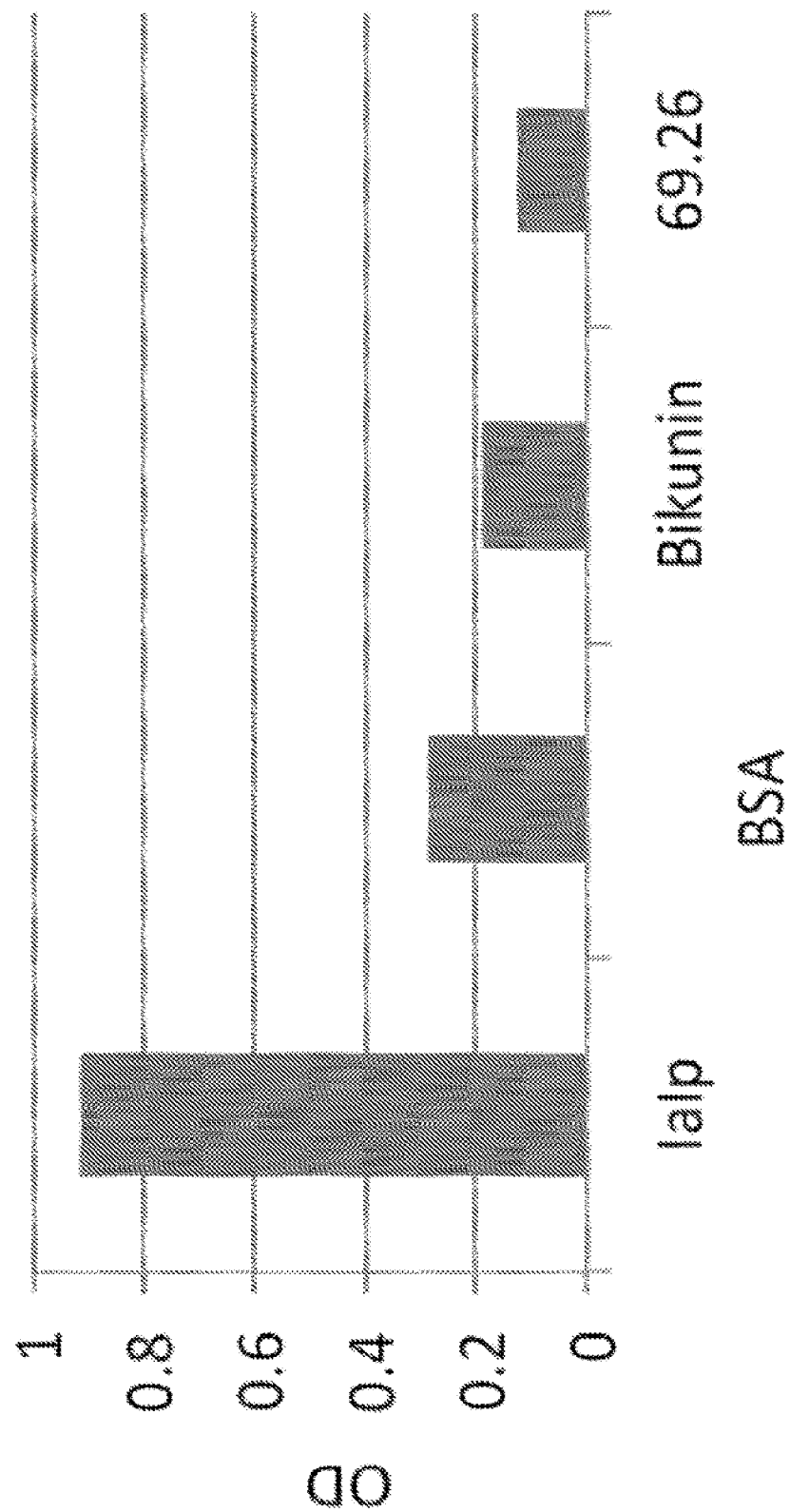
FIG. 9 is a histogram showing the binding of biotinylated LPS to immobilized plasma-derived IAIP, bovine serum albumin (BSA), and IgG of IAIP-specific antibody MAb 69.26. LPS demonstrated substantial binding to IAIP and little to no binding to MAb 69.26, which served as a negative control. Notably, LPS did not exhibit binding to the IAIP light chain, bikunin, indicating that the heavy chain of IAIP may facilitate binding to LPS.

To investigate the direct binding of LPS to IAIP in vitro, IAIP and other control proteins (BSA=bovine serum albumin; bikunin (the light chain of IAIP); and purified IgG of monoclonal antibody MAb 69.26) at 1000 µg/well were immobilized on a 96-well microplate (Greiner Microlon 600) and blocked with non-fat dried milk (5% in TBS+0.1% Tween 20). Following washing, 100 µg biotinylated LPS (Lipopolysaccharides from Escherichia coli O55:B5, purchased from Sigma, Cat #L2880) was added to each well and incubated in TBS+150 mM $CaCl_2$) buffer for 1 hr at room temperature. Following several washes with TBS+0.1% Tween, HRP-conjugated Streptavidin was added and incubated for 1 hr. Finally, TMB substrate was added and the reaction was stopped by adding 1 M HCl solution. The color change and absorbance were measured spectrometrically at 450 nm. Significant binding of biotinylated LPS molecules to IAIP was found compared to BSA, which served as a positive control, as it has been described to bind LPS (David S A, et al., Innate Immunity 1995; 2(2):99-106), or IgG of MAb 69.26 (negative control) (FIG. 9). LPS did not bind significantly to the light chain of IAIP (bikunin) suggesting that the heavy chain of IAIP facilitates the binding to LPS. The binding might also be mediated by the glycosaminoglycan chains.

Example 6: Binding of Biotinylated IAIP to Immobilized LPS

Figure 10:
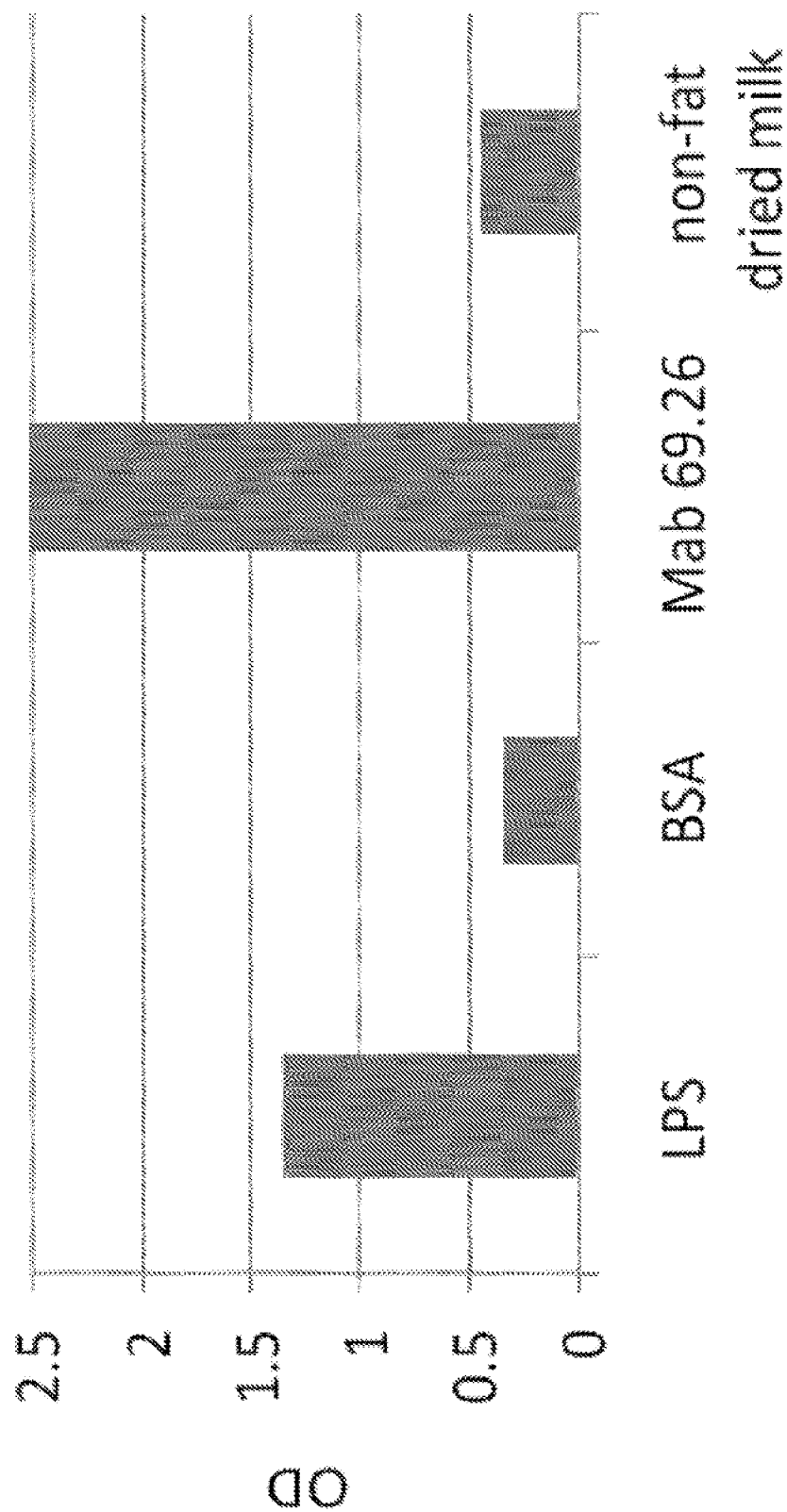
FIG. 10 is a histogram showing the binding of biotinylated IAIP to LPS, BSA, IgG of IAIP-specific antibody MAb 69.26, and non-fat dried milk. As expected, IAIP bound to MAb 69.26 and LPS and showed minimal binding to BSA and non-fat dried milk. These data confirm the results of FIG. 9.

In a reversal of the previous experiment, biotinylated IAIP (4 µg/well) was added and incubated for 1 hr to immobilized LPS (100 µg/well), BSA (2 µg/well), IgG of MAb 69.26 (2 µg/well) as a positive control, and non-fat dried milk (2 µg/well) as negative control (blank). Following several washes, HRP-conjugated streptavidin was added and subsequently TMB substrate was added to the microplate wells. Significant binding of biotinylated IAIP to immobilized LPS was detected, while significantly lower binding of IAIP to immobilized BSA or non-fat dried milk was observed FIG. 10). IgG of MAb 69.26 (monoclonal antibody specific to human IAIP) that served as a positive control in this experiment bound strongly to biotinylated IAIP.

Example 7: Analysis of pH Effects on IAIP-LPS Binding

To further characterize the binding of IAIP and LPS, similar solid phase binding experiments were carried out.

Figure 11:
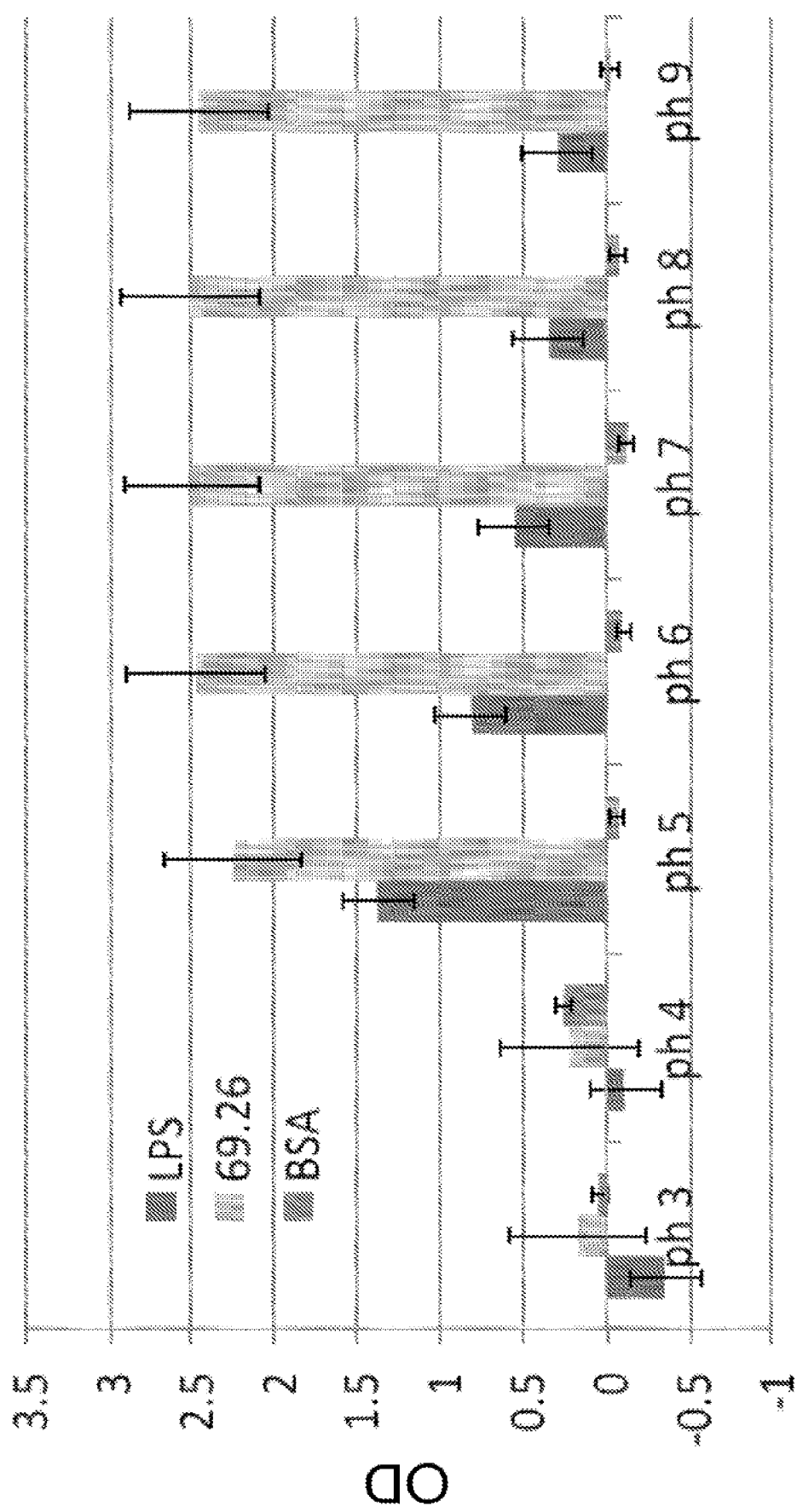
FIG. 11 is a histogram showing the effect of pH on the binding of biotinylated IAIP to LPS, BSA, and IgG of IAIP-specific antibody MAb 69.26. These data demonstrate that IAIP bound most strongly to LPS at pH 5, with reduced binding at pH 6 and pH 7, and little or no binding at pH 8 or higher or pH 4 or lower. In contrast, IAIP bound to IgG of MAb 69.26 at pH 5-pH 9, but did not bind at pH 4 or below. As in previous experiments, IAIP did not bind to BSA.

Biotinylated IAIP was incubated with immobilized LPS, IgG of MAb 69.26 (positive control), or BSA (negative control) under various pH conditions. Acetate buffer (50 mM) was used for the low pH solution (pH 3-6) and Tris-HCl buffer (50 mM) was used to obtain a neutral or higher pH solution (pH 7-9). While biotinylated IAIP bound strongly at pH 5, the binding was not observed at pH 3 or 4 (FIG. 11). Decreased binding of IAIP was observed when pH was increased above pH 5. The binding of IAIP to its specific monoclonal antibody MAb 69.26 peaked at pH 7 but, interestingly, did not significantly change when pH was increased up to pH 9. Similarly, at pH 3 and 4, IAIP binding to the monoclonal antibody was negligible. There was no binding observed between biotinylated IAIP and BSA. The results clearly suggest that the optimum binding between IAIP and LPS occurs at a range of pH 4-7, and in particular, at about pH 5.

Example 8: Analysis of the Effect of Salt Concentration on IAIP-LPS Binding

Figure 12:
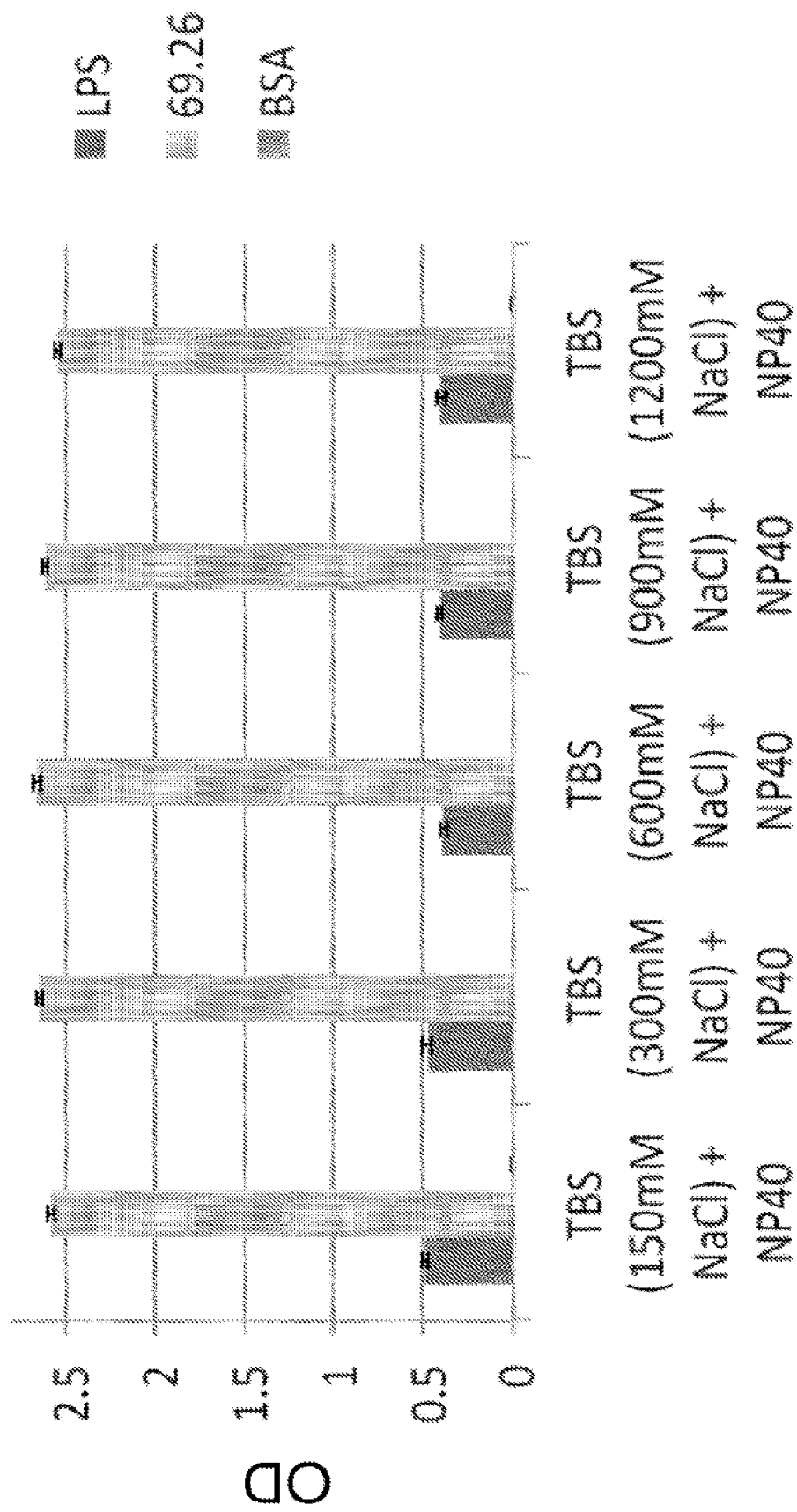
FIG. 12 is a histogram showing the effect of salt (NaCl) concentration on the binding of biotinylated IAIP to LPS, BSA, and IgG of IAIP-specific antibody MAb 69.26. These data show that the binding of IAIP to both LPS and MAb 69.26 was unaffected by salt, indicating strong and specific binding. No binding to BSA was observed at any of the salt concentrations tested.

The effect of salt concentration was investigated by adding increasing amounts of salt (NaCl) to the buffer during the incubation of biotinylated IAIP with the immobilized LPS on the microplate. The binding of IAIP to LPS decreased with increasing salt concentration, however the decrease was not significant even at a salt concentration of 1200 mM, suggesting that the binding of IAIP to LPS was relatively strong and specific, similar to the specific binding of IAIP to the monoclonal antibody (MAb 69.26) against human IAIP which was used as the positive control in this experiment (FIG. 12).

Figure 13:
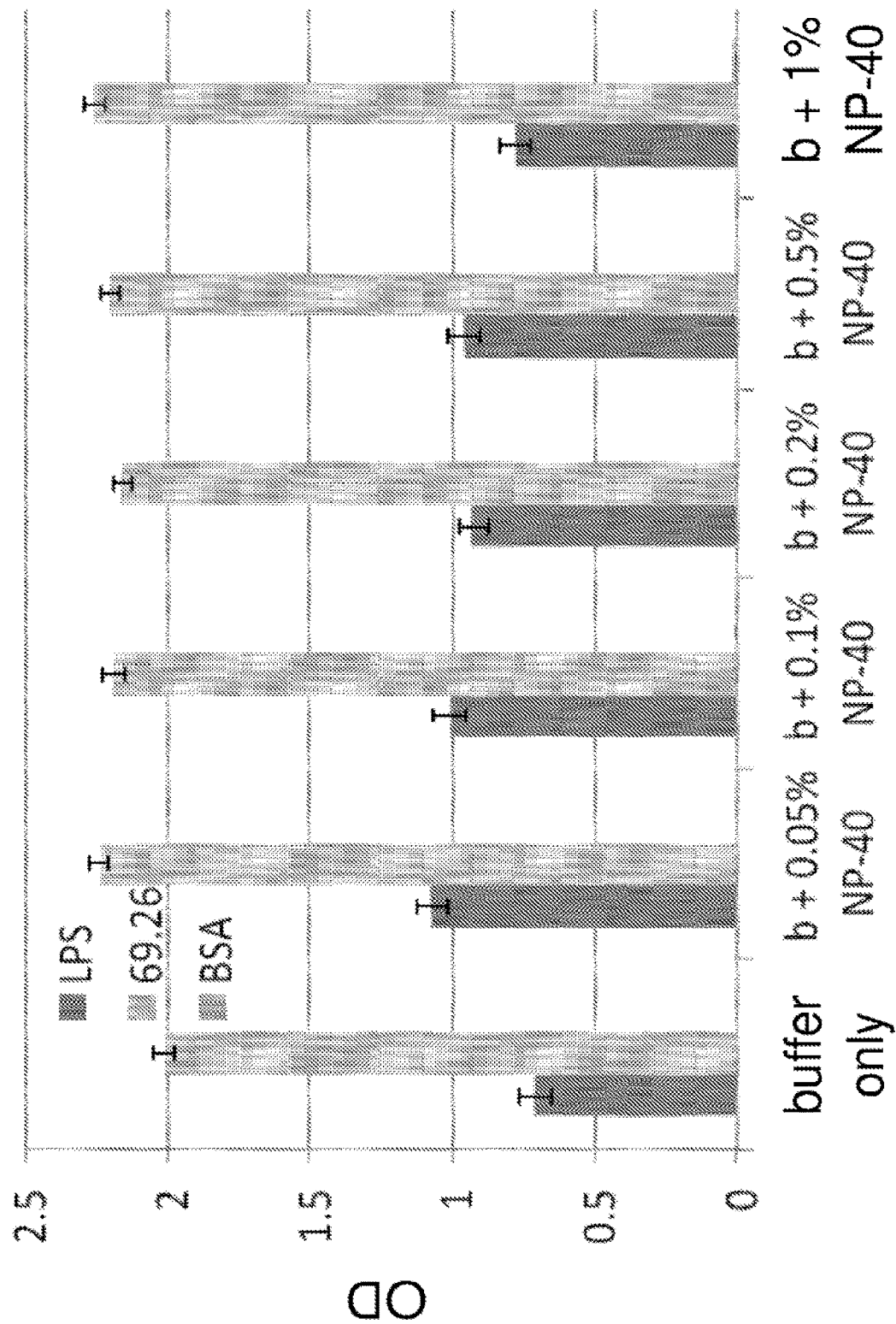
FIG. 13 is a histogram showing the effect of non-ionic detergent NP-40 on the binding of biotinylated IAIP to LPS, BSA, and IgG of IAIP-specific antibody MAb 69.26. Binding of IAIP to LPS was enhanced by the addition of 0.05% NP-40, and was still observed in the presence of 1% NP-40, indicating a strong binding interaction. No binding to BSA was observed at any of the NP-40 concentrations tested.
Figure 14:
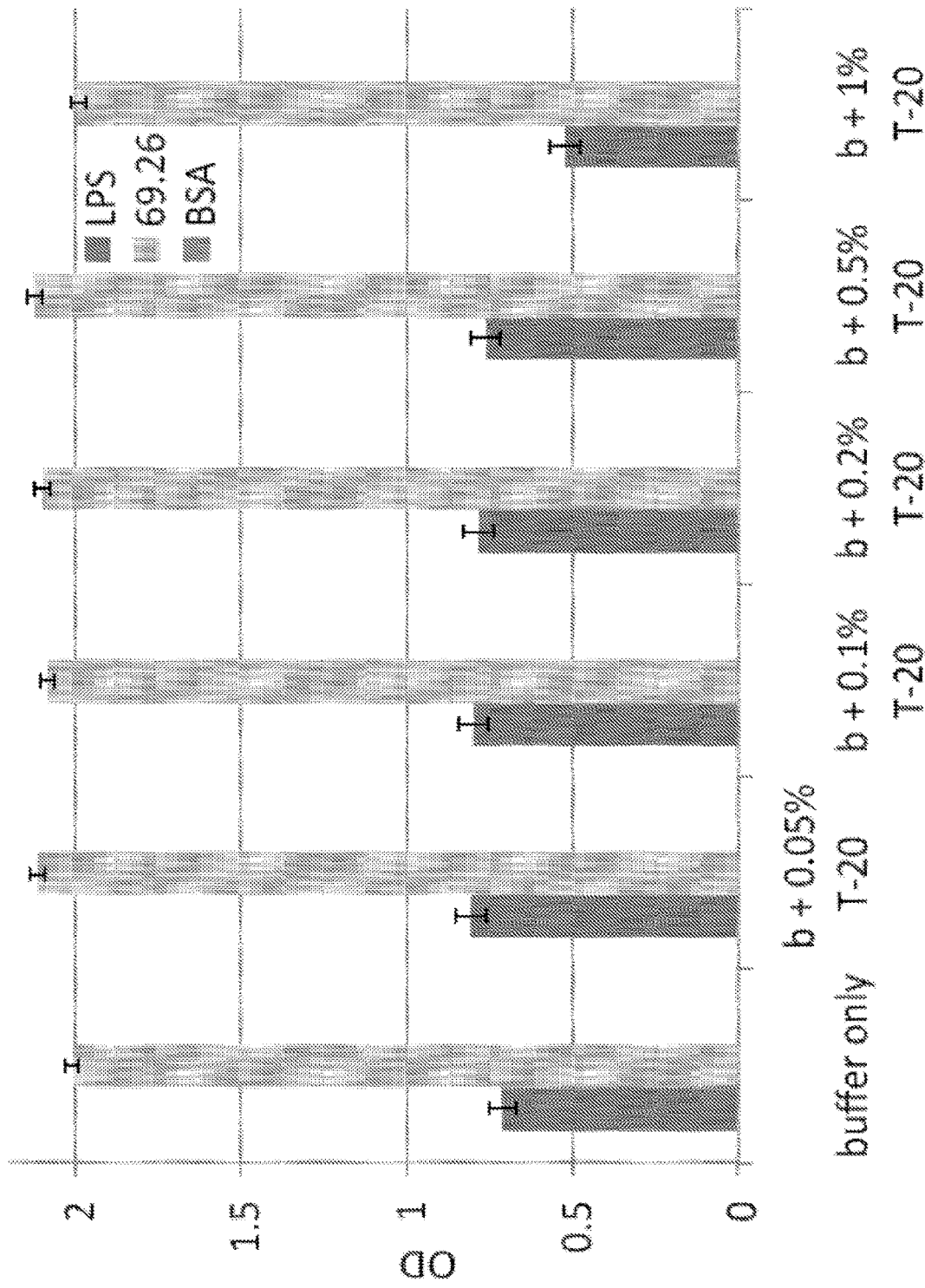
FIG. 14 is a histogram showing the effect of non-ionic detergent Tween-20 on the binding of biotinylated IAIP to LPS, BSA, and IgG of IAIP-specific antibody MAb 69.26. Binding of IAIP to LPS was enhanced by the addition of 0.05% Tween-20, and was still observed in the presence of 1% Tween-20, indicating a strong binding interaction. No binding to BSA was observed at any of the Tween-20 concentrations tested.

Example 9: Analysis of the Effect of Non-Ionic Detergents (NP-40 and Tween-20) on IAIP-LPS Binding Further investigation was carried out to study the effects of increasing concentrations of non-ionic detergents nonyl phenoxypolyethoxylethanol (NP-40) (FIG. 13) and Tween 20 (FIG. 14) on the binding of biotinylated IAIP to immobilized LPS. Increased binding was observed when 0.05% (w/w) NP-40 or Tween-20 was added to the binding reaction of IAIP to LPS, compared to TBS buffer alone without the addition of detergent. The low amount of detergent might facilitate the binding to LPS, suggesting that the lipid binding domain of the LPS molecule might be involved in this interaction. Even when the amount of the detergent was increased up to 1%, the binding of IAIP was still relatively strong as most of the IAIP was still bound to LPS indicating a strong interaction between IAIP and LPS in vitro. Similarly, biotinylated IAIP strongly bound to MAb 69.26 with high specificity and affinity and the addition of detergent up to 1% did not significantly change the binding. In contrast, the negative control (BSA) did not show any binding to IAIP.

Example 10: Quantification of IAIP Using a Rapid Lateral-Flow Immunoassay (LFIA)

The methods described herein can be used for the rapid quantification of IAIP using a lateral-flow immunoassay (LFIA). The "sandwich type" IAIP ELISA described and used in Examples 1-3 can be adapted to LFIA, a point-of-care (POC), rapid, reliable, quantitative and user-friendly test that can be used to identify high-risk subjects (e.g., infants, adolescents, or adults) with life threatening, severe inflammatory conditions (e.g., neonatal sepsis (NS) and necrotizing enterocolitis (NEC)). The LFIA can a) measure a linear range between 20 and 700 µg/ml IAIP; b) exhibit high precision (e.g., variability or error of <5%) for IAIP levels near 150 µg/ml (e.g., about 100 to about 200 µg/mL); c) obtain results in an hour or less (e.g., 15 minutes or less, such as less than 10, 7, or 5 minutes or less); and d) require a small sample volume<150 µL of plasma or whole blood samples (e.g., 150, 100, 75, 50, 25, 15, µL or less).

The test can be used to quickly identify a dysregulated inflammatory response in subjects (e.g., preterm newborns, infants, adolescents or adults). It is known that early intervention is important for improving survival in patients experiencing an inflammatory disease or condition or an infection.

In newborns, for example, the ability to apply early intervention protocols is often limited by the difficulty in identifying such conditions (e.g., NS and NEC) from other less serious diseases. The excellent negative predictive value of IAIP can help guide clinicians to make difficult decisions, such as, e.g., early termination of antibiotic treatment in a subject (e.g., an infant, an adolescent, or an adult) in whom current tests are uninformative. Furthermore, as therapeutic proteins, IAIP might be beneficial in critically ill subjects (e.g., infants, adolescents, or adults) and the blood levels can serve as a useful theranostic marker to help physicians make informed decisions about a replacement therapy with IAIP or other adjunctive therapeutic agents and to monitor disease progression.

A rapid point-of care test based on IAIP that can be used to influence therapeutic decisions, such as initiation and duration of treatment (e.g., antibiotic treatment), using a simple, user-friendly and portable device with accurate quantitative results readable within a short time period (e.g., 15 min. or less) is not only innovative, but also clinically useful to help reduce morbidity and mortality.

The LFIA involves adding a sample from a subject to a test strip (e.g., cellulose, glass fiber, or nitrocellulose), which is then pushed into the strip using a buffer. The strip contains an IAIP binding agent (e.g., an IAIP-specific antibody or an IAIP ligand). The labeled detection agent (e.g., an IAIP-specific antibody or an IAIP ligand) can be added to the strip before, after, or concurrently with the sample, and visualized using standard methods for the rapid quantification of IAIP.

a) Gold-conjugated reagents: Gold nanoparticles can be used to label the reagents in the (LFIA) format due to its superior colloidal stability. A stable formulation of gold nanoparticles that are functionalized with hydrazides are commercially available (Innova Bioscience). While usually antibodies are covalently attached to colloidal gold as detecting reagents, heparin or LPS can be similarly conjugated via their sugar chains using the InnovaCoat Gold nanoparticles. The gold conjugation of LPS and heparin can be performed in a small scale and tested for their stability and performance in the LFIA.

b) Optimization of capture, detection, sample reagents and conditions of the LFIA: Building upon the experience with the competitive LFIA development described below, the formulation and coating conditions of MAb 69.26 on the capture line and other factors, such as blocking agents, surfactants, and carbohydrates, can be selected to reduce non-specific binding and to improve flow characteristics. The optimal dilution factor and suitable diluent that reduces interference and non-specific binding can also be determined. Multi-factorial design of experiments (DoE) can be used to determine the interaction of the following parameters: 1) binding agent concentration, 2) coating pH and buffer type (range=4-10), 3) coating duration and 4) type of blocking agent (e.g., bovine serum albumin, fish gelatin, etc.).

c) Test strip components, housing and reader: The test strip can be housed in a plastic cassette with sample well and test read windows placed over the appropriate areas of the strip. A variety of standardized strip dimensional configurations can be used. A suitable housing can be chosen, such as one that is adaptable to the Detekt or ESEQuant reader. The composition of sample and conjugate pad, as well as the pore size of the nitrocellulose membrane, can be selected to achieve a desired rate of capillary action, and hence, reaction time of the sample with detector reagent.

LFIA performance goals can be optimized by changing, e.g., the formulations and processes for the striping conditions of the Test line reagent, the conjugation method of the detecting molecules (e.g., LPS or heparin), and the titration of the detection agents, as well as the optimal material and dimensions of pads and wicks, as described below:

a. Optimization of Test and Control Lines. Membrane stripping conditions can be optimized for both Test Line (MAb 69.26) and Control Line (LPS-binding proteins or heparin-binding proteins (for e.g. clotting factor IX) of the test strip. A 30 minute at 37° C. drying period can be used to immobilize the Test and Control Lines, as robust manufacturing procedures for LFIA membranes. Multi-factorial DoE can be used to determine the interaction of the following membrane stripping parameters: 1) binding agent concentration, 2) pH and buffer type (range=pH 4-10), 3) salt concentration and 4) striping volume (1-3 µL/strip) and inkjet speed. Incorporating membrane striping improvements from initial optimization studies. Multi-factorial DoE can also be used to determine the efficacy of membrane co-coating with various concentrations (0-1 µg/strip) of protein blockers, surfactants, carbohydrates, and other agents which may reduce gold particle non-specific binding or improve flow characteristics of the membrane. Based on our solid phase binding studies, LPS and heparin bind significantly stronger to IAIP at pH lower than 5. Similar conditions can be used in the LFIA.

b. Optimization of test strip parameters. The composition of the sample pad and conjugate pad, as well as the pore size of the nitrocellulose membrane, can affect the rate of capillary action, and hence, reaction time of the sample with gold detector reagent, and thus, can be selected to achieve desired results. We have determined that a fast flow NC (HF090, Millipore) met design specifications for sensitivity and time to result. DoE can be used to assess types of filter, and pad and wick materials for the assay. Similarly, the size and geometry of the sample pad and conjugate pad can be adjusted to achieve desired results.

The sample pad can be optimized to: 1) accept undiluted sample, 2) provide the necessary formula to minimize non-specific binding and 3) accept whole blood samples. The competitive IAIP prototype rapid test discussed below utilized a diluted sample (1:5), which mitigated the need for raw sample volume entering the test strip and contained blocking proteins and surfactants that mitigate non-specific binding issues. A formulation-based sample pad (e.g., dried formula) can be developed for components (e.g., protein blockers, surfactants, etc.) and their concentrations. There are available immunoassay additives that may be used to effectively and reliably reduce interferences and non-specific binding. Screening studies of candidate agents can be followed by multi-factorial DoE to determine the optimal concentrations of, e.g., blocking agents.

Conjugation techniques for LPS and heparin can be evaluated for use with gold colloid (nanoparticles) and dyed latex particle-based conjugation techniques.

c. Blood separation filtration membrane and plastic housing cassette. In addition to the dried sample pad formula, an in-line blood separation filter membrane suitable for excluding red blood cells can be adopted for whole blood samples. The goal is to simplify the process and make the testing of the rapid test format user friendly, especially for the off-laboratory applications at point-of-care, such when using directly applied whole blood collected from finger prick or via collection tube. Multiple types of these blood filters are commercially available, such as Vivid™ or Cytosep™ membranes (PalI) or other manufacturers (GE Lifesciences) and can be used in the LFIA. The plastic housing dimensions for the test strip can be selected for use with a reader (e.g., a Detekt reader).

We have determined that the hand-held Detekt™ reader model RDS-150 PRO (Detekt Biomedical, Austin, TX) can be used in the LFIA. Detekt's optical lateral flow reader technology for rapid test readers is currently used in commercial diagnostic devices in food and beverage safety testing, bio-threat detection, environmental monitoring and animal health. The reader is a hand-held device that optically scans the test strip and compares the Test and Control line signal strength to a programmed calibration algorithm. The signal integration software can be customized to interpret the IAIP dose-response curve, and this algorithm can be resident on Detekt™ units. The Vision Suite Pro developer's kit software program can be used in collaboration with the manufacturer, Detekt Biomedical LLC in Austin, TX, to integrate the interpretation of the IAIP test strip with the Detekt reader. A software algorithm based on IAIP binding curve shape and internal controls can be developed to perform the following functions: a) to establish the shape of the IAIP binding curve relative to Test Line signal intensity; b) to establish an internal control, possibly based on Control Line signal, to correct for day-to-day variability of test strip runs and c) to establish the software for kit lot-specific information to be incorporated into the reader (e.g. via bar code scanning).

The performance of a developed and optimized sandwich-type IAIP rapid test (according to the parameters discussed above and herein) can be evaluated in a pre-clinical setting. The LFIA cassette can be tested as follows:

a) Analytical sensitivity, reportable range and precision—Samples/controls of known IAIP concentrations spanning the probable range of IAIP concentrations (25-800 μg/mL) can be tested in multiple replicates over multiple days (N=10) by multiple operators (N=3 minimum). Data can be analyzed to establish precision at all spots of the IAIP binding curve, including precision of the assay cut-off point (set at 150 μg/mL).

b) Interfering substances—Sample pools of known IAIP concentrations can be spiked with potentially interfering substances to determine effects on dose recovery. The Clinical and Laboratory Standards Institute (CLSI) EP-07A protocol can be used for reference. Stock solutions of substances (e.g. hemoglobin, bilirubin, human IgGs, etc.) that may be found at high concentrations in patient samples can be spiked into IAIP samples and tested.

c) User robustness assessment—Sample pools of known IAIP concentration can be used to verify the robustness of the test strip to various scenarios/errors produced by end-users. Parameters tested include: 1) incorrect sample volume added (+25%), 2) laboratory environmental conditions (temperature 65-85° F.; humidity 10-70% RH) and 3) incorrect test strip read time (+50-100% recommended).

d) Product shelf-life stability—IAIP test kits can be stored under different temperature regimens (e.g., ambient and 37° C.) and tested using a set of IAIP controls of known IAIP concentration at various intervals post-manufacture (>1 year) to determine the stability of the product.

e) Sensitivity and Specificity in preliminary Clinical Samples—The product can be tested using clinical samples from in subjects (e.g., infants with suspected and confirmed diagnoses of NS and NEC).

To evaluate the IAIP rapid test in an observational clinical study, samples can be collected from subjects (e.g., subjects having or at risk for an inflammatory disease or condition or an infection) undergoing routine clinical evaluation and management. Acquisition of data from multiple centers caring for a broad, heterogeneous population of subjects with the same inflammatory disease or condition or infection can be used to provide an adequate number of study subjects and strengthen the association between IAIP and the disease or infection. The rapid, point-of-care bedside device that can provide IAIP levels in real time can aid in obviating the use of unnecessary interventions or the prolongation of unnecessary treatment (e.g., antibiotic therapy) and can reduce the length/cost of hospitalization.

The IAIP LFIA can be used for the clinical evaluation of subjects as follows:

1) Collection of blood samples: Samples can be collected from subjects having or at risk of developing an inflammatory disease or condition at a variety of medical centers. Clinical and demographic data can be recorded for all subjects, including age, weight, gender, and laboratory results. Serial samples from the same subjects collected at various time points (e.g., 0, 24, 48, 72 hrs. and 7d) can also be used in the LFIA. The LFIA could be used to determine whether IAIP levels correlate with the severity and progression of the disease, whether the IAIP level predicts risk or subsequent disease, and whether subjects will develop more severe disease or improve following therapy.

2) Power analysis: Preliminary data and published studies of subjects having an inflammatory disease or condition or an infection can be used for sample size estimates.

3) Blood Analysis: The collected clinical plasma samples can be transferred into study vials, labeled (deidentified), and stored in a frozen state until testing. IAIP levels are stable for 24 hours at room temperature, for up to 14 days under routine refrigerated clinical storage, and for an unlimited time at 20° C. IAIP levels can be analyzed using the LFIA rapid IAIP test and the sandwich-type IAIP ELISA for a comparison study.

To evaluate proof of concept for an IAIP rapid test LFIA, we produced test strip cassettes designed to measure IAIP using a competitive LFIA similar to that shown in FIG. 2A. The data produced using this immunoassay format, described below, confirm that a LFIA based on a sandwich-type format (similar to that shown in FIG. 3A) can be used, as well. The competitive LFIA is described below.

Sepsis and Systemic Inflammatory Response Syndrome in Neonates

Advances in intensive care have led to substantial improvement in survival of subjects, (e.g., infants, especially preterm, very low birth weight (VLBW) (<1,500 g) infants). Preterm infants, however are prone to opportunistic infections and the acute life-threatening conditions neonatal sepsis (NS) and necrotizing enterocolitis (NEC). A recent multicenter survey suggests that up to 21% of VLBW infants encounter at least one episode of late-onset (>72 hours of life) blood culture—proven sepsis and up to 7% of VLBW develop NEC. NS and NEC are associated with serious morbidity, including adverse neuro-developmental outcomes, and have a relatively high mortality in NS (10-30%) and NEC (16-42%). Early warning signs and symptoms of these neonatal diseases, are non-specific, frequently inconspicuous, and can easily be mistaken as due to non-infectious etiologies, such as exacerbations of bronchopulmonary dysplasia, apnea of prematurity, gastroesophageal reflux, or functional intestinal dysmotility. More disturbing is that the clinical deterioration in both diseases may progress in a fulminant manner resulting in shock, disseminated intravascular coagulation, and death within hours of clinical presentation. There are currently no rapid tests which broadly guide the physician as to the risk of patient progression to severe disease and death.

Although the exact cause of NEC is still unclear, it is widely believed that NEC pathogenesis results when infectious agents translocate across the intestinal epithelial layer, evade innate immune defenses and cause subsequent inflammation and tissue necrosis. Both NS and NEC are associated with systemic inflammatory responses. Their clinical presentation, which is non-specific and subtle at the initial stage, is very similar. Furthermore, NS and NEC often coexist in the same disease episode (for example, NEC with sepsis occurred in one-third of cases of NEC in the case-control studies). Immediate medical management with prompt antimicrobial treatment and supportive care are standard of care for both conditions. Thus, it is of practical and clinical importance to identify the risk of these potentially lethal conditions at the earliest opportunity.

A biomarker for early and accurate identification of an inflammatory disease or infection (e.g., NS and/or NEC) would be very useful to help physicians to make challenging decisions on initial use and continuation or early termination of antibiotic treatment in subjects (e.g., infants) in whom conventional tests are uninformative. Unfortunately, there is currently no widely-available biomarker that is clinically useful and effective in the management of these challenging diseases. Recently procalcitonin (PCT) has been approved as a biomarker to help manage antibiotic treatment in patients with lower respiratory tract infections and sepsis but this marker is specific only to bacterial infection and is not sensitive in detecting systemic inflammatory conditions caused by viral or other non-bacterial infections. Furthermore, the use of PCT test is still controversial in pediatric patients especially in preterm infants during the first few days of life. Thus, a sensitive biomarker that provides information on the severity of the inflammatory disease process would be clinically useful in the management of inflammatory diseases or infections (e.g., NS and NEC in preterm infants). This remains a major challenge.

Comparison Studies of the Predictive Value of IAIP with Other Markers in Detecting Infants with Systemic Inflammation and in a More 'Localized' Disease (Spontaneous Intestinal Perforation)

We confirm that IAIP is an excellent severity biomarker and that it can differentiate NEC from a more focal inflammatory disease, Spontaneous Intestinal Perforation (SIP). The IAIP test outperforms CRP in diagnosis of NEC from SIP.

Figure 15A:
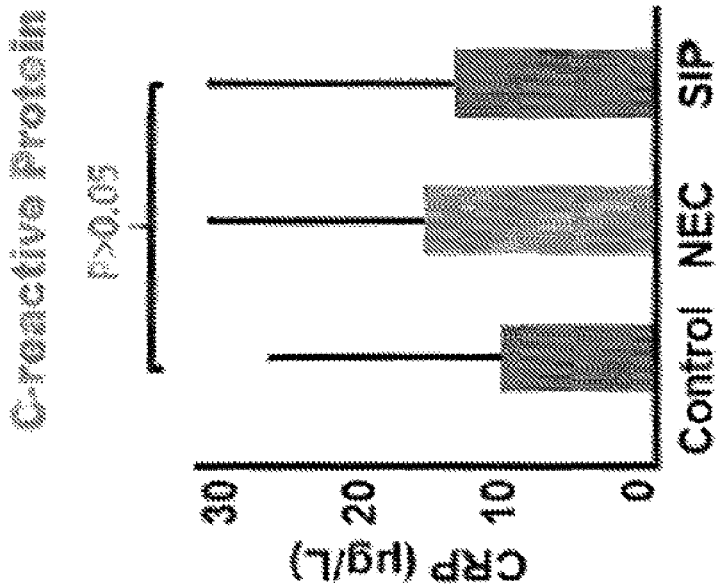
FIGS. 15A-15B are histograms depicting blood IAIP level (FIG. 15 A) and CRP (FIG. 15 B) in infants with NEC (n=14) and SIP (n=13) as well in gender, weight and gestational age-matched healthy controls (n=26) at initial presentation. Decreased IAIP levels were found in infants with proven NEC (mean±SD: 139±21 ug/mL) while the levels in healthy controls (276±110 ug/mL) or infants with SIP (319±72 ug/mL) were significantly higher ($p<0.05$ and $p<0.005$). In contrast, no statistically significant difference between IAIP levels in infants with SIP and controls ($p>0.4$). When CRP levels were tested, no significant difference was found between SIP, NEC and control group ($p>0.05$).
Figure 15B:
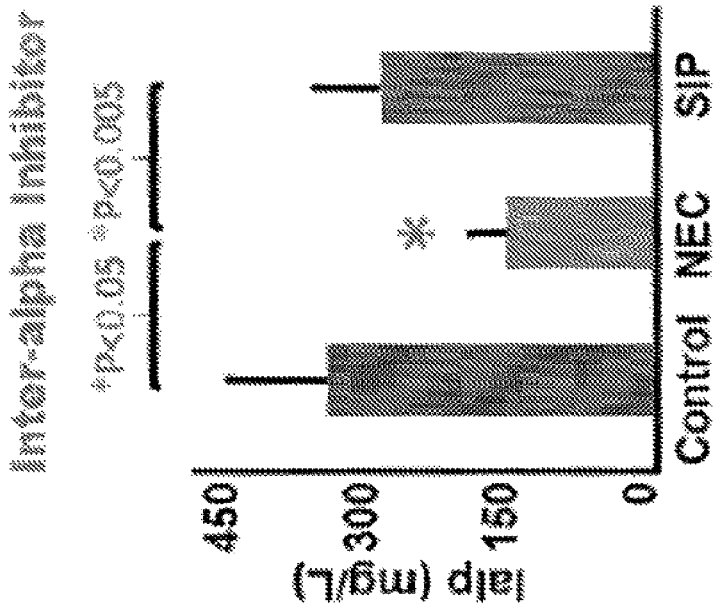
Figure 16A:
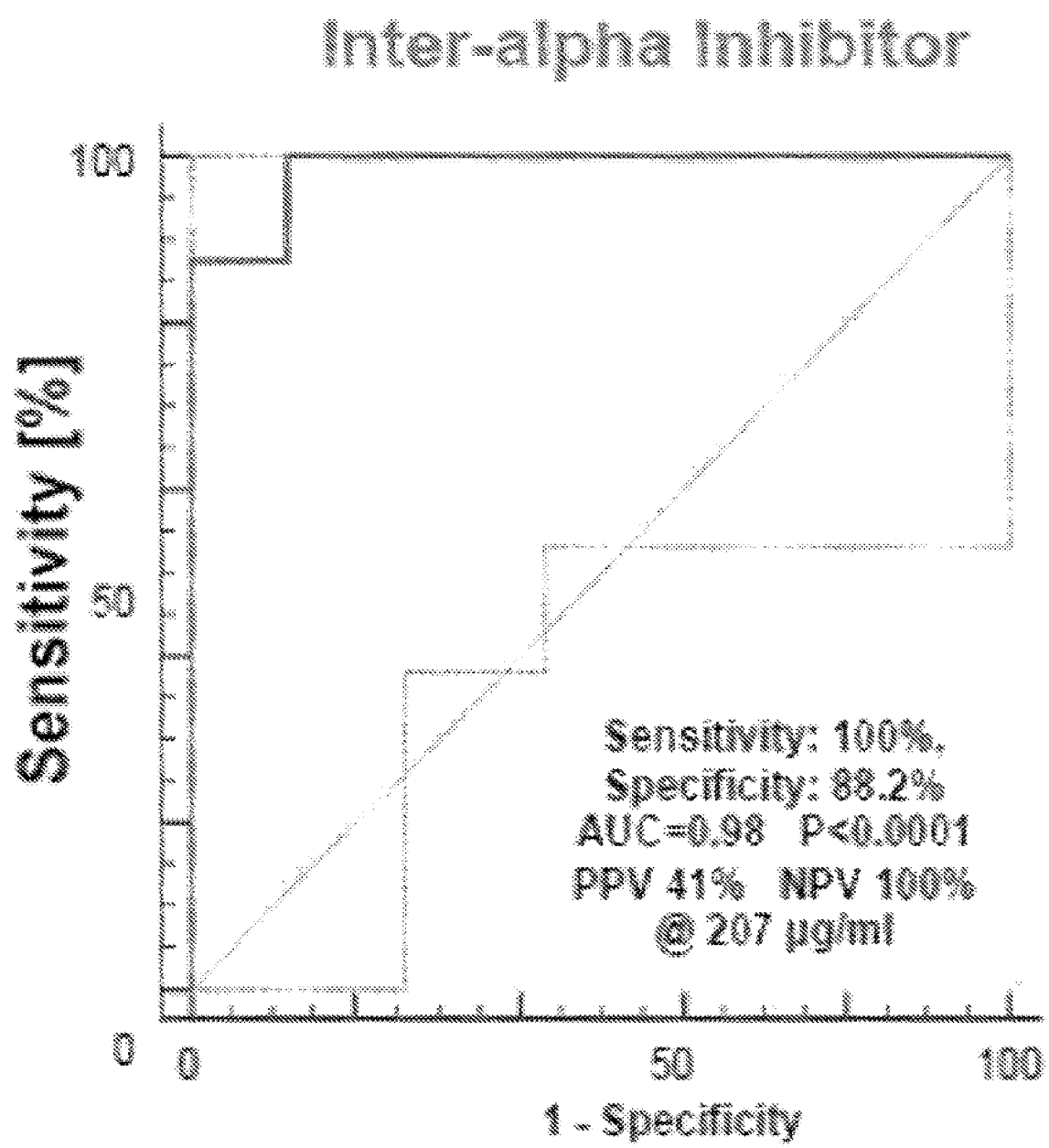
FIGS. 16A-16B are graphs depicting ROC curves of IAIP and CRP in NEC infants. The predictive value of IAIP level is superior with sensitivity of 100%, specificity of 88.2%, PPV 41% and NPV 100%, (FIG. 16A) compared to CRP (FIG. 16B) with sensitivity of 100%, specificity of 64.7%, PPV 18% and NPV 98%.
Figure 16B:
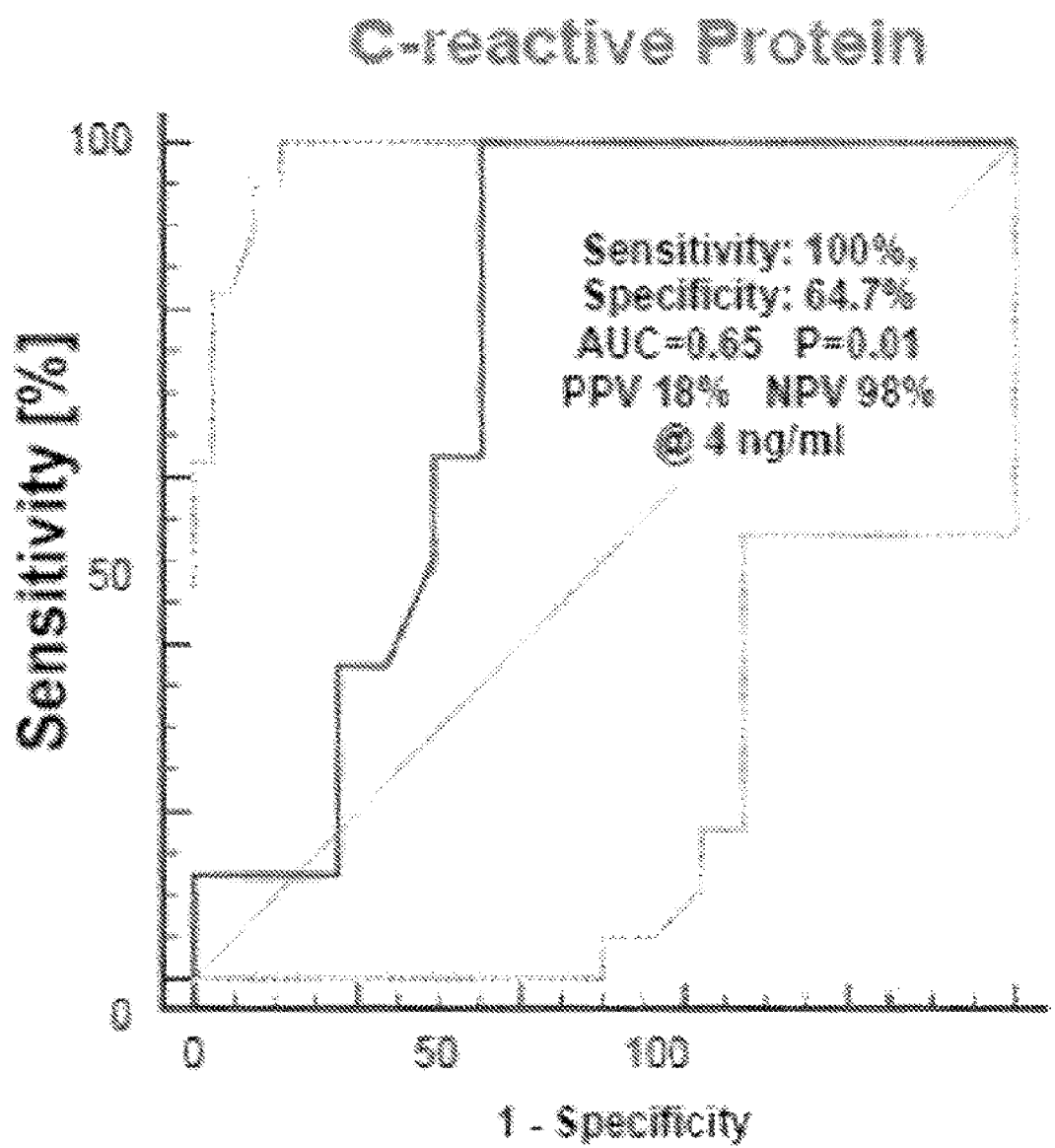

IAIP can discern disease severity, e.g., a local inflammatory response (SIP) vs systemic and potentially life threatening inflammatory responses (NEC and NS). We collected blood samples from 95 infants (64 female and 31 male) suspected of neonatal sepsis (NS), Necrotizing enterocolitis (NEC) and Spontaneous intestinal perforation (SIP) at Women & Infants' Hospital in Providence, RI Serial samples were also collected when available from each individual patient. Most of the infants were <30 weeks gestation age (ranging from 23-31 wks.) with mean birth weight of 1235 grams. From these collected samples, we obtained 8 infants with proven NEC, 9 infants with SIP and 20 infants with NS. As we have previously used the IAIP assay to determine the positive and negative predictive value for NS, we assessed the predictive value of IAIP levels in systemic inflammatory diseases conditions such as NEC and in a more 'localized' and focal necrotic disease condition, such as SIP. We also compared the levels of IAIP and another inflammatory biomarker C-reactive protein (CRP) in these infants against gender, weight and gestational age matched controls. The competitive ELISA using a single monoclonal antibody specific against human IAIP (MAb 69.26) was used to measure the level of blood IAIP and the CRP ELISA kit was used to analyze the CRP level in blinded fashion. A significant decrease in IAIP levels was found in infants diagnosed with NEC (modified Bell's stage II or higher) compared to healthy infants ($p<0.05$) and infants with SIP (with no radiographic NEC, $p<0.005$). However, no significant difference was found between infants with SIP and the healthy controls. In contrast, increased levels of CRP were found in both infants with NEC and SIP, although the increase was not statistically significant ($p>0.05$) (see FIGS. 15A-15B). Furthermore, the receiver operating characteristic (ROC) of CRP at a cutoff value of <4 generated the area under curve (AUC) of 0.65 ($p=0.01$, 95% C1; 0.54-0.90) with sensitivity of 100%, specificity of 64.7%, positive predictive value (PPV) of 18.7 and negative predictive value (NPV) of 100; while ROC of IAIP at a cutoff value of <207 mg/L yielded robust AUC of 0.98 ($p<0.0001$, 95% C1; 0.84-0.99). The predictive value of IAIP was superior compared to that of CRP with sensitivity of 100%, specificity of 88.2%, PPV of 41, and NPV of 100 (FIGS. 16A-16B).

Figure 17:
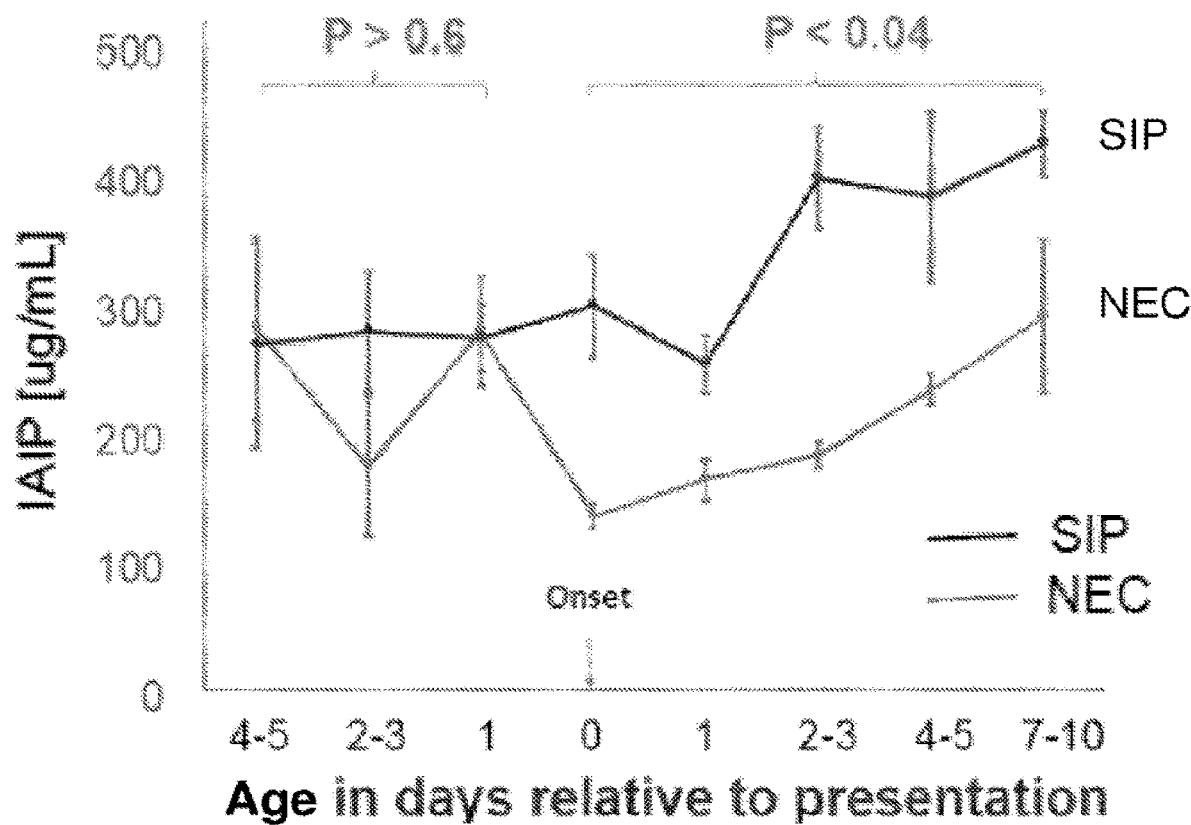
FIG. 17 is a graph depicting the result of longitudinal studies of plasma IAIP levels in infants with NEC (n=8) and SIP (n=9). Blood was collected serially at the time before and after the onset of the disease presentation. No significant difference in IAIP levels was found in both infant groups with SIP and NEC before the disease onset (p value>0.6), but IAIP levels in infants with NEC were significantly lower compared with the levels in infants with SIP ($p<0.04$) up to 10 days after the onset.

Multiple serial samples from infants were available from some but not all infants before and after the onset of NEC and SIP. We further analyzed the IAIP levels using the established IAIP competitive ELISA. The IAIP levels in infants with NEC were significantly lower compared to the level found in SIP patients (FIG. 17) at diagnosis and following the initiation of treatment. These were convenience samples that were only available from residual blood collections. These results demonstrate that IAIP level is a useful biomarker that identifies life threatening systemic inflammatory conditions such as NEC (in addition to NS) with high sensitivity and specificity, and IAIP levels appear to also distinguish NEC from the less life-threatening conditions in SIP patients. The IAIP test demonstrated excellent NPV both in NEC (100%) and NS (98%). The IAIP test can be used to guide treatment (e.g., antibiotic treatment) decisions, such as early termination in infants in whom conventional tests are uninformative.

Figure 18:
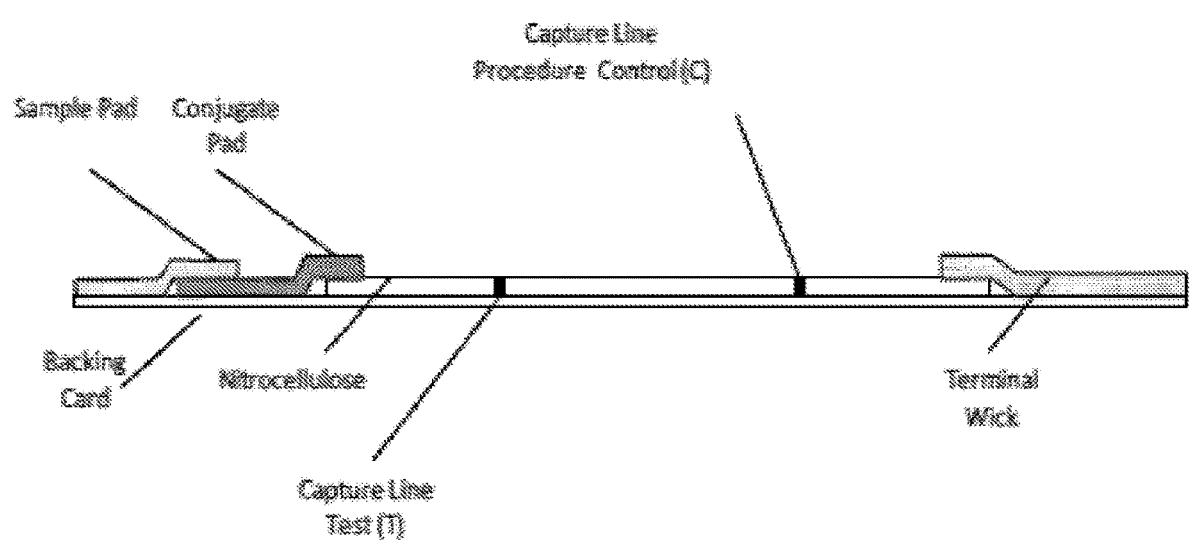
FIG. 18 is a schematic of a lateral flow immunoassay-based IAIP rapid test.
Figure 19:
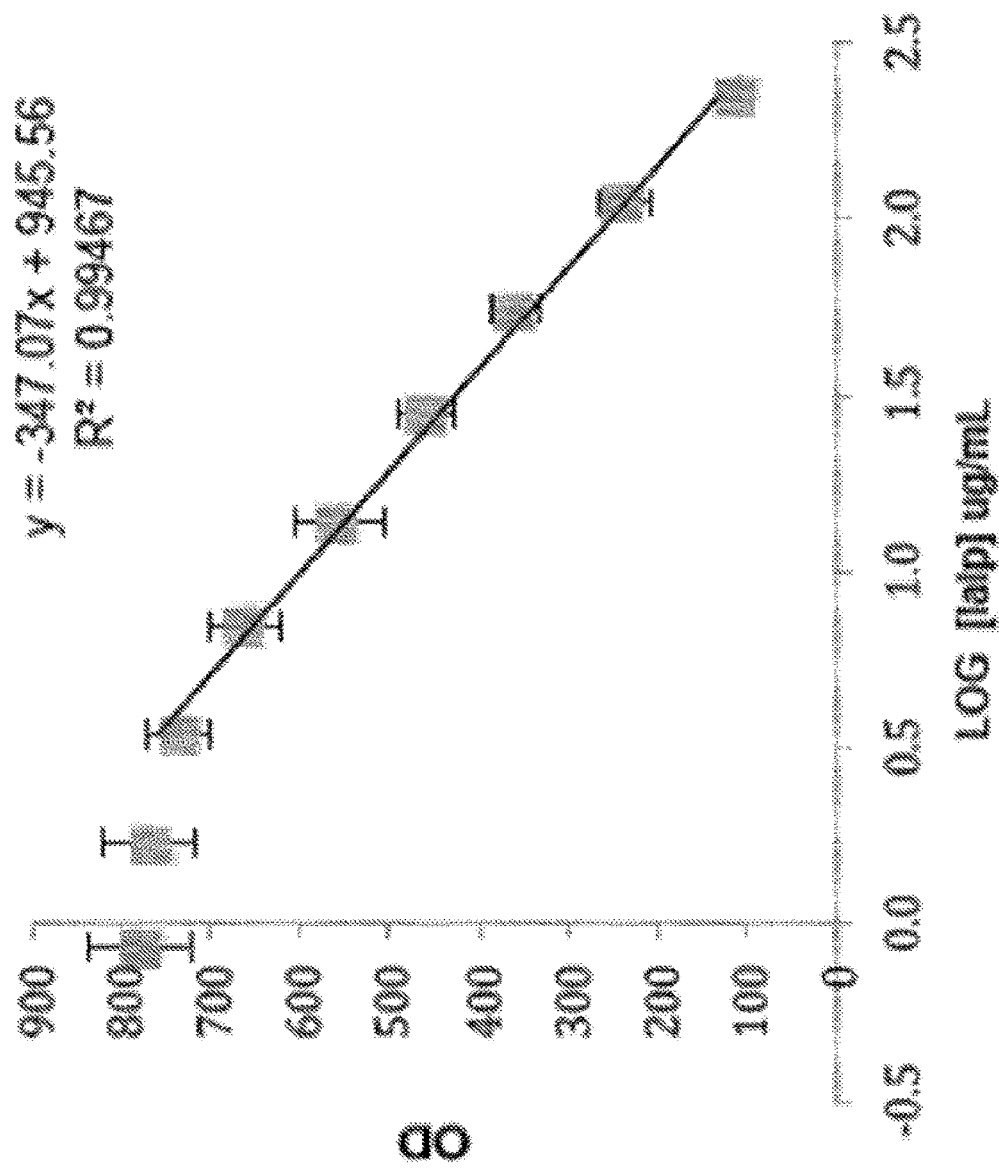
FIG. 19 is a graph depicting the standard curve of the rapid IAIP test using an ESEQuant reader. The value of each points were plotted as the mean+SD of a total of 13 independent analysis. The rapid test standard curve is suitable for plasma samples with IAIP level that ranges from 17.5 to 1100 μg/mL.

Prototype Development of a Quantitative Competitive Lateral Flow Immunoassay (LFIA) for IAIP that Measures Blood IAIP Level and Detects NS and NEC a) Choice of test format and assay architecture: A lateral flow immunoassay-based test was chosen for the format of IAIP rapid test (see FIG. 18). An LFIA offers many advantages when developing a rapid point-of-care assay as they are designed to: 1) use small sample volumes; 2) follow well characterized kinetics and offer rapid intervals to test results; 3) be analytically sensitive and precise; 4) commonly contain an internal control to verify proper performance of the device; 5) be made from raw materials that are well characterized and widely available; and 6) produce signals that can be quantitatively analyzed using a strip reader. Thus, LFIA, as an IAIP rapid test, can be used, e.g., at a point-of-care setting.

b) Optimization of capture, detection and sample reagents and conditions of the LFIA:

Initial efforts were successful in adopting the established competitive IAIP ELISA to the competitive LFIA format by optimizing the capture, detection, sample reagents and conditions of the lateral flow immunoassay. We further established a dose-response curve, as well as evaluated the timing of signal, precision, and repeatability of the rapid IAIP assay format. A reader-based data analysis of test results were initially adopted using a Qiagen test strip reader. Following these initial tests, we have proceeded to optimize the test strips and assay conditions, and test several portable readers that available and suitable for our test strips.

c) Purified IAIP and monoclonal antibodies against IAIP (MAb 69.26): Both reagents are key components used in the competitive assay format. We have developed and optimized a scalable bioprocess method for isolation of IAIP from human plasma that results in high yield and high purity. The hybridoma cells were grown in scalable CELLine culture flasks (Integra Bioscience) for large scale production of antibodies in vitro. The IgG was isolated from the hybridoma supernatant by affinity Protein A chromatography.

d) Test strip: Multiple pilot lots of strips were prepared and the chosen formula is a stable platform for the quantitative measure of IAIP in human plasma: 1) Sample pad: cellulose pad with buffer and surfactant; 2) Conjugate pad: glass fiber pad with anti-IAIP (MAb 69.26) gold conjugate and rabbit IgG gold conjugate (Control Line); 3) Nitrocellulose: Fast flow (Millipore HF090) nitrocellulose with IAIP striped (Test Line) and goat-anti-Rabbit IgG striped (Control Line Terminal wick: cellulose pad (no formula)).

e) Sample: A small volume of plasma (15 µl of 1:5 diluted samples) was added to strip then 115 µl chase buffer to push sample through strip. The chase buffer had been optimized: 2 mM Tris pH 8.0+100 mM NaCl+0.5% Brij+0.05% Tween 20+1.0% Fetal Calf Serum. Brij surfactant was added to the buffer to facilitate a rapid clearing of the conjugate from the upstream portions of the strip f) Running time: Strips were run with plasma samples or IAIP calibrators (at three different concentrations) and then quantified by the Qiagen reader at 10, 15, 20, 25, 30, 45 and 60 minutes after sample addition. The strip ran in about 7 min (i.e., nitrocellulose had cleared of extraneous gold) and could be read any time after that. We found that after 15 min the signals did not change dramatically. Thus, we read the strips uniformly at 15 min after the samples were added.

g) Calibrators and Controls: Human plasma (Rhode Island Blood Center) with a known IAIP value based on the ELISA results was used as calibrator and internal standard control. Different doses were created by diluting the plasma with 1% FCS-containing buffer. Using a portable Qiagen test reader (ESEQuant LFR) we established a standard curve that ranged from 17.5 to 1100 µg/mL (using 1:5 sample dilution). Reproducibility of calibration curves across days was tested by repeating and running a set of the calibrators up to 13 times at different times of the day over 5 days. The results are shown in FIG. 19. The mean and the SD of each of the values were plotted. The results show that the test demonstrated a tight spread over the 5 day period with an excellent coefficient of variance (CV less than 15%).

h) Test strip readers and software: As our IAIP rapid test is intended to be quantitative, we carefully selected a reader to capture the signal generated by the test strips. Various types of test strip readers are commercially available. The choice of reader was based on features and specifications such as engineering, ergonomics, and software robustness. Since this is an important part of the rapid test, we tested three different readers with different technologies and features for IAIP rapid test strips: 1) a portable tabletop lateral flow reader (ESEQuant LFR by Qiagen); 2) a handheld PDA based reader Detekt RDS 1500 Pro (Detekt Biomedical, Austin, TX) and 3) Smart Phone/tablet based reader system (iCalq reader—iCalq, Salt Lake City, UT). We found that the Detekt reader produced a better linear curve ranging from 5 to 700 μg/mL than the other readers tested.

Determination of Inter- and Intra-Assay Precision of the Optimized Assay

The inter-assay precision characteristics of the rapid test were determined using collected blood samples (n=6) run repeatedly for 6 consecutive days. The results were read subsequently using three different portable and handheld readers and the coefficient of variance (CV) was calculated from the results obtained from each individual samples. The CV of the IAIP rapid test using ESEQuant reader ranged between 4 to 16% with an average of 13%, while the Detekt reader demonstrated an average CV of 10% (ranging from 5-16%) and the iCalQ smart phone based reader resulted in an average CV of 16% (ranging from 10-23%). The Detekt reader performed better with a relatively lower CV than the other two readers we tested. In order to evaluate the intra-assay precision of the test, we ran 8 plasma samples and analyzed IAIP levels based on the optimized protocols. The signal obtained from each sample was read three times on the various readers and IAIP values were calculated individually based on the established standard curves. Subsequently, the CV was determined from the triplicate readings and was found to range between 2 to 8% with an average CV of 5% for all three readers tested.

Performance Assessment of the Rapid Assay in Infant Plasma

Figure 20A:
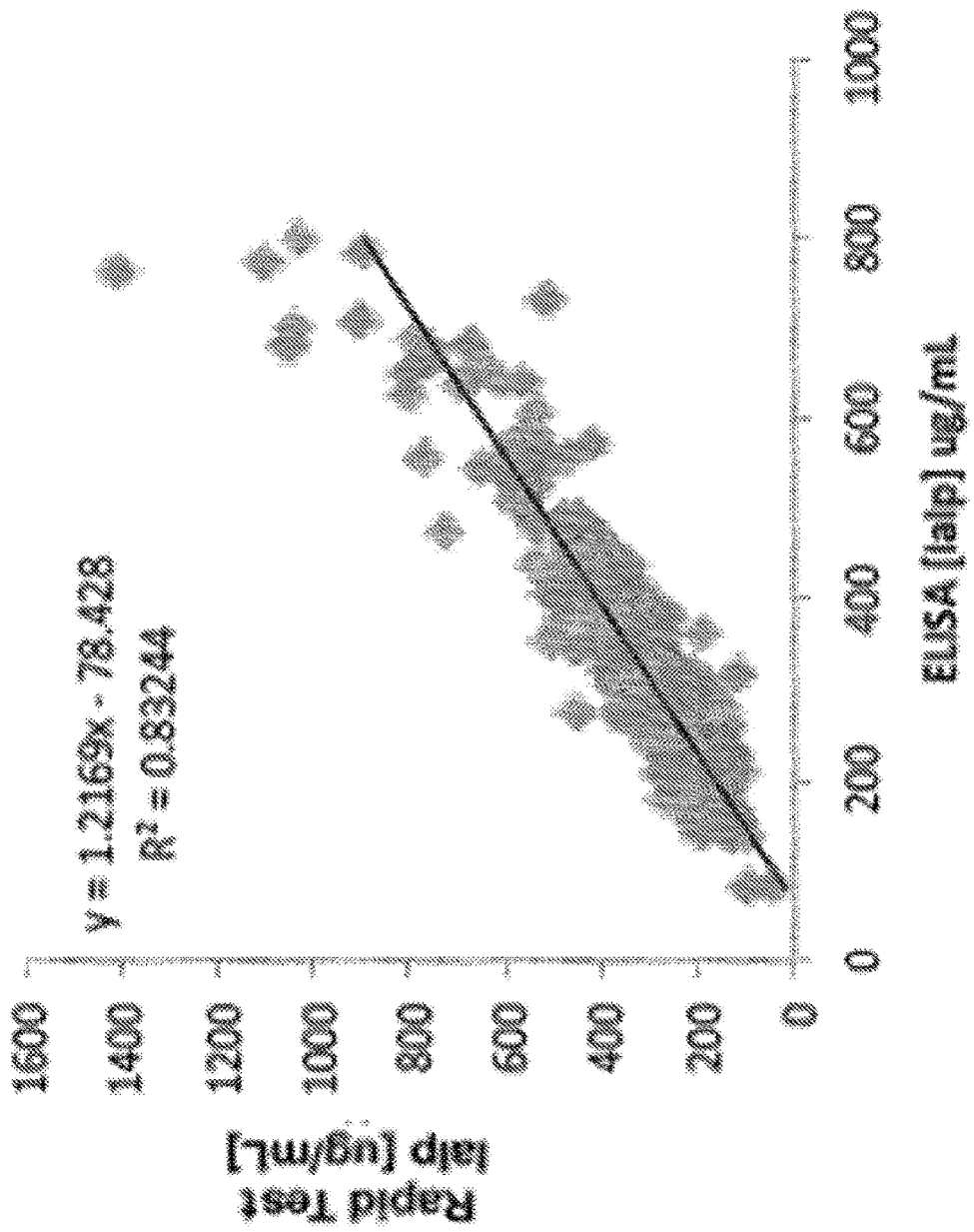
FIGS. 20A-20C are a series of graphs depicting the correlations between the results obtained by an IAIP rapid test using ESEQuant reader, Detekt reader, iCalQ reader and the results obtained by the established competitive ELISA format.
Figure 20B:
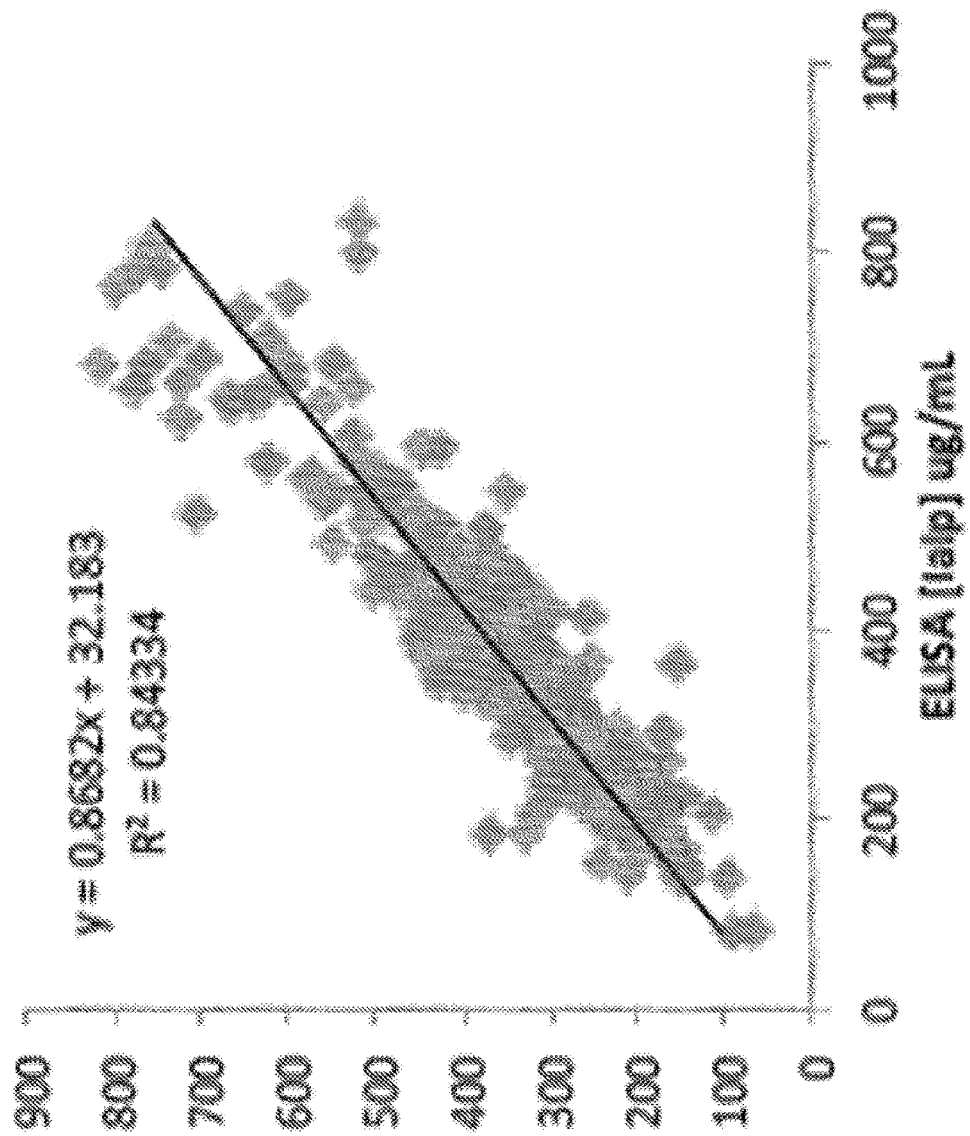
Figure 20C:
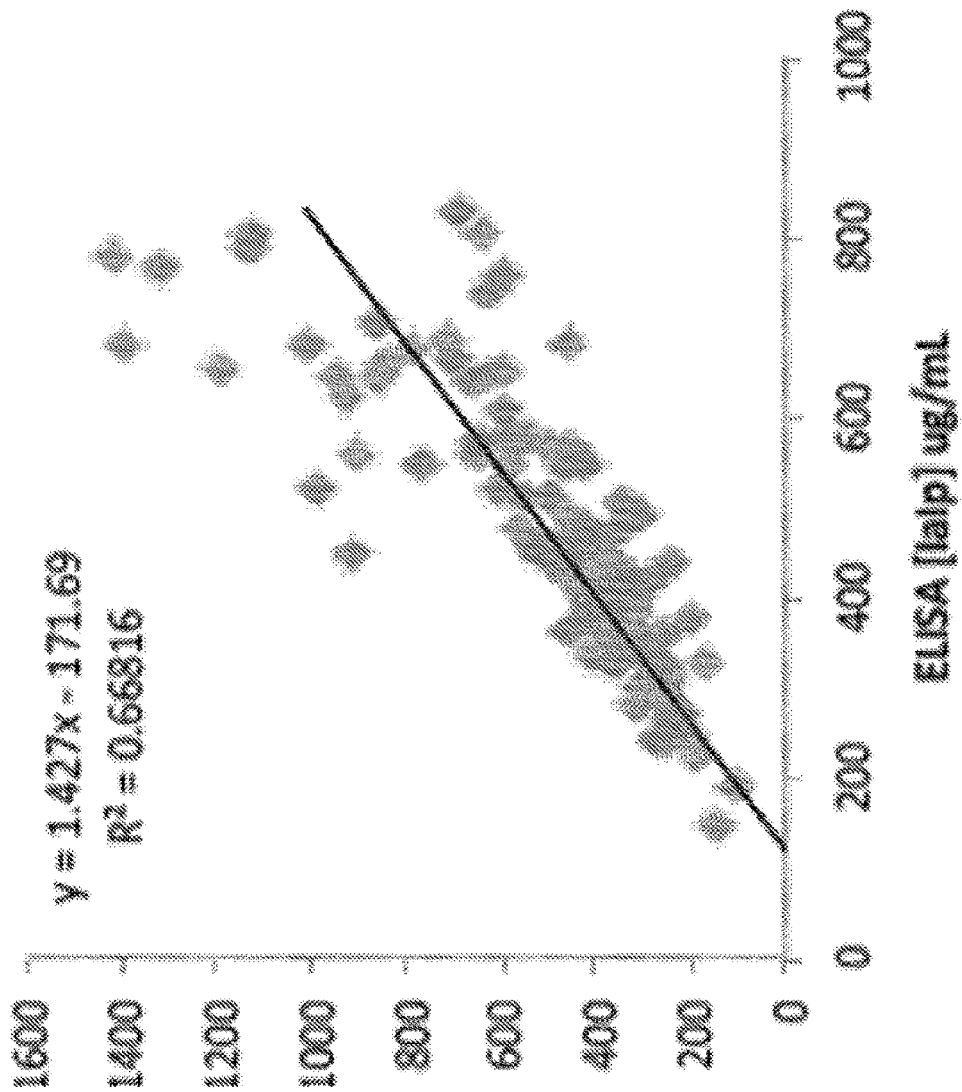

Using the samples collected from infants at Women & Infants' Hospital, we carried out the analysis of IAIP based on the optimized conditions for the IAIP test strips described above. The resultant signals were read sequentially using three independent readers and the results were calculated based on the respective standard curve of the readers. The results of the rapid tests were compared with the results obtained by the established competitive ELISA assay and the values of each individual sample were plotted against the results of the rapid test (FIGS. 20A-20C). The results demonstrated an excellent correlation between the 6 hr competitive ELISA and the rapid competitive LFIA test results that were generated within 15 minutes by using the ESEQuant reader (Correlation coeff. R2 of 0.832, n=311) and Detekt reader (R2=0.84, n=339). However, the iCalQ smart phone based reader produced test results that were less comparable with the ELISA results, especially in the samples containing a high level IAIP (>600 μg/ml).

In summary, we successfully converted a 6 hour laboratory-based competitive ELISA into a point-of-care IAIP rapid test that is capable of measuring circulating IAIP in blood (ranging from 10-800 μg/mL) accurately (correlation coefficient R2>0.8 compare to the ELISA results) within 15 minutes with acceptable intra- and inter-assay precision (less than 20% CV). We confirmed that blood IAIP level is a useful predictive marker not only for NS, but also for NEC with high sensitivity (100%) and high specificity (88%). The IAIP test is more specific in detecting NEC than the CRP test and IAIP level is also useful in distinguishing NEC from SIP patients.

Given the successful adaptation of the competitive assay to the LFIA format, we expect that the "sandwich-type" IAIP ELISA described herein (e.g., as shown in FIG. 3A) can also be adapted to LFIA format. Rapid quantification of IAIP can lead to early identification of subjects (e.g., human subjects, such as infants, children, adolescents, or adults) having or at risk of developing an inflammatory disease or condition or an infection (e.g., sepsis, NEC, bacterial infection, or another disease or condition) and timely initiation of optimal therapy.

Example 11: Hyaluronic Acid-IAIP Solid Binding Assay

Hyaluronic Acid, sodium salt (Sigma-Aldrich), was dissolved in $dH_2O$ (stock concentration of 1 mg/mL) and further diluted into 20 mM $NaHCO_3/Na_2CO_3$ buffer at pH 9.0. Fifty, 100 and 200 ng hyaluronic acid per well was immobilized on a 96-well microplate (Greiner BioOne, Microlon 600) at 37° C. for 120 minutes. Following blocking with 5% Non-fat Milk Powder in TBS-T (20 mM Tris-buffered saline solution at pH 7.3+0.05% Tween-20 (v/v)) at 37° C. for 60 minutes and 3 washes with TBS-T, serially diluted solution containing IAIP (human plasma and highly purified IAIP in TBS) was added to the microplate and incubated at 37° C. for 60 minutes. Human plasma was prepared by cryo-precipitation of fresh frozen plasma obtained from a local blood bank. The cryo-supernatant was used in this experiment and had an IAIP concentration of 250 μg/mL. The purified IAIP was at a starting concentration of 1 mg/mL. The microplate was then washed 3 times with TBS-T, and biotin-conjugated MAb 69.26 (monoclonal antibody against human IAIP) at 1:1000 dilution in TBS was added and incubated at 37° C. for 30 minutes.

Figure 21A:
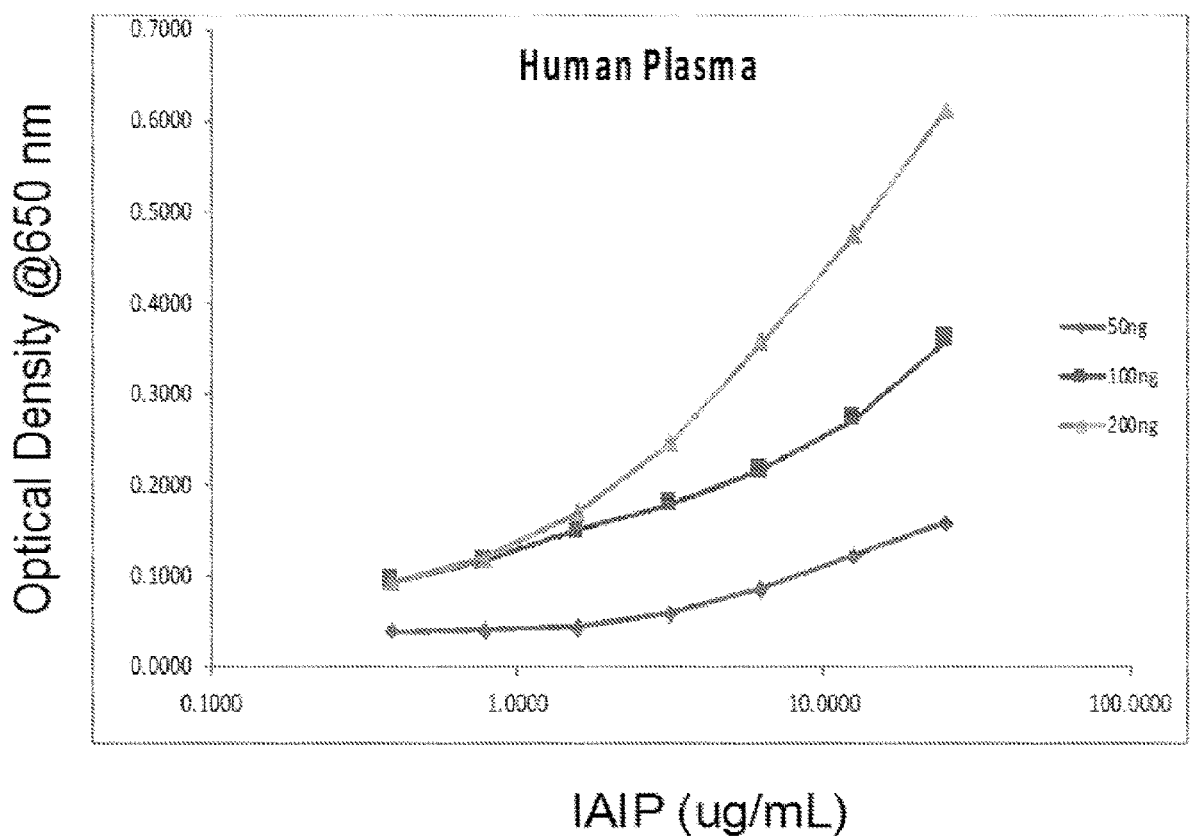
FIGS. 21A-21B are a series of graphs depicting the quantification of IAIP using a "sandwich-type" ELISA in which hyaluronic acid is immobilized on a 96-well plate to capture IAIP, and IAIP is detected using biotin-conjugated MAb 69.26 (a monoclonal antibody against human IAIP). The assay can be used to quantify IAIP in serial dilutions of both human plasma (FIG. 21A) and purified IAIP (FIG. 21B) using 50 ng, 100 ng, or 200 ng hyaluronic acid per well.
Figure 21B:
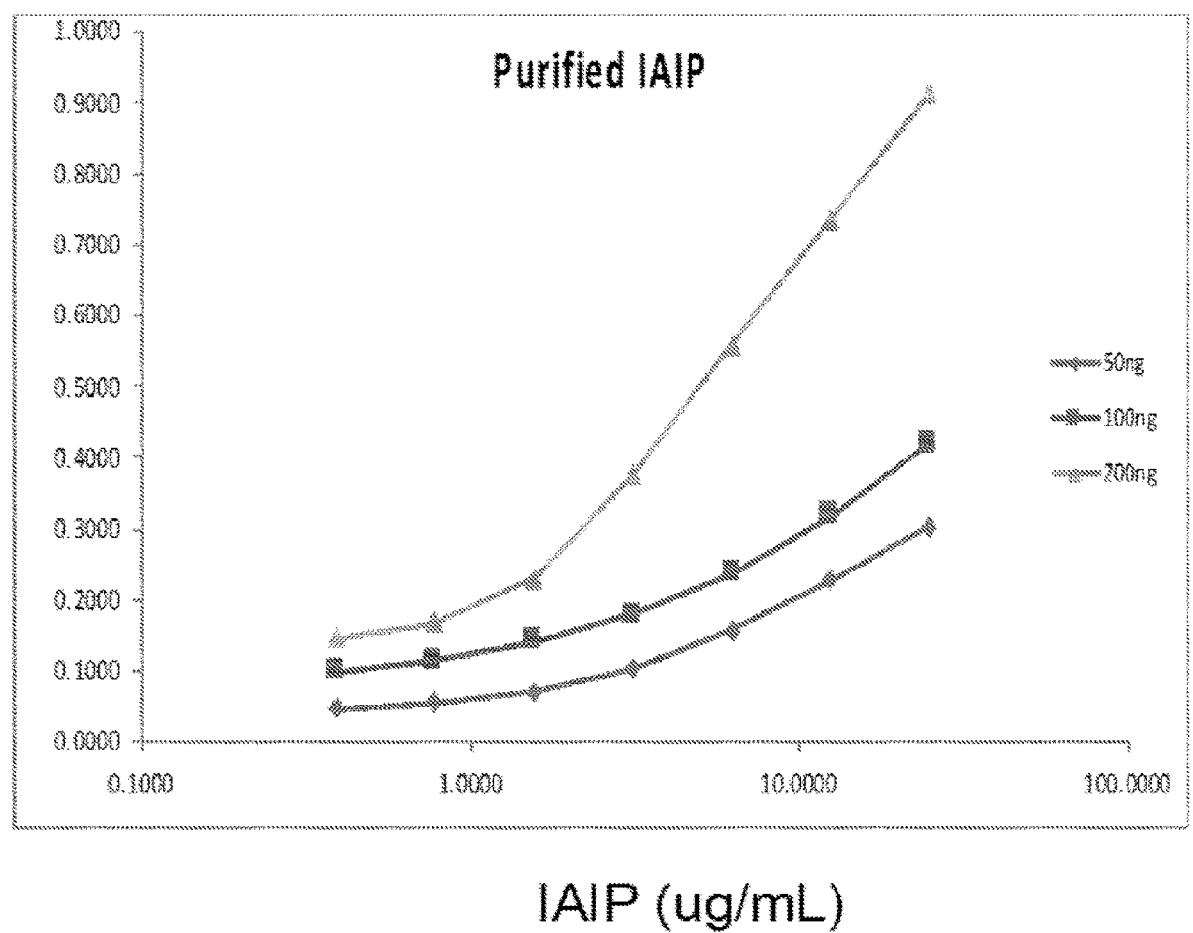

Following three additional washes with TBS-T, horseradish peroxidase (HRP)-conjugated Streptavidin (Inova Bioscience) diluted to 1:5000 in TBS was added and incubated at 37° C. for 30 minutes. After washing 3 times with TBS-T, 50 μL Enhanced K-Blue TMB Substrate (Neogen) was added to each well and the reaction was stopped by adding 50 μL 1M hydrochloric acid (HCl). The color change was read using a spectrophotometer (Molecular Devices SpectraMax Plus microplate reader) at 650 nm wavelength, and the standard curve for human plasma or purified IAIP was plotted at 50, 100 and 200 ng/well immobilized hyaluronic acid (FIGS. 21A-21B). These data show that IAIP can be quantitatively measured in biological mixtures by capturing IAIP complex molecules using hyaluronic acid and detecting the captured IAIP using a monoclonal antibody specific for the light chain of IAIP (e.g., MAb 69.26). As shown in FIGS. 21A-21B, a standard curve can be optimized and established using purified IAIP or human plasma with a known amount of IAIP. Consequently, this assay can be used to quantify an unknown amount of IAIP in a biological sample from a subject. An alternative approach to this method can be employed, in which an IAIP-specific monoclonal antibody is used to capture IAIP and biotin-labeled hyaluronic acid is used as a ligand to detect the bound IAIP, similar to the approaches used in Examples 1 and 2.

OTHER EMBODIMENTS

All publications, patents, and patent applications mentioned in the above specification are hereby incorporated by reference to the same extent as if each individual publication, patent or patent application was specifically and individually indicated to be incorporated by reference in its entirety. U.S. Provisional Application Nos. 62/490,003 and 62/614,333 are specifically incorporated herein in their entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method for quantifying intact inter-alpha inhibitor protein (IAIP) in a sample from a subject comprising:
   a) contacting the sample with a binding agent to produce an IAIP-binding agent complex, wherein the binding agent is bound to a support, and wherein the binding agent comprises an antibody that specifically binds to bikunin;
   b) contacting the IAIP-binding agent complex with a detection agent, wherein the detection agent comprises an IAIP ligand that binds to at least one IAIP heavy chain and does not bind to free bikunin, and wherein the IAIP ligand is selected from the group consisting of endotoxin (LPS), heparin, a histone, vitronectin, fibronectin, laminin, tenascin C, aggrecan, von Willebrand Factor, pentraxin-3 (PTX3), TNF-stimulated gene-6 (TSG-6), factor IX, a complement component, factor XIIIa, and tissue transglutaminase; and
   c) detecting an amount of the detection agent bound to the IAIP-binding agent complex, wherein the intact IAIP comprises bikunin and at least one IAIP heavy chain selected from the group consisting of H1, H2, and H3 chain;
thereby quantifying the intact IAIP in the sample.

2. The method of claim 1, wherein the contacting in step a) and/or b) is performed at a pH of about 7.0 to about 3.5.

3. The method of claim 2, wherein the pH is about 5.0 to about 3.5.

4. The method of claim 3, wherein the pH is about 4.0.

5. The method of claim 1, further comprising, prior to or during step a), adding a divalent cation to the sample.

6. The method of claim 1, wherein the subject is a human subject.

7. The method of claim 1, wherein the IAIP ligand is heparin or a histone.

8. The method of claim 7, wherein the IAIP ligand is heparin.

9. The method of claim 1, wherein the detection agent comprises a label.

10. The method of claim 9, wherein the label is biotin, a gold nanoparticle, a magnetic particle, a latex particle, an enzyme, an enzyme substrate, a fluorescent dye, a luminescent compound, or a radiolabel.

11. The method of claim 9, wherein the label is an enzyme and wherein the enzyme is horseradish peroxidase.

12. The method of claim 9, wherein the label comprises a gold nanoparticle.

13. The method of claim 9, wherein the label comprises biotin and one of streptavidin or avidin.

14. The method of claim 9, wherein the label is a gold nanoparticle and the IAIP ligand is heparin.

15. The method of claim 1, wherein the sample comprises blood, urine, cerebrospinal fluid, synovial fluid, amniotic fluid, interstitial fluid, follicular fluid, peritoneal fluid, bronchoalveolar lavage fluid, breast milk, sputum, lymph, bile, or tissue homogenate.

16. The method of claim 15, wherein the sample is blood, cerebrospinal fluid, bronchoalveolar lavage fluid, synovial fluid, or sputum.

17. The method of claim 16, wherein the sample is blood.

18. The method of claim 17, wherein the blood is plasma or serum.

19. The method of claim 1, wherein the support is a plate, a particle, a nanoparticle, a resin, a membrane, a biochip, a container, a test strip, or a bead.

20. The method of claim 1, wherein the support is a test strip.

* * * * *